US008114416B2

(12) United States Patent
Johansson et al.

(10) Patent No.: US 8,114,416 B2
(45) Date of Patent: Feb. 14, 2012

(54) MODIFIED ONCOLYTIC VIRUSES

(75) Inventors: Eva Susanne Johansson, The Hill (AU); Darren Raymond Shafren, The Hill (AU)

(73) Assignee: Viralytics Limited, Pymble (AU)

( * ) Notice: Subject to any disclaimer, the term of this patent is extended or adjusted under 35 U.S.C. 154(b) by 246 days.

(21) Appl. No.: 10/592,395

(22) PCT Filed: Jan. 17, 2005

(86) PCT No.: PCT/AU2005/000048

§ 371 (c)(1), (2), (4) Date: Jul. 3, 2007

(87) PCT Pub. No.: WO2005/087931
PCT Pub. Date: Sep. 22, 2005

(65) Prior Publication Data

US 2008/0057036 A1 Mar. 6, 2008

Related U.S. Application Data

(60) Provisional application No. 60/552,095, filed on Mar. 11, 2004.

(51) Int. Cl.
*A61K 39/125* (2006.01)
*C07H 21/02* (2006.01)
*C07H 21/04* (2006.01)
*C07K 1/00* (2006.01)

(52) U.S. Cl. ................. 424/216.1; 536/23.1; 536/23.72; 530/350

(58) Field of Classification Search ............... 424/216.1; 536/23.1, 23.72; 530/350
See application file for complete search history.

(56) References Cited

FOREIGN PATENT DOCUMENTS

WO WO 01/37866 5/2001

OTHER PUBLICATIONS

Reischl et al., 2001, Journal of Virology, vol. 75, No. 19, p. 9312-9319.*
Shafren D., 1998, Journal of Virology, vol. 72, No. 11, p. 9407-9412.*
Newcombe et al., 2003, Journal of General Virology, vol. 84, p. 3041-3050.*
Newcombe et al., Feb. 2004, Journal of Virology, vol. 78, No. 3, p. 1431-1439.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
Newcombe et al., "Cellular receptor interactions of C-cluster human group A coxsackieviruses", *J. Gen. Virol.*, 84(Pt 11):3041-3050 (2003).
Newcombe et al., "Enterovirus capsid interactions with decay-accelerating factor mediate lytic cell infection", *J. Virol.*, 78(3):1431-1439 (2004).
Shafren et al., "Cytoplasmic interactions between decay-accelerating factor and intercellular adhesion molecule-1 are not required for coxsackievirus A21 cell infection", *J. Gen. Virol.*, 81(Pt 4):889-894 (2000).
Shafren et al., "Systemic therapy of malignant human melanoma tumors by a common cold-producing enterovirus, coxsackievirus a21", *Clin. Cancer Res.*, 10(1 Pt 1):53-60 (2004).
Shafren, D., "Viral Cell Entry Induced by Cross-Linked Decay-Accelerating Factor," *Journal of Virology*, Nov. 1998, pp. 9407-9412, vol. 72, No. 11.
Johansson, S. et al., "Enhanced Cellular Receptor Usage by a Bioselected Variant of Coxsackievirus A21" *Journal of Virology*, Nov. 2004, pp. 12603-12612, vol. 78, No. 22.
Reischl, A. et al., "Viral Evolution Toward Change in Receptor Usage: Adaptation of a Major Group Human Rhinovirus to Grow on ICAM-1-Negative Cells," *Journal of Virology*, Oct. 2001, pp. 9312-9319, vol. 75, No. 19.

* cited by examiner

*Primary Examiner* — Shin-Lin Chen
(74) *Attorney, Agent, or Firm* — DLA Piper LLP (US)

(57) ABSTRACT

An isolated selected Picornavirus capable of lytically infecting or killing a cell substantially in the absence of intercellular adhesion molecule-1 (ICAM-1).

12 Claims, 27 Drawing Sheets

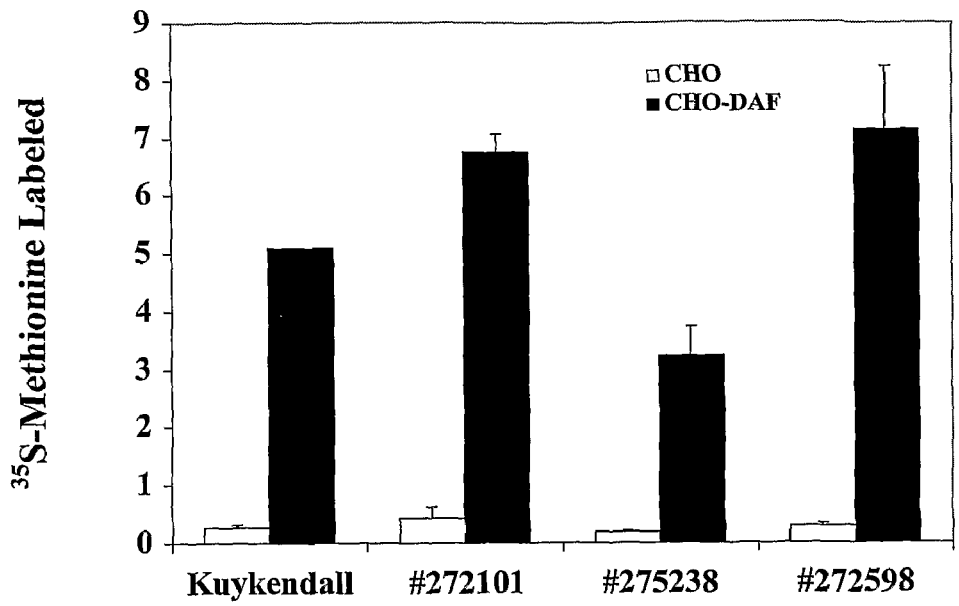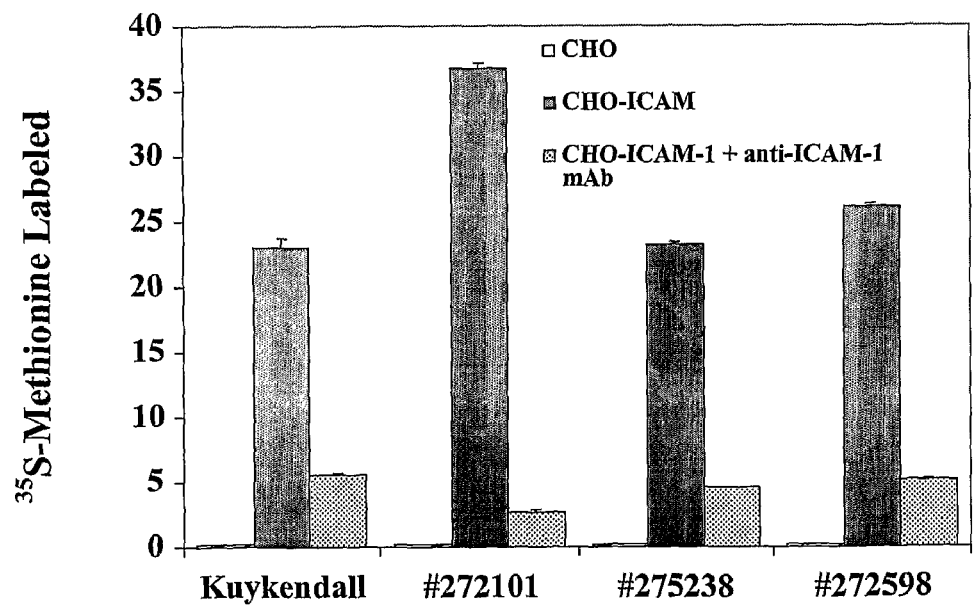
Figure 1

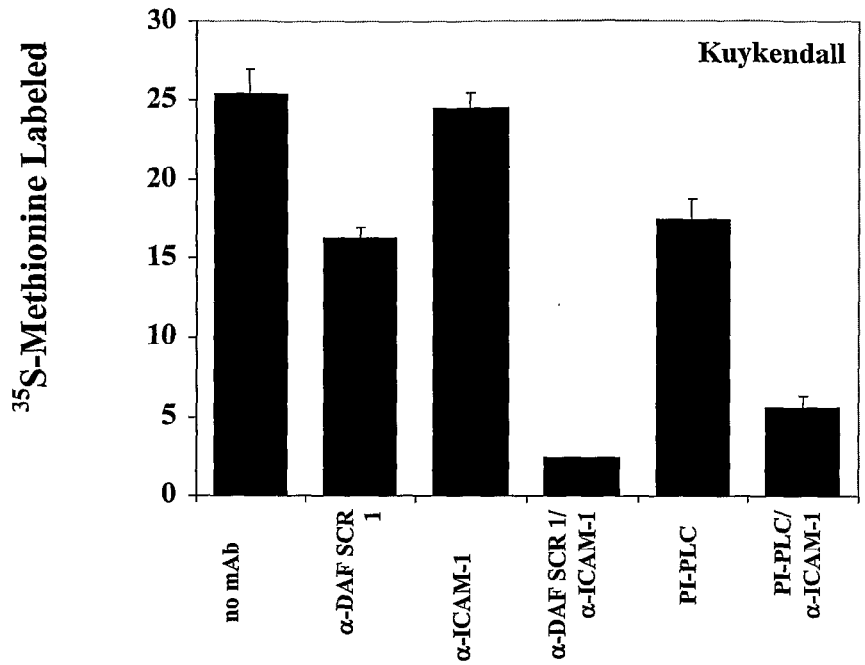
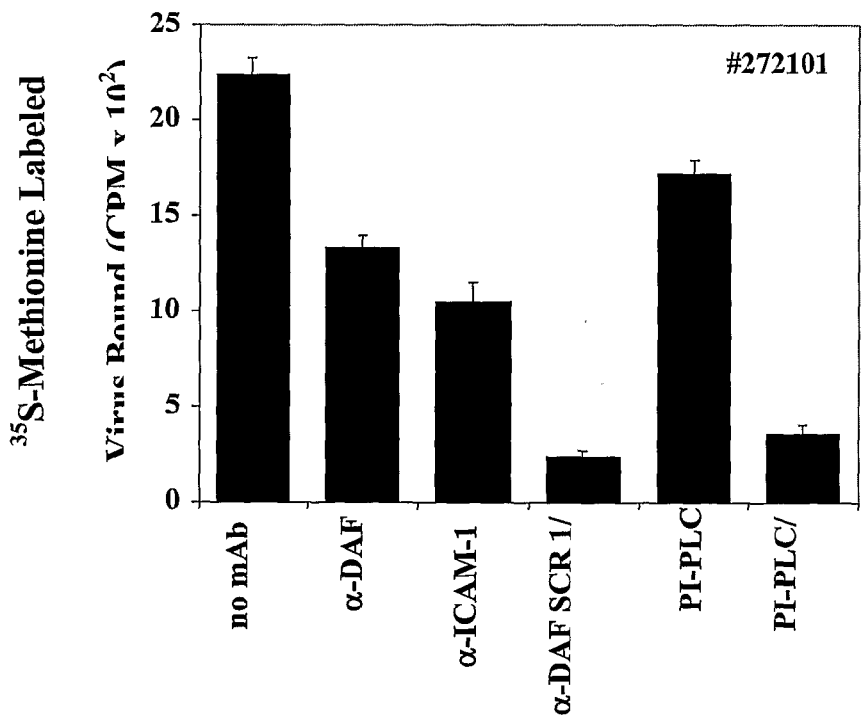
Figure 2

A
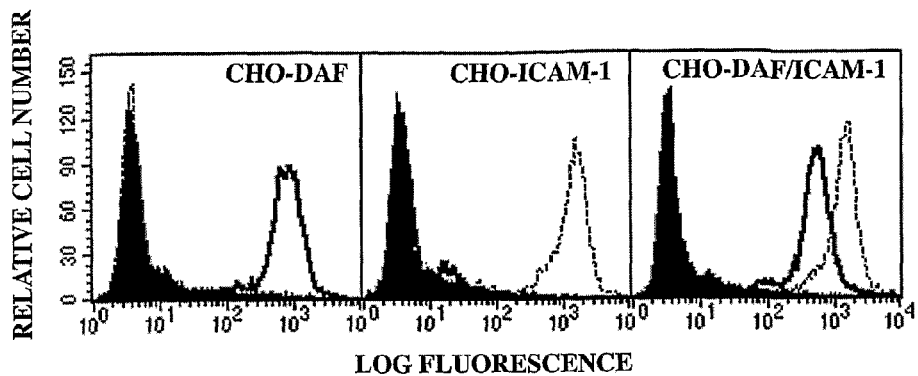
B
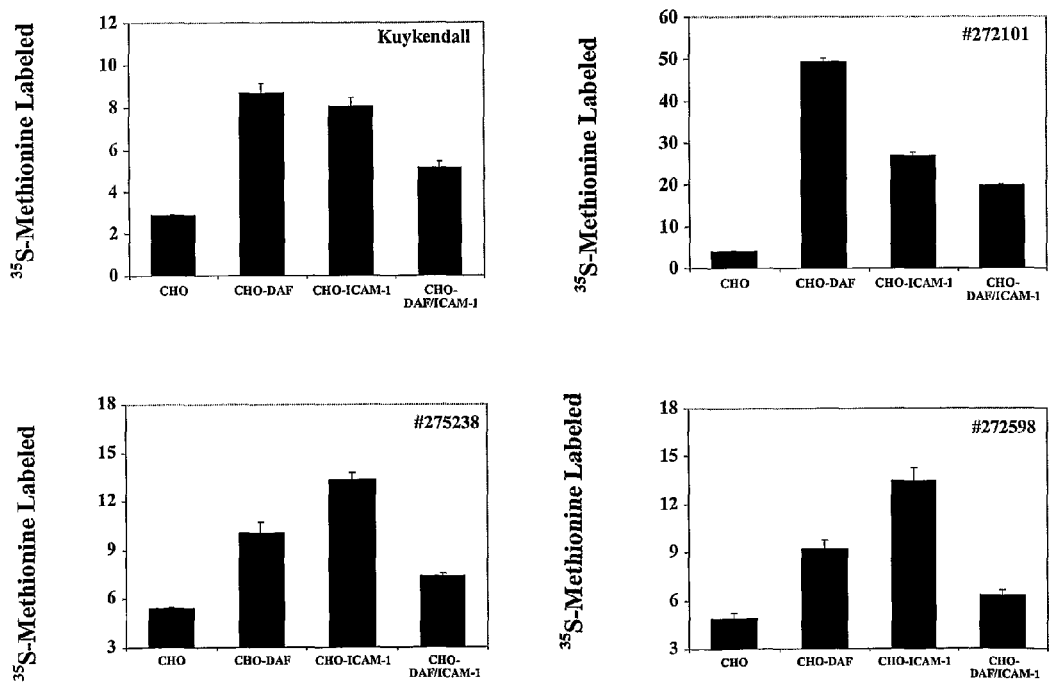
Figure 3

VP1

```
              *         20         *         40         *         60         *  αZ  80        BC loop
CVA21KK  GIEDLIDTAIKNALRVSQPPSTQSTEATSGVNSQEVPALTAVETGASGQAIPSDVVETRHVVNYKTRSESCLESFFGRAACVTILSLTNSSKSGEEKKHF
#272101  .......S...S........STA........A...........M.....I..............................ER...R...
#272598  .......S............STA........A...........M.....I...........................................
#275238  .......S............STA........A...........M.....I...........................................

βC        *        120         *        140         βE        160   αB      180         *        200
CVA21KK  NIMNLTYTDTVQLRRKLEFFTYSRFDLEMTFVFTENYPSTASGEVRNQVYQIMYIPPGAPRPSSWDDYTWQSSSNPSIFYMYGNAPPRMSIPYVGIANAY
#272101  .....................................................................................
#272598  .....................................................................................
#275238  .....................................................................................

GH loop                  240         *        260         *        280         *
CVA21KK  SHFYDGFARVPLEGENTDAGDTPYGLVSINDFGVLAVRAVNRSNPHTIHTSVRVYMKPKHIRCWCPRPPRAVLYRGEGVDMISSAILPLTKVDSITTF
#272101  ............................................................................E.......
#272598  ............................................................................
#275238  ............................................................................
```

VP2

```
              *         20         *         40         *         60         *         80         *        100
CVA21KK  SFNVEACGYSDRVRQITLGNSTITTQEAANAIVAYGEWPTYINDSEANPVDAPTEPDVSSNRFYTLESVSWKTTSRGWWWKLPDCLKDMGMFGQNMYYHY
#272101  .....................................................................................
#272598  .....................................................................................
#275238  .....................................................................................

*        120         *        140         *         PUFF                              *        200
CVA21KK  LGRSGYTIHVQCNASKFHQGALGVFLIPEFVMACNTESKTSYVSYINANPGERGGEFTNTYNPSNTDASEGRKFAALDYLLGSGVLAGNAFVYPHQIINL
#272101  ......................................................D...N...Q................
#272598  ...................................................................Q................
#275238  ...................................................................Q................

*        220         *        240         *        260         *
CVA21KK  RTNNSATIVVPYVNSLVIDCMAKHNNWGIVILPLAPLAFAATSSPQVPITVTIAPMCTEFNGLRNITVPVHQ
#272101  ...........................................A.........I....
#272598  ...........................................A.........I....
#275238  ...........................................A.........I....
```

VP3

```
              *         20         *         40         *         60         *    βC    *       αA
CVA21KK  GLPTMNTPGSNQFLTSDDFQSPCALPNFDVTPPIHIPGEVKNMMELAEIDTLIPMNAVDGKVNTMEMYQIPLNDNLSKAPIFCLSLSPASDKRLSRTMLG
#272101  ..........................................................................R..RH....
#272598  ..........................................................................H....
#275238  ..........................................................................H....

*        120         *        140         *        160         *   GH loop  *        200
CVA21KK  EILNYYTHWTGSIRFTFLFCGSMMATGKLLLSYSPPGAKPPTNRKDAMLGTHIIWDLGLQSSCSMVAPWISNTVYRRCAFDDFTEGGFITCFYQTRIVVP
#272101  ..............................................................................
#272598  ..............................................................................
#275238  ..............................................................................

*        220         *        240
CVA21KK  ASTPTSMFMLGFVSACPDFSVRLLRDTPHISQSKLIGRTQ
#272101  .....................S........A.A.
#272598  .....................S........A.S.
#275238  .....................S........A.S.
```

Figure 5

A
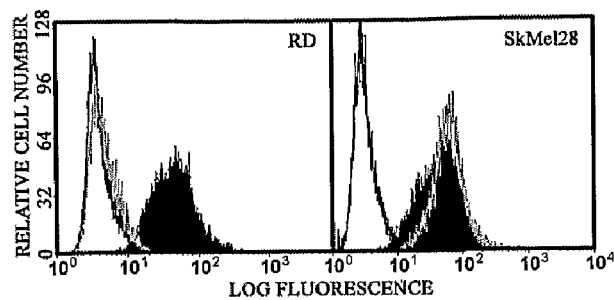
B
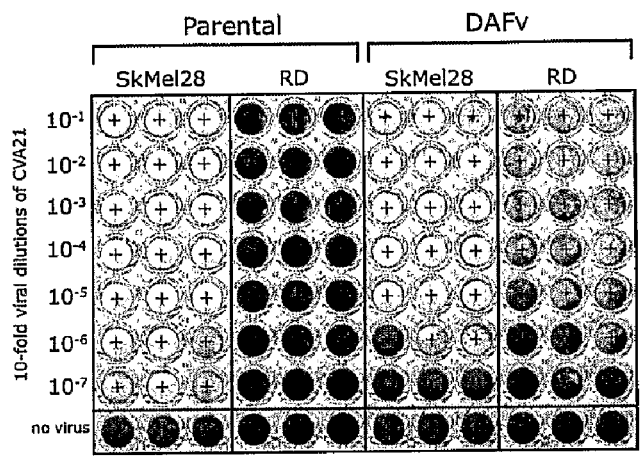
C
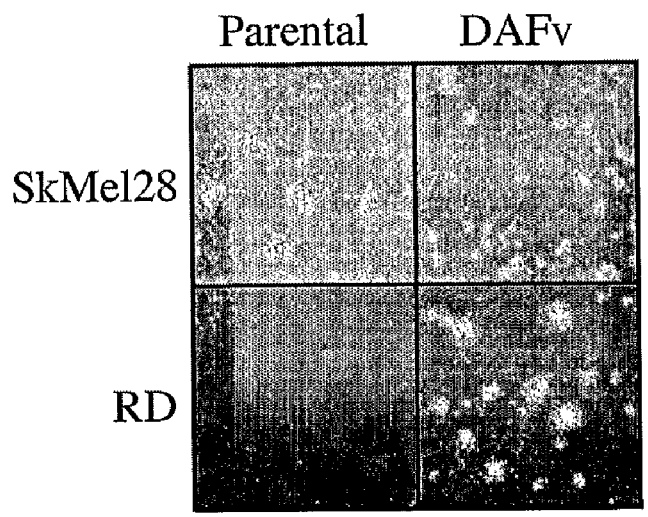
Figure 6

CVA21 #272598 nucleotide sequence for capsid coding region

```
atgggggctcaagtctcaactcaaaagaccggtgcgcacgagaatcaaaacgtggcagctaa
tggatccaccattaattatactactatcaattactacaaagatagcgcgagtaattcggcca
ctagacaagatctttcccaagatccatcaaaattcacggaaccggttaaggacttaatgttg
aaacagcaccagctttaaattcaccaaatgtggaagcatgtggatacagtgaccgtgtaag
acaaattaccctgggtaactcaaccattaccacacaagaagcagctaatgctattgttgctt
atggtgagtggcctacttacataaatgactcagaagcaaacccagtagatgcacccactgaa
ccagacgttagtagcaacaggttttacaccctagaatcggtgtcttggaagactacctcaag
gggttggtggtggaaactaccagactgtctaaaagacatgggaatgtttggtcagaacatgt
actaccactacttaggacgctctggttataccattcatgtccagtgcaatgcctcaaaattt
caccaaggggcattaggagttttctgataccagagtttgtcatggcctgcaacactgagag
caaaacatcatatgtttcatacattaacgcaaatcctggtgagaggggcggtgagttcacaa
acacctacaacccatcaaacacagatgctagtgagggcagacaattcgcagcactagactat
ctgctgggttctggcgttctagctggaaacgcatttgtgtaccgcaccagatcattaactt
gcgtaccaataacagtgcaacaatcgtggtgccatatgtgaactcacttgtcattgattgca
tggcaaaacataataactggggcattgtcattctaccactggcacccttggcctttgctgca
acatcgtcaccacaggtgcctattacagtgaccattgcacccatgtgcgcagaattcaatgg
attgagaaacatcaccatcccagtgcatcaagggttgccaacaatgaatacacctggttcca
atcaattcctcacatctgatgacttccagtcaccctgcgccttacccaattttgatgtcact
ccgccaatacacatacccggagaagtgaagaacatgatggaactggctgaaattgacacgct
gatcccaatgaatgcagtggacggaaaggtgaacactatggaatgtatcaaataccattaa
atgacaatttgagcaaggcacccatattttgcctatctctgtcgcctgcttctgacaaacga
ttaagtcatacaatgttgggtgaaattctaaattattacacccattggacagggtccattag
gttcacctttctattttgtggtagtatgatggctactggtaagctacttctcagttattccc
caccaggagctaaaccaccaaccaatcgcaaagatgcaatgttgggcacacacatcatctgg
gacctggggttacaatccagttgttccatggttgcaccgtggatctctaatacagtatacag
gcggtgcgcacgtgatgacttcacagaaggcgggtttataacttgcttttatcaaactagaa
ttgttgtgcctgcttcaactctaccagtatgtttatgttaggctttgtgagtgcatgtcca
gatttcagtgtcagactgcttagggacacttcccacattagtcaatcaaaactaatagcacg
ctcacaaggcattgaagaccttattgactcagcgataaagaatgctttgagagtgtctcaac
catctacggcccagtcaactgaagcaaccagtggagcaaatagtcaggaagtgccagcacta
actgctgtggaaacaggagcatctggtcaggcaatccccagtgacgtgatggaaaccagaca
cgtgataaattacaaaactaggtctgaatcatgccttgagtcattctttgggagagctgcgt
gtgtcacaatcctatctctgaccaactcttccaagagtggcgaggagaaaaagcatttcaac
atttggaatatcacatacaccgacactgttcagttgcgtagaaaattagagttttcacata
ttccagatttgaccttgaaatgacttttgtgttcacagagaactacccagtacagctagtg
gagaagtgcgcaaccaagtataccagatcatgtacattccaccaggggcacccgtccatca
tcctgggatgactatacatggcaatcctcctccaaccttccatcttttacatgtatgggaa
cgcaccaccgcggatgtcaattccttacgtggggattgccaatgcctattcacacttctatg
acggttttgcacgagtgccacttgagggtgagaatactgatgctggtgatacgttttatgga
ttggtgtccataaacgattttggagtcttagcagtcagagcagtaaaccgcagtaatccaca
tacaatacacacatccgtgagagtgtacatgaaaccaaaacacattcggtgttggtgcccca
gacccctcgcgctgtattatacagaggagaaggagtagacatgatatccagtgcaattcta
cccctgactaaagtggactcaattaccactttt
```

Figure 20(A)

CVA21 #272598 amino acid sequence for capsid coding region

MGAQVSTQKTGAHENQNVAANGSTINYTTINYYKDSASNSATRQDLSQDPSKFTEPVKDLML
KTAPALNSPNVEACGYSDRVRQITLGNSTITTQEAANAIVAYGEWPTYINDSEANPVDAPTE
PDVSSNRFYTLESVSWKTTSRGWWWKLPDCLKDMGMFGQNMYYHYLGRSGYTIHVQCNASKF
HQGALGVFLIPEFVMACNTESKTSYVSYINANPGERGGEFTNTYNPSNTDASEGRQFAALDY
LLGSGVLAGNAFVYPHQIINLRTNNSATIVVPYVNSLVIDCMAKHNNWGIVILPLAPLAFAA
TSSPQVPITVTIAPMCAEFNGLRNITIPVHQGLPTMNTPGSNQFLTSDDFQSPCALPNFDVT
PPIHIPGEVKNMMELAEIDTLIPMNAVDGKVNTMEMYQIPLNDNLSKAPIFCLSLSPASDKR
LSHTMLGEILNYYTHWTGSIRFTFLFCGSMMATGKLLLSYSPPGAKPPTNRKDAMLGTHIIW
DLGLQSSCSMVAPWISNTVYRRCARDDFTEGGFITCFYQTRIVVPASTPTSMFMLGFVSACP
DFSVRLLRDTSHISQSKLIARSQGIEDLIDSAIKNALRVSQPSTAQSTEATSGANSQEVPAL
TAVETGASGQAIPSDVMETRHVINYKTRSESCLESFFGRAACVTILSLTNSSKSGEEKKHFN
IWNITYTDTVQLRRKLEFFTYSRFDLEMTFVFTENYPSTASGEVRNQVYQIMYIPPGAPRPS
SWDDYTWQSSSNPSIFYMYGNAPPRMSIPYVGIANAYSHFYDGFARVPLEGENTDAGDTFYG
LVSINDFGVLAVRAVNRSNPHTIHTSVRVYMKPKHIRCWCPRPPRAVLYRGEGVDMISSAIL
PLTKVDSITTF

Figure 20(B)

CVA21 #275238 nucleotide sequence for capsid coding region atggggctcaagtctcaactcaaaagaccggtgcgcacgagaatcaaaacgtggcagctaa
tggatccaccattaattatactactatcaattactacaaagatagcgcgagtaattcggcca
ctagacaagatctttcccaagatccatcgaaattcacggaaccggttaaggacttaatgttg
aaaacagcaccagctttaaattcaccaaatgtggaagcatgtggatacagtgaccgtgtaag
acaaattaccctgggtaactcaaccattaccacacaagaagcagctaatgctattgttgctt
atggtgagtggcctacttacataaatgactcagaagcaaacccagtagatgcacccactgaa
ccagacgttagtagcaacaggttttacaccctagaatcggtgtcttggaagactacctcaag
gggttggtggtggaaactaccagactgtctaaaagacatgggaatgtttggtcagaacatgt
actaccactacttaggacgctctggttataccattcatgtccagtgcaatgcctcaaaattt
caccaaggggcattaggagtttttctgataccagagtttgtcatggcctgcaacactgagag
caaaacatcatatgtttcatacattaacgcaaatcctggtgagaggggcggtgagttcacaa
acacttacaacccatcaaacacagatgctagtgagggcagacaattcgcagcactagactat
ctgctgggttctggcgttctagctggaaacgcatttgtgtacccgcaccagatcattaactt
gcgtaccaataacagtgcaacaatcgtggtgccatatgtgaactcacttgtcattgattgca
tggcaaaacataataactggggcattgtcattctaccactggcacccttggcctttgctgca
acatcgtcaccacaggtgcctattacagtgaccattgcacccatgtgcgcagaattcaatgg
attgagaaacatcaccatcccagtgcatcaagggttgccaacaatgaatacacctggttcca
atcaattcctcacatctgatgacttccagtcaccctgcgccttacccaattttgatgtcact
ccgccaatacacatacccggagaagtgaagaacatgatggaattggctgaaattgacacgct
gatcccaatgaatgcagtggacggaaaggtgaacactatggaaatgtatcaaataccattaa
atgacaatttgagcaaggcacccatatttgcctatctctgtcgcctgcttctgacaaacga
ttaagtcatacaatgttgggtgaaattctaaattattacacccattggacagggtccattag
gttcacctttctattttgtggtagtatgatggctactggtaagctacttctcagttattccc
caccaggagctaaaccaccaaccaatcgcaaagatgcaatgttgggcacacacatcatctgg
gacctggggttacaatccagttgttccatggttgcaccgtggatctctaatacagtatacag
gcggtgcgcacgtgatgacttcacagaaggcgggtttataacttgcttttatcaaactagaa
ttgttgtgcctgcttcaactcctaccagtatgtttatgttaggctttgtgagtgcatgtcca
gatttcagtgtcagactgcttagggacacttcccacattagtcaatcaaaactaatagcacg
ctcacaaggcattgaagaccttattgactcagcgataaagaatgctttgagagtgtctcaac
catctacggcccagtcaactgaagcaaccagtggagcaaatagtcaggaagtgccagcacta
actgctgtggaaacaggagcatctggtcaggcaattcccagtgacgtgatggaaaccagaca
cgtgataaattacaaaactaggtctgaatcatgccttgagtcattctttgggagagctgcgt
gtgtcacaatcctatctctgaccaactcttccaagagtggcgaggagaaaagcatttcaac
atttggaatatcacatacaccgacactgttcagttgcgtagaaaattagagtttttcacata
ttccagatttgaccttgaaatgacttttgtgttcacagagaactaccccagtacagctagtg
gagaagtgcgcaaccaagtataccagatcatgtacattccaccaggggcaccccgtccatca
tcctgggatgactatacatggcaatcctcctccaacccttccatcttttacatgtatggaa
cgcaccaccgcggatgtcaattccttacgtggggattgccaatgcctattcacacttctatg
acggttttgcacgagtgccacttgagggtgagaatactgatgctggtgatacgttttatgga
ttggtgtccataaacgattttggagtcttagcagtcagagcagtaaaccgcagtaatccaca
tacaatacacacatccgtgagagtgtacatgaaccaaaacacattcggtgttggtgcccca
gacccccctcgcgctgtattatacagaggagaaggagtagacatgatatccagtgcaattcta
cccctgactaaagtggactcaattaccactttt

Figure 21(A)

CVA21 #275238 amino acid sequence for capsid coding region

MGAQVSTQKTGAHENQNVAANGSTINYTTINYYKDSASNSATRQDLSQDPSKFTEPVKDLML
KTAPALNSPNVEACGYSDRVRQITLGNSTITTQEAANAIVAYGEWPTYINDSEANPVDAPTE
PDVSSNRFYTLESVSWKTTSRGWWWKLPDCLKDMGMFGQNMYYHYLGRSGYTIHVQCNASKF
HQGALGVFLIPEFVMACNTESKTSYVSYINANPGERGGEFTNTYNPSNTDASEGRQFAALDY
LLGSGVLAGNAFVYPHQIINLRTNNSATIVVPYVNSLVIDCMAKHNNWGIVILPLAPLAFAA
TSSPQVPITVTIAPMCAEFNGLRNITIPVHQGLPTMNTPGSNQFLTSDDFQSPCALPNFDVT
PPIHIPGEVKNMMELAEIDTLIPMNAVDGKVNTMEMYQIPLNDNLSKAPIFCLSLSPASDKR
LSHTMLGEILNYYTHWTGSIRFTFLFCGSMMATGKLLLSYSPPGAKPPTNRKDAMLGTHIIW
DLGLQSSCSMVAPWISNTVYRRCARDDFTEGGFITCFYQTRIVVPASTPTSMFMLGFVSACP
DFSVRLLRDTSHISQSKLIARSQGIEDLIDSAIKNALRVSQPSTAQSTEATSGANSQEVPAL
TAVETGASGQAIPSDVMETRHVINYKTRSESCLESFFGRAACVTILSLTNSSKSGEEKKHFN
IWNITYTDTVQLRRKLEFFTYSRFDLEMTFVFTENYPSTASGEVRNQVYQIMYIPPGAPRPS
SWDDYTWQSSSNPSIFYMYGNAPPRMSIPYVGIANAYSHFYDGFARVPLEGENTDAGDTFYG
LVSINDFGVLAVRAVNRSNPHTIHTSVRVYMKPKHIRCWCPRPPRAVLYRGEGVDMISSAIL
PLTKVDSITTF

Figure 21(B)

CVA21 #272101 nucleotide sequence for capsid coding region atggggctcaagtctcaactcaaaagaccggtgcgcacgagaatcaaaacgtggcagctaa
tggatccaccattaattatactactattaattactacaaagatagcgcgagtaattcggcta
ctagacaagatctttcccaagatccatcaaaattcacggaaccggttaaggacttaatgttg
aaaacagcaccagctttaaattcaccaaatgtggaagcatgtggatacagtgaccgtgtaag
acagattaccctgggtaattcaaccattaccacacaagaagcagctaatgctattgttgctt
atggtgagtggcctacttacataaatgactcagaagcaaacccagtagatgcacccactgaa
ccagacgttagtagcaacaggttttacaccttagaatcggtgtcttggaagactacctcaag
gggttggtggtggaaactaccagactgtctaaaagacatgggaatgtttggtcaaaacatgt
actaccactacttaggacgctctggttataccattcatgtccagtgcaatgcgtcaaaattt
caccaaggggcattaggagtttttctgataccagagtttgtcatggcctgcaacactgagag
caaaacatcatatgtttcatacattaacgcaaatcctggtgagaggggcggtgagtttacaa
acacctataacccatcagacacagatgctaatgagggcagacaattcgcagcactagactat
ttgctgggttctggtgttctagctggaaacgcatttgtgtacccgcaccagatcattaactt
gcgtaccaataacagtgcaacaattgtggtaccatatgtgaactcacttgtcattgattgca
tggcaaaacacaataactggggcattgtcattctgccactggcacccttggcctttgctgca
acatcgtcaccacaggtgcctattacagtgaccattgcacccatgtgcgcagaattcaatgg
attgagaaacatcaccatcccagtgcatcaagggttgccaacaatgaatacacctggttcca
atcaattcctcacatctgatgacttccagtcgccctgcgccttgcccaatttcgatgtcact
ccgccaatacacatacccggagaagtgaagaacatgatggaactggctgaaattgacacact
gatcccaatgaatgcagtggacggaaaggtgaacactatggaaatgtatcaaataccattaa
atgacaatttgagcaaggcacccatattttgcctatctctgtcgcctgcttctgacagacga
ctacgtcatacaatgttgggtgaaattctaaattattacacccattggacagggtccattag
gttcacctttctattttgtggtagtatgatggctactggtaagctacttctcagttattccc
caccaggagctaaaccaccaaccaatcgcaaagatgcaatgttgggcacacacatcatctgg
gacctgggattacaatccagttgttccatggttgcaccgtggatctctaatacagtatacag
gcggtgcgcacgtgatgacttcacagaaggcgggtttataacttgcttttatcaaactagaa
ttgttgtgcctgcttcaactcctaccagtatgtttatgttaggctttgtgagtgcatgtcca
gatttcagtgtcagactgcttagggacacttcccatattagtcaatcaaaattaatagcacg
cgcacaaggcattgaagaccttattgactcagcgataaagagtgctttgagagtgtctcaac
catctacggcccagtcaactgaagcaaccagtggagcaaatagtcaggaagtgccagcacta
actgctgtggaaacaggagcatctggtcaggcaatccccagtgacgtgatggaaaccagaca
cgtgataaattacaaaaccaggtctgaatcatgccttgagtcattctttgggagagctgcgt
gtgtcacaatcctatctctgactaactcttccgagagaggggaggagaggaagcatttcaac
atttggaatatcacatacaccgacactgttcagttgcgtagaaaattggagtttttcacata
ttccagatttgaccttgaaatgacttttgtgttcacagagaactatcccagtacagccagtg
gagaagtgcgcaaccaagtataccagatcatgtacattccaccaggggcaccccgtccatca
tcctgggatgactatacatggcaatcctcctccaacccttccatcttttacatgtatggaa
cgcaccaccgcggatgtcaattccttacgtggggattgccaatgcctattcacacttctacg
acggttttgcacgagtgccacttgagggtgagaatactgatgctggtgacacgttttatgga
ttggtgtccataaacgattttggagtcttagcagtcagagcagtaaaccgcagtaatccaca
tacaatacacacatccgtgagagtgtacatgaagccaaaacacattcggtgttggtgcccca
gacccccctcgtgctgtattatacagaggagaaggagtagacatgatatccagtgcaattcta
cccctgactgaagtggactcaattaccactttt

Figure 22(A)

CVA #272101 amino acid sequence for capsid coding region

MGAQVSTQKTGAHENQNVAANGSTINYTTINYYKDSASNSATRQDLSQDPSKFTEPVKDLML
KTAPALNSPNVEACGYSDRVRQITLGNSTITTQEAANAIVAYGEWPTYINDSEANPVDAPTE
PDVSSNRFYTLESVSWKTTSRGWWWKLPDCLKDMGMFGQNMYYHYLGRSGYTIHVQCNASKF
HQGALGVFLIPEFVMACNTESKTSYVSYINANPGERGGEFTNTYNPSDTDANEGRQFAALDY
LLGSGVLAGNAFVYPHQIINLRTNNSATIVVPYVNSLVIDCMAKHNNWGIVILPLAPLAFAA
TSSPQVPITVTIAPMCAEFNGLRNITIPVHQGLPTMNTPGSNQFLTSDDFQSPCALPNFDVT
PPIHIPGEVKNMMELAEIDTLIPMNAVDGKVNTMEMYQIPLNDNLSKAPIFCLSLSPASDRR
LRHTMLGEILNYYTHWTGSIRFTFLFCGSMMATGKLLLSYSPPGAKPPTNRKDAMLGTHIIW
DLGLQSSCSMVAPWISNTVYRRCARDDFTEGGFITCFYQTRIVVPASTPTSMFMLGFVSACP
DFSVRLLRDTSHISQSKLIARAQGIEDLIDSAIKSALRVSQPSTAQSTEATSGANSQEVPAL
TAVETGASGQAIPSDVMETRHVINYKTRSESCLESFFGRAACVTILSLTNSSERGEERKHFN
IWNITYTDTVQLRRKLEFFTYSRFDLEMTFVFTENYPSTASGEVRNQVYQIMYIPPGAPRPS
SWDDYTWQSSSNPSIFYMYGNAPPRMSIPYVGIANAYSHFYDGFARVPLEGENTDAGDTFYG
LVSINDFGVLAVRAVNRSNPHTIHTSVRVYMKPKHIRCWCPRPPRAVLYRGEGVDMISSAIL
PLTEVDSITTF

Figure 22(B)

CVA21-DAFv nucleotide sequence for capsid coding region

```
ATGGGGGCTCAAGTTTCAACGCAAAAGACCGGTGCGCACGAGAATCAAAACGTGGCAGCCAATGGATCC
ACCATTAATTACACTACTATCAACTATTACAAAGACAGTGCGAGTAATTCCGCTACTAGACAAGACCTC
TCCCAAGATCCATCAAAATTCACAGAACCGGTTAAGGACTTAATGTTGAAAACAGCACCAGCTCTAAAC
TCGCCTAACGTGGAAGCATGTGGGTACAGTGACCGTGTGAGGCAAATCACTTTAGGCAACTCGACTATT
ACTACACAAGAAGCAGCCAATGCTATTGTTGCTTACGGTGAATGGCCCACTTACATAAATGATTCAGAA
GCTAATCCGGTAGATGCACCCACTGAGCCAGATGTTAGTAGCAACCGGTTTTACACCCTAGAATCGGTG
TCTTGGAAGACCACTTCAAGGGGATGGTGGTGGAAGTTACCAGATTGTTTGAAGGACATGGGAATGTTT
GGTCAGAATATGTACTATCACTACTTGGGGCGCTCTGGTTACACCATTCATGTCCAGTGCAACGCTTCA
AAATTTCACCAAGGGGCGTTAGGAGTTTTTCTGATACCAGAGTTTGTCATGGCTTGCAACACTGAGAGT
AAAACGTCATACGTTTCATACATCAATGCAAATCCTGGTGAGAGAGGCGGTGAGTTTACGAACACCTAC
AATCCGTTAAATACAGACGCCAGTGAGGGCAGAAAGTTTGCAGCATTGGATTATTTGCTGGGTTCTGGT
GTTCTAGCAGGAAACGCCTTTGTGTACCCGCACCAGATCATCAACCTACGTACCAACAACAGTGCAACA
ATTGTGGTGCCATACGTAAACTCACTTGTGATTGATTGTATGGCAAAACACAATAACTGGGGCATTGTC
ATATTACCACTGGCACCCTTGGCCTTTGCCGCAACATCGTCACCACAGGTGCCTATTACAGTGACCATT
GCACCCATGTGTACAGAATTCAATGGGTTGAGAAACATCACCGTCCCAGTACATCAAGGGTTGCCGACA
ATGAACACACCTGGTTCCAATCAATTCCTTACATCTGATGACTTCCAGTCGCCCTGTGCCTTACCTAAT
TTTGATGTTACTCCACCAATACACATACCCGGGGAAGTAAAGAATATGATGGAACTAGCTGAAATTGAC
ACATTGATCCCAATGAACGCAGTGGACGGGAAGGTGAACACAATGGAGATGTATCAAATACCATTGAAT
GACAATTTGAGCAAGGCACCTATATTCTGTTTATCCCTATCACCTGCTTCTGATAAACGACTGAGCCAC
ACCATGTTGGGTGMAATCCTAAATTATTACACCCATTGGACGGGGTCCATCAGGTTCACCTTTCTATTT
TGTGGTAGTATGATGGCCACTGGTAAACTGCTCCTCAGCTATTCCCCACCGGGAGCTAAACCACCAACC
AATCGCAAGGATGCAATGCTAGGCACACACATCATCTGGGACCTAGGGTTACAATCCAGTTGTTCCATG
GTTGCACCGTGGATCTCCAACACAGTGTACAGACGGTGTGCACGTGATGACTTCACTGAGGGCGGATTT
ATAACTTGCTTCTATCAAACTAGAATTGTGGTACCTGCTTCAACCCCTACCAGTATGTTCATGTTAGGC
TTTGTTAGTGCGTGTCCAGACTTCAGTGTCAGACTGCTTAGGGACACTCCCCATATTAGTCAATCGAAA
CTAATAGGACGTACACAAGGCATTGAAGACCTCATTGACACAGCGATAAAGAATGCCTTAAGAGTGTCC
CAACCACCCTCGACCCAGTCAACTGAAGCAACTAGTGGAGTGAATAGCCAGGAGGTGCCAGCTCTAACT
GCTGTGGAAACAGGAGCATCTGGTCAAGCAATCCCCAGTGATGTGGTGGAAACTAGGCACGTGGTAAAT
TACAAAACCAGGTCTGAATCGTGTCTTGAGTCATTCTTTGGGAGAGCTGCGTGTGTCACAATCCTATCC
TTGACCAACTCCTCCAAGAGCGGAGAGGAGAAAAAGCATTTCAACATATGGAATATTACATACACCGAC
ACTGTCCAGTTACGCAGAAAATTAGAGTTTTTCACGTATTCCAGGTTTGATCTTGAAATGACTTTTGTA
TTCACAGAGAACTATCCTAGTACAGCCAGTGGAGAAGTGCGAAACCAGGTGTACCAGATCATGTATATT
CCACCAGGGGCACCCCGCCCATCATCCTGGGATGACTACACATGGCAATCCTCTTCAAACCCTTCCATC
TTCTACATGTATGGAAATGCACCTCCACGGATGTCAATTCCTTACGTAGGGATTGCCAATGCCTATTCA
CACTTCTACGATGGCTTTGCACGGGTGCCACTTGAGGGTGAGAACACCGATGCTGGCGACACGTTTTAC
GGTTTAGTGTCCATAAATGATTTTGGAGTTTTAGCAGTTAGAGCAGTAAACCGCAGTAATCCACATACA
ATACACACATCTGTGAGAGTGTACATGAAACCAAAACACATTCGGTGTTGGTGCCCCAGACCTCCTCGA
GCTGTATTATACAGGGGAGAGGGAGTGGACATGATATCCAGTGCAATTCTACCTCTGACCAAGGTAGAC
TCAATTACCACTTTT
```

CVA21-DAFv amino acid sequence for capsid coding region

MGAQVSTQKTGAHENQNVAANGSTINYTTINYYKDSASNSATRQDLSQDPSKFTEPVKDLMLKTAPALN
SPNVEACGYSDRVRQITLGNSTITTQEAANAIVAYGEWPTYINDSEANPVDAPTEPDVSSNRFYTLESV
SWKTTSRGWWWKLPDCLKDMGMFGQNMYYHYLGRSGYTIHVQCNASKFHQGALGVFLIPEFVMACNTES
KTSYVSYINANPGERGGEFTNTYNPLNTDASEGRKFAALDYLLGSGVLAGNAFVYPHQIINLRTNNSAT
IVVPYVNSLVIDCMAKHNNWGIVILPLAPLAFAATSSPQVPITVTIAPMCTEFNGLRNITVPVHQGLPT
MNTPGSNQFLTSDDFQSPCALPNFDVTPPIHIPGEVKNMMELAEIDTLIPMNAVDGKVNTMEMYQIPLN
DNLSKAPIFCLSLSPASDKRLSHTMLGXILNYYTHWTGSIRFTFLFCGSMMATGKLLLSYSPPGAKPPT
NRKDAMLGTHIIWDLGLQSSCSMVAPWISNTVYRRCARDDFTEGGFITCFYQTRIVVPASTPTSMFMLG
FVSACPDFSVRLLRDTPHISQSKLIGRTQGIEDLIDTAIKNALRVSQPPSTQSTEATSGVNSQEVPALT
AVETGASGQAIPSDVVETRHVVNYKTRSESCLESFFGRAACVTILSLTNSSKSGEEKKHFNIWNITYTD
TVQLRRKLEFFTYSRFDLEMTFVFTENYPSTASGEVRNQVYQIMYIPPGAPRPSSWDDYTWQSSSNPSI
FYMYGNAPPRMSIPYVGIANAYSHFYDGFARVPLEGENTDAGDTFYGLVSINDFGVLAVRAVNRSNPHT
IHTSVRVYMKPKHIRCWCPRPPRAVLYRGEGVDMISSAILPLTKVDSITTF

MODIFIED ONCOLYTIC VIRUSES

CROSS REFERENCE TO RELATED APPLICATIONS

This application is a 35 USC §371 National Stage application of PCT Application No. PCT/AU2005/000048 filed Jan. 17, 2005; which claims the benefit under 35 USC §119(e) to U.S. Application Ser. No. 60/552,095 filed Mar. 11, 2004, now abandoned. The disclosure of each of the prior applications is considered part of and is incorporated by reference in the disclosure of this application.

TECHNICAL FIELD

The present invention relates to modified oncolytic Picornavirus and methods for treating subjects.

BACKGROUND

The attachment of viruses to cell surface molecules is the initial step of virus replication and specific cellular virus receptors are, therefore, major determinants for virus tissue tropism. Decay-accelerating factor (DAF/CD55), a 70 kDa glycosyl phosphatidyl inositol (GPI) anchored complement regulatory protein consisting of four extracellular short consensus repeats (SCRs), serves as a membrane attachment protein for numerous human enteroviruses, including several echoviruses (EV), coxsackie B viruses (CVB) and Coxsackievirus A21 (CVA21). In general, viral binding to DAF alone is insufficient to permit enteroviral infections and interactions with DAF do not induce 135S altered (A) particles, which are considered to be a prerequisite for cell entry. The physiological role of DAF for enteroviral infections is postulated to be as a membrane sequestration receptor that binds and concentrates the infectious virus, resulting in increased opportunity for cell entry via interactions with a second functional cell entry receptor.

Like for many other picornaviral receptors (employed by polioviruses, the major receptor group rhinoviruses and coxsackie B viruses), the CVA21 cellular internalizing receptor, intercellular adhesion molecule-1 (ICAM-1/CD54), is a member of the immunoglobulin-superfamily and binds within the capsid canyon surrounding the fivefold axis. Interactions between the viral receptor at the base of the canyon destabilize the capsid and induce conformational changes, a prelude to viral uncoating.

The prototype strain of CVA21 (Kuykendall), a causal agent of respiratory infections, binds to both ICAM-1 and DAF. Binding of the prototype strain of CVA21 to surface expressed DAF is, however, not sufficient to initiate a productive infection or formation of A-particles, and interaction with ICAM-1 is required for cell entry. A more functional role for DAF during CVA21 infection is observed when surface DAF is cross-linked by a monoclonal antibody (mAb) directed against a non-viral binding domain of DAF, allowing infection in the absence of ICAM-1.

The present applicant previously developed new methods for treating malignancy using oncolytic viruses that recognise ICAM-1 (WO 01/37866). Excellent therapeutic results were obtained by using various Coxsackievirus A strains on a number of cancer cell types. In order to expand the possible cancer treatment and provide even more efficacious treatments, the present inventors have obtained new oncolytic viruses with improved oncolytic and killing properties by modification and bioselection.

SUMMARY OF INVENTION

In a first aspect, the present invention provides an isolated selected Picornavirus capable of lytically infecting or inducing apoptosis in a cell substantially in the absence of intercellular adhesion molecule-1 (ICAM-1).

Preferably, the selected Picornavirus is capable of lytically infecting a cell through decay-accelerating factor (DAF) on the cell.

Preferably, the Picornavirus is selected from the group consisting of both the prototype and clinically isolated strains of enteroviruses including Coxsackievirus, Echovirus, Poliovirus, unclassified enteroviruses, Rhinovirus, Paraechovirus, Hepatovirus, and Cardiovirus.

In a preferred form, the Picornavirus is a Coxsackievirus. Preferably, the Coxsackievirus is type A or B, more preferably Coxsackievirus A., still more preferably, the Coxsackievirus is Coxsackievirus A21.

In a preferred form, the Picornavirus is an Echovirus. Preferably, the Echovirus is Echovirus 6, 7, 11, 12, 13 or 29.

In a preferred form, the Picornavirus is a Poliovirus. Preferably, the Poliovirus is Poliovirus type 1, 2 or 3.

In a preferred form, the Picornavirus is a Rhinovirus. Preferably, the Rhinovirus is a member of the major group of rhinoviruses or minor group of rhinoviruses.

In one preferred form, the Picornavirus is bioselected by passaging a Picornavirus not capable of lytically infecting a cell without ICAM-1 in a DAF-expressing cell line without ICAM-1 and recovering the selected Picornavirus which is capable of lytically infecting a cell without ICAM-1.

In another preferred form, the Picornavirus can be altered, mutated or modified by any known means such as site directed mutagensis or passage in a cell where access to ICAM-1 is blocked by use of and anti-ICAM-1 antibody.

Preferably, the selected Picornavirus has an alteration in one or more capsid proteins compared with wild-type virus. In Coxsackievirus for example, the capsid protein is selected from VP1, VP2 and VP3. More preferably, the mutation is selected from one or more of VP3 R96H; VP3 E101A; VP3 A239S; VP2 S164L and VP2 V209

Preferably, the cell is a neoplasm, more preferably the neoplasm a DAF-pressing neoplasm. Examples include, but not limited to, lung cancer, prostate cancer, colorectal cancer, thyroid cancer, renal cancer, adrenal cancer, liver cancer, leukemia, melanoma, pre-cancerous cells, oesophageal cancer, breast cancer, brain cancer, ovarian cancer, stomach and intestinal cancer.

In a second aspect, the present invention provides a nucleic acid molecule of an isolated Picornavirus capable of lytically infecting a cell substantially in the absence of intercellular adhesion molecule-1 (ICAM-1). In one embodiment the nucleic acid molecule may be derived from the Picornavirus and may be single stranded RNA or complementary DNA from the virus. Preferably the nucleic acid molecule comprises a nucleic acid sequence selected from the group consisting of SEQ ID NO:1, SEQ ID NO:3, SEQ ID NO:5, and SEQ ID NO:7.

In a third aspect, the present invention provides a method for bioselecting a Picornavirus capable of lytically infecting a cell substantially in the absence of intercellular adhesion molecule-1 (ICAM-1), the method comprising culturing a Picornavirus not capable of lytically infecting a cell substantially in the absence of intercellular adhesion molecule-1 (ICAM-1) in a suitable cell line for a sufficient number of passages and selecting a Picornavirus capable of lytically infecting a cell substantially in the absence of intercellular adhesion molecule-1 (ICAM-1).

Preferably the cell line is selected from human cancers such as rhabdomyosarcoma, lung cancer, prostate cancer, colorectal cancer, thyroid cancer, renal cancer, adrenal cancer, liver cancer, leukemia, melanoma, pre-cancerous cells, oesophageal cancer, breast cancer, brain cancer, ovarian cancer, stomach and intestinal cancer. More preferably, the cell line is a DAF-expressing cell line that does not express ICAM-1.

Typically, a sufficient number of passages is generally up to about 10. It will be appreciated, however, that passages from 1 to 100 or more can be used, depending on the Picornavirus and the cell type. In one embodiment 4 passages is used. In another embodiment 5 passages are used. In yet another embodiment 6, 7, or 8 passages may be used.

In a fourth aspect, the present invention provides a Picornavirus obtained from the method according to the third aspect of the present invention.

In a fifth aspect, the present invention provides a pharmaceutical composition containing an isolated Picornavirus according to the first or fourth aspects of the present invention together with a suitable pharmaceutically acceptable excipient or diluent.

In a sixth aspect, the present invention provides a pharmaceutical composition containing viral nucleic acid molecules or complementary DNA copies of the viral nucleic acid according to the second aspect of the present invention together with a suitable pharmaceutically acceptable excipient or diluent.

In a seventh aspect, the present invention provides a method for treating a neoplasm in a mammal suffering from the neoplasm, the method comprising administering to the mammal an effective amount of an isolated Picornavirus according to the first or fifth aspects of the present invention under conditions which result in virus-mediated oncolysis of the cells of the neoplasm.

Preferably, the neoplasm a DAF-expressing neoplasm. Examples include, but not limited to, lung cancer, prostate cancer, colorectal cancer, thyroid cancer, renal cancer, adrenal cancer, liver cancer, leukemia, melanoma, pre-cancerous cells, oesophageal cancer, breast cancer, brain cancer, ovarian cancer, stomach and intestinal cancer.

In a eighth aspect, the present invention provides a method for treating a neoplasm in a mammal suffering from the neoplasm, the method comprising administering to the mammal an effective amount of a nucleic acid molecule or complementary DNA copies of the viral nucleic acid according to the second aspect of the present invention or a pharmaceutical composition according to the sixth aspect of the present invention under conditions which result in virus-mediated oncolysis of the cells of the neoplasm.

Preferably, the neoplasm a DAF-expressing neoplasm. Examples include, but not limited to, lung cancer, prostate cancer, colorectal cancer, thyroid cancer, renal cancer, adrenal cancer, liver cancer, leukemia, melanoma, pre-cancerous cells, oesophageal cancer, breast cancer, brain cancer, and ovarian cancer.

In a ninth aspect, the present invention provides use of an isolated Picornavirus according to the first or fifth aspects of the present invention in a method of therapy or treatment.

In a tenth aspect, the present invention provides use of a nucleic acid molecule according to the second aspect of the present invention in a method of therapy or treatment.

In an eleventh aspect, the present invention provides an isolated selected Picornavirus in the form of CVA21-DAFv as defined herein, or modified or altered forms thereof.

In a twelfth aspect, the present invention provides the use of an isolated selected Picornavirus capable of lytically infecting or inducing apoptosis in a cell substantially in the absence of intercellular adhesion molecule-1 (ICAM-1), in the manufacture of a medicament for treatment of a neoplasm in a mammal. In a preferred embodiment there is provided the use of an inoculant for generating Picornavirus of the invention in the manufacture of a medicament for treating a neoplasm in a mammal with the Picornavirus such that at least some of the cells of the neoplasm are killed.

In a thirteenth aspect of the present invention there is provided an applicator for applying an inoculant to a mammal for generating virus to treat a neoplasm in the mammal, wherein the applicator comprises a region impregnated with the inoculant such that the inoculant may be brought into contact with the mammal, and the virus is an isolated selected Picornavirus capable of lytically infecting or inducing apoptosis in a cell substantially in the absence of intercellular adhesion molecule-1 (ICAM-1).

Samples of viruses described herein were deposited under the terms of the Budapest Treaty at the Australian Government Analytical Laboratories (National Measurement Institute, 1 Suakin Street (PO Box 385) Pymble NSW 2073 Australia. Isolates CVA21 #272101 (Accession No. NM05/43993), CVA21 #275238 (Accession No. NM05/43991), and CVA21 #272598 (Accession No. NM05/43992) were deposited on 14 Jan. 2005. CVA21-DAFv was deposited on 17 Jan. 2005 under Accession No. NM05143996.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of this application.

In order that the present invention may be more clearly understood, preferred forms will be described with reference to the following drawings and examples.

BRIEF DESCRIPTION OF THE DRAWINGS

FIG. 1. Binding of [$^{35}$S]-methionine labeled CVA21 prototype (Kuykendall) and three CVA21 clinical isolates (#272101, #275238, #272598) to (A) DAF expressing CHO cells and (B) ICAM-1 expressing CHO cells in the presence and absence of an anti-ICAM-1 MAb. Levels of [$^{35}$S]-methionine labeled virus bound was determined by liquid scintillation counting. Results are expressed as the means of triplicate samples+SD. Y-axis shows virus bound (cpm×10$^2$).

FIG. 2. Binding of [$^{35}$S]-methionine labeled CVA21 prototype Kuykendall (A) and clinical isolate #272101 (B) to HeLa cells in the presence of an anti-DAF SCR 1 MAb, an anti-ICAM-1 domain 1 MAb, and/or PI-PLC treatment. Levels of [$^{35}$S]-methionine labeled virus bound was determined by liquid scintillation counting. Results are expressed as the means of triplicate samples+SD. Y-axis shows virus bound (cpm×10$^2$).

FIG. 3. Binding of [$^{35}$S]-methionine labeled CVA21 prototype (Kuykendall) and three CVA21 clinical isolates (#272101, #275238, #272598) to CHO cells expressing either DAF or ICAM-1 alone or in combination. (A) Flow cytometric analysis of surface DAF and ICAM-1 expression. Transfected CHO cells were incubated with either conjugate alone, anti-DAF MAb (IH4) or anti-ICAM-1 MAb (WEHI) and the specific binding measured on a FACStar analyzer. The closed histograms represent the binding of the conjugate, the open histograms the binding of the anti-DAF MAb and the dotted histograms the binding of the anti-ICAM-IMab. (B) Levels of [$^{35}$S]-methionine labeled virus bound was determined by liquid scintillation counting. Results are expressed as the means of triplicate samples+SD. Y-axis shows virus bound (cpm× $10^2$).

FIG. 5. Multiple sequence alignments of the VP1 (residues 582-879 of SEQ ID NO: 81, VP2 (residues 70-341 of SEQ ID NO: 8) and VP3 (residues 342-581 of SEQ ID NO: 8) capsid proteins for the prototype CVA21 Kuykendall strain and clinical isolates #272101, #275238 and #272598. Amino acid changes in the clinical isolates relative to the Kuykendall strain are represented in bold type. Sequence alignments were generated using the Clustal X program. Individual amino acids that constitute the CVA21-ICAM-1 binding footprint are highlighted by closed boxes FIG. 6. Infection of SkMel28 and RD cells by CVA21 parental and CVA21-DAFv. (A) Flow cytometric analysis of ICAM-1 and DAF expression on RD and SkMel28 cells. The solid histogram represents binding of conjugate only, the dotted histogram represents binding of anti-ICAM-1 mAb, and binding of anti-DAF mAb is shown by the filled histogram. (B) Monolayers of SkMel28 and RD cells in 96-well plates were inoculated with 10-fold dilutions of CVA21 parental and CVA21-DAFv. Following incubation for 72 h, the monolayers were fixed and stained with a crystal violet solution. + indicates CPE detected by microscopical examination. (C) Representative plaque morphology of the CVA21 parental and CVA21-DAFv on SkMel28 cells as compared with the CVA21-DAF variant on RD cells. Cells were infected with serial dilutions of virus and overlaid with DMEM containing 0.7% agarose 1 h after infection. Plates were incubated at 37° C. and stained with crystal violet 48 h after infection.

FIG. 8. Elution of CVA21-DAFv from DAF. (A) Comparison of CVA21 parental and CVA21-DAFv binding stringency to surface DAF. CHO-DAF cells were incubated with radiolabeled virus for 2 h at 4° C. and cell-bound virus was then eluted with varying concentrations of anti-DAF SCR1 mAb (IA10) for 1 h on ice. The supernatant was monitored for level of eluted virus and the results are expressed as the % of cell eluted radiolabeled virus. (B) Sedimentation of DAF and ICAM-1 bound CVA21-DAFv virions. CHO-DAF and CHO-ICAM-1 cells were incubated with radiolabeled CVA21-DAFv virions for 2 h at 4° C. and cell-bound virus was allowed to elute for 2 h at 37° C. Sedimentation of eluted virions were analyzed on 5-30% sucrose gradients. Mature virions (160S) and provirions (125S) were used as internal migration controls.

FIG. 9. Inhibition of CVA21-DAFv lytic infection by anti-DAF SCR1 mAb and soluble DAF (sDAF). (A) Confluent monolayers of RD cells were incubated with anti-DAF SCR1 mAb IA10 prior to infection with CVA21-DAFV. Following incubation for 24 h at 37° C., the cells were inspected for cell lysis and photographed. (B) CVA21-DAFv was incubated with sDAF (85 µg/ml) for 1 h at 37° C. and added to RD cell monolayers. Following incubation for 48 h at 37° C., the cells were inspected for cell lysis and photographed.

FIG. 19. In vivo oncolysis of human prostate xenografts by CVA21-DAFv. SCID (severe combined immuno-deficient) mice bearing subcutaneous PC3 tumours (approximately 50-100 mm$^3$) growing on the flank after injection with 2×10$^6$ PC3 cells received intravenous injection with a single dose of CVA21 parental, CVA21-DAFv or PBS. The average tumour sizes were measured externally with callipers and the tumour volumes are estimated using the formula for a spheroid. Tumour volumes are expressed as the means of 6 treated mice +/−SE.

FIG. 20. Sequence of the Capsid coding region of the CVA21 #272598 isolate. (A) nucleotide sequence and (B) translated amino acid sequence, corresponding to SEQ ID NO:1 and SEQ ID NO:2, respectively.

FIG. 21. Sequence of the Capsid coding region of the CVA21 #275238 isolate. (A) nucleotide sequence and (B) translated amino acid sequence, corresponding to SEQ ID NO:3 and SEQ ID NO:4, respectively.

FIG. 22. Sequence of the Capsid coding region of the CVA21 #272101 isolate. (A) nucleotide sequence and (B) translated amino acid sequence, corresponding to SEQ ID NO:5 and SEQ ID NO:6, respectively.

FIG. 23. Sequence of the Capsid coding region of the CVA21-DAFv. (A) nucleotide sequence and (B) translated amino acid sequence, corresponding to SEQ ID NO:7 and SEQ ID NO:8, respectively.

MODE(S) FOR CARRYING OUT THE INVENTION

Figure 4:
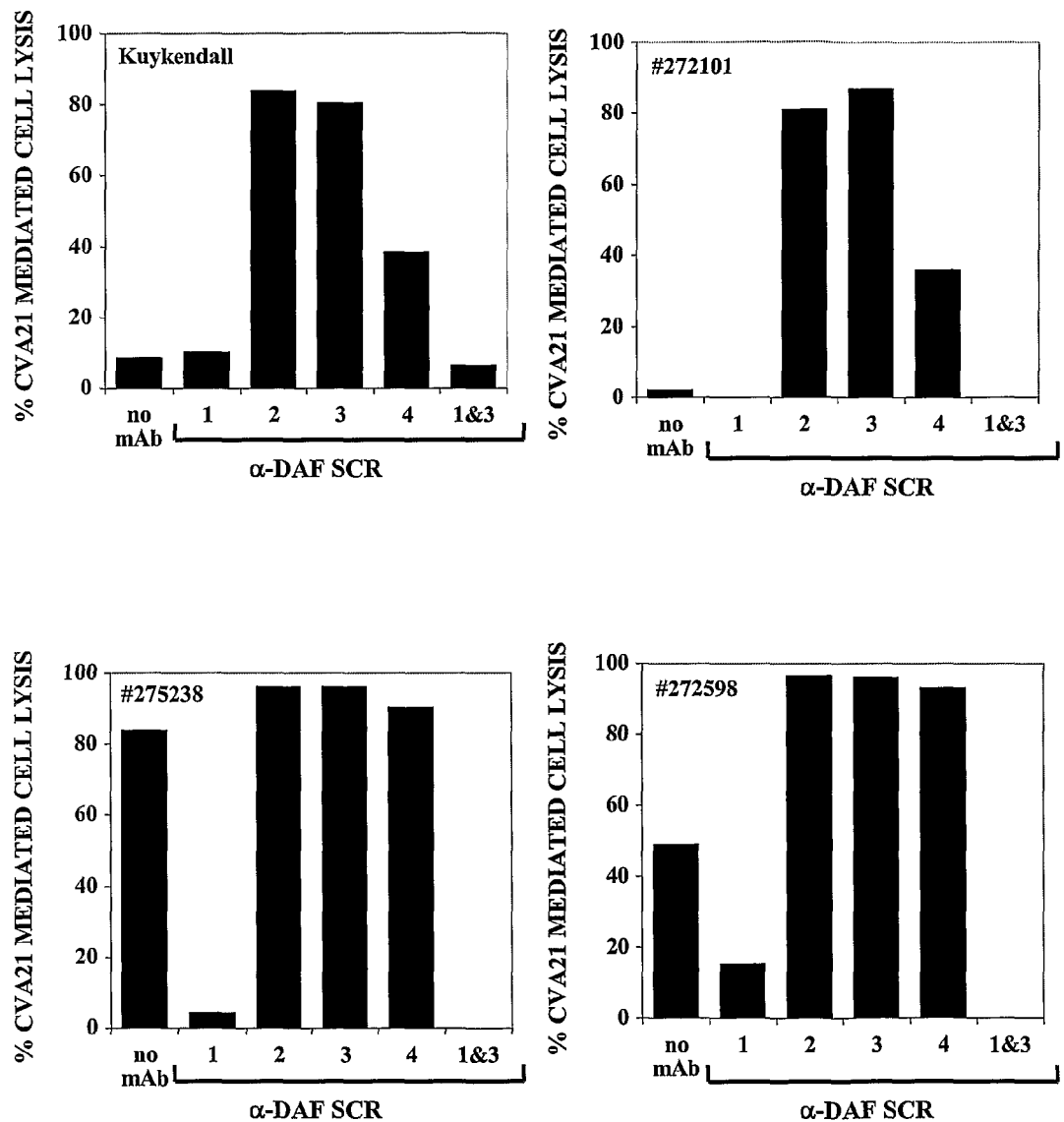
FIG. 4. Lytic infection of ICAM-1 negative RD cells by the CVA21 prototype (Kuykendall) and clinical isolates (#272101, #275238, #272598) in the presence of anti-DAF MAbs IA10 (SCR 1), VIIIA7 (SCR 2), IH4 (SCR 3), and IIH6 (SCR 4). Anti-DAF MAbs (20 µg/ml) were added to monolayers of RD cells cultured in 96-well plates. Following incubation for 1 h at 37° C. the cells were challenged with approximately $10^3$ TCID$_{50}$/well of the CVA21 isolates and incubated for 48 h at 37° C. Cell lysis was assessed by staining the cell monolayers with a crystal violet/methanol solution and then measuring the absorbance at 540 nm. Results are expressed as the mean percentage lysis of duplicate wells.

Although it is known that some naturally occurring Picornavirus and other viruses such as reoviruses are suitable for use in treatment of limited types of cancers, there is still a need to develop improved treatments. In order to expand the possible range of cancer treatment and provide even more efficacious treatments, the present inventors have obtained a new oncolytic Picornavirus with improved oncolytic properties by modification and bioselection.

As described herein, the present inventors have discovered that wild-type Picornavirus can be bioselected to lytically infect cells expressing DAF and not ICAM-1, such cells usually are resistant to wild-type Picornavirus infection. "Resistance" of cells to Picornavirus infection indicates that infection of the cells with the virus did not result in significant viral production or yield. Cells that are "susceptible" are those that demonstrate induction of cytopathic effects, viral protein synthesis, and/or virus production.

Based upon these discoveries, the present inventors have developed methods for obtaining new Picornavirus suitable for use in treating neoplasms in mammals. The mammal may be a human or an individual of any species of social, economic or research importance including, but not limited to, mice, dogs, cats, sheep, goats, cows, horses, pigs, non-human primates, and humans. In a preferred embodiment, the mammal is a human.

The Picornavirus may be naturally occurring or modified. The Picornavirus is "naturally-occurring" when it can be isolated from a source in nature and has not been intentionally modified by humans in the laboratory. For example, the Picornavirus can be obtained from a "field source": that is, from a human patient.

The Picornavirus may be modified but still capable of lytically infecting a mammalian cell expressing DAF and/or ICAM-1. The Picornavirus may be bioselected by culturing naturally-occurring Picornavirus in a cell line for a number of passages until a modified Picornavirus is obtained. Suitable cell lines include DAF-expressing cells such as cancer cell lines. It will be appreciated that other cell lines would also be suitable.

The Picornavirus may be chemically or biochemically pretreated (e.g., by treatment with a protease, such as chymotrypsin or trypsin) prior to administration to a subject's cells. Pretreatment with a protease removes the outer coat or capsid of the virus and may increase the infectivity of the virus. The Picornavirus may be coated in a liposome or micelle to reduce or prevent an immune response from a mammal which has developed immunity to the Picornavirus. For example, the virion may be treated with chymotrypsin in the presence of micelle forming concentrations of alkyl sulfate detergents to generate a new infectious subvirion particle.

The Picornavirus may be a recombinant Picornavirus from two or more types of Picornaviruses with differing pathogenic phenotypes such that it contains different antigenic determinants thereby reducing or preventing an immune response by a mammal previously exposed to a Picornavirus subtype. Such recombinant virions can be generated by co-infection of mammalian cells with different subtypes of Picornavirus with the resultant resorting and incorporation of different subtype coat proteins into the resulting virion capsids.

The Picornavirus may be modified by incorporation of mutated coat proteins, such as for example VP1, VP2 and VP3 into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in Picornavirus infected mammalian cells in vitro will result in the incorporation of the mutated protein into the Picornavirus virion particle.

The Picornavirus may also be modified to reduce or eliminate an immune reaction to the Picornavirus. Such modified Picornavirus are termed "immunoprotected Picornavirus". Such modifications could include packaging of the Picornavirus in a liposome, a micelle or other vehicle to mask the Picornavirus from the mammals immune system. Alternatively, the outer capsid of the Picornavirus virion particle may be removed or altered since the proteins present in the outer capsid are the major determinant of the host humoral and cellular responses.

In the methods of the invention, Picornavirus is administered to a neoplasm in the individual mammal. Representative types of human Picornavirus that can be used include enteroviruses, Coxsackievirus, Echovirus, Poliovirus, and unclassified enteroviruses, Rhinovirus, Paraechovirus, Hepatovirus, and Cardiovirus. In a preferred form, the Picornavirus is a Coxsackievirus. Preferably, the Coxsackievirus is type A, more preferably Coxsackievirus A21. A combination of different serotypes and/or different strains of Picornavirus, such as Picornavirus from different species of animal, can be used. The Picornavirus is "naturally-occurring": that is, it can be isolated from a source in nature and has not been intentionally modified by humans in the laboratory. For example, the Picornavirus can be bioselected from a "field source": that is, from a human patient. If desired, the Picornavirus can be chemically or biochemically pretreated (e.g., by treatment with a protease, such as chymotrypsin or trypsin) prior to administration to the neoplasm. Such pretreatment removes the outer coat of the virus and may thereby result in better infectivity of the virus.

The neoplasm can be a solid neoplasm (e.g., sarcoma or carcinoma), or a cancerous growth affecting the hematopoietic system (a "hematopoietic neoplasm"; e.g., lymphoma or leukemia). A neoplasm is an abnormal tissue growth, generally forming a distinct mass, that grows by cellular proliferation more rapidly than normal tissue growth. Neoplasms show partial or total lack of structural organization and functional coordination with normal tissue. As used herein, a "neoplasm", also referred to as a "tumor", is intended to encompass hematopoietic neoplasms as well as solid neoplasms. At least some of the cells of the neoplasm express DAF and/or ICAM-1. One neoplasm that is particularly susceptible to treatment by the methods of the invention is melamona. Other neoplasms that are particularly susceptible to treatment by the methods of the invention include breast cancer, brain cancer (e.g., glioblastoma), lung cancer, prostate cancer, colorectal cancer, thyroid cancer, renal cancer, adrenal cancer, liver cancer, leukemia, ovarian cancer, stomach and intestinal cancer, etc.

The Picornavirus is typically administered in a physiologically acceptable carrier or vehicle, such as phosphate-buffered saline, to the neoplasm. "Administration to a neoplasm" indicates that the Picornavirus is administered in a manner so that it contacts the cells of the neoplasm (also referred to herein as "neoplastic cells"). The route by which the Picornavirus is administered, as well as the formulation, carrier or vehicle, will depend on the location as well as the type of the neoplasm. A wide variety of administration routes can be employed. For example, for a solid neoplasm that is accessible, the Picornavirus can be administered by injection directly to the neoplasm. For a hematopoietic neoplasm, for example, the Picornavirus can be administered intravenously or intravascularly. For neoplasms that are not easily accessible within the body, such as metastases or brain tumors, the Picornavirus is administered in a manner such that it can be transported systemically through the body of the mammal and thereby reach the neoplasm (e.g., intrathecally, intravenously or intramuscularly). Alternatively, the Picornavirus can be administered directly to a single solid neoplasm, where it then is carried systemically through the body to metastases. The Picornavirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The Picornavirus or nucleic acid obtained from or derived from the Picornavirus is administered in an amount that is sufficient to treat the neoplasm (e.g., an "effective amount"). A neoplasm is "treated" when administration of Picornavirus to cells of the neoplasm effects oncolysis of the neoplastic cells, resulting in a reduction in size of the neoplasm, or in a complete elimination of the neoplasm. The reduction in size of the neoplasm, or preferably elimination of the neoplasm, is generally caused by lysis of neoplastic cells ("oncolysis") by the Picornavirus. The effective amount will be determined on an individual basis and may be based, at least in part, on consideration of the type of Picornavirus; the individual's size, age, gender; and the size and other characteristics of the neoplasm. For example, for treatment of a human, approximately $10^2$ to $10^{12}$ plaque forming units (PFU) of Picornavirus can be used, depending on the type, size and number of tumors present. Preferably the inoculant will contain greater than about $10^5$ PFU, for example between about $10^5$ to $10^6$ PFU or between about $10^6$ to $10^7$ PFU. More preferably the inoculant may contain between about $1 \times 10^6$ to about $5 \times 10^6$ PFU, such as about $3 \times 10^6$ PFU. For example, for the treatment of melanoma in a human, one or more inoculations of about $3 \times 10^6$ PFU may be used. The Picornavirus can be administered in a single dose, or multiple doses (i.e., more than one dose). The multiple doses can be administered concurrently, or consecutively (e.g., over a period of days or weeks). Typically, in therapeutic applications the treatment would be for the duration of the disease condition, for example at least until the neoplasm was no longer detectable by conventional means. It is also contemplated that it may be desirable to continue treatment for a period beyond the presence of detectable neoplasms, for example where the treating physician suspects that undetectable neoplasms may be present. The Picornavirus or nucleic acid can also be administered to more than one neoplasm in the same individual.

Where multiple administrations of Picornavirus are desired a different virus may be administered each time to avoid or minimise the effect of any immune response to a previously administered virus, and a course of treatment may extend for one to two weeks or more as may be determined by the attending physician. Most preferably, virus to which the mammal has not previously been exposed or to which the mammal generates a relatively minor immune response as may be determined by standard techniques may be administered.

The present invention includes an isolated nucleic acid molecule of a Picornavirus capable of lytically infecting a cell substantially in the absence of intercellular adhesion molecule-1 (ICAM-1). In one embodiment the nucleic acid molecule may be derived from the Picornavirus and may be single stranded RNA or complementary DNA from the virus. It will be appreciated that a nucleic acid sequence of the invention includes a nucleic acid sequence that has been derived from a Picornavirus including, for example, a nucleic acid sequence encoding the viral genome or a sufficient sequence thereof to permit generation of the virus or to be capable of eliciting a lytic infection in a cell. For example, the nucleic acid molecule may comprise a single viral RNA or DNA molecule, such as a complementary DNA molecule, or a plurality of such molecules encoding different viral sequences.

The term "polynucleotide" as used herein refers to a single- or double-stranded polymer of deoxyribonucleotide, ribonucleotide bases or known analogues or natural nucleotides, or mixtures thereof.

It is to be understood that in the context of the specification the term "derived" from thus includes that the sequence may be viral RNA directly isolated from a Picornavirus, synthetic RNA, cDNA corresponding to the isolated sequence. The term also includes synthetic polynucleotide sequences comprising one or more mutations in the sequence compared to wild-type sequence or parental sequence, including, for example mutations in the capsid proteins.

Any suitable method for isolation of viral RNA may be used, including methods based on the use of phenol/chloroform extraction, such as provided in commercial kit form for isolation of viral RNA, such as Trizol® LS reagent (GIBCO BRL, Life Technologies Grand Island, N.Y., USA), isolation methods which utilize magnetic bead-based isolation, such as Ambion MagMaX™ viral RNA isolation kits. Methods for the isolation of viral RNA are generally described in, for example Ausubel, F., et al., eds. Current Protocols in Molecular Biology. 1992, Green Publishing Associates and Wiley- Interscience, John Wiley and Sons: New York. and in Sambrook et al., (1989), Molecular Cloning: A Laboratory Manual, Second Ed., Cold Spring Harbour Laboratory Press, New York.

It will be appreciated that the invention does not require the nucleic acid sequence, such as viral RNA, whether it be directly isolated from virus, synthesized, presented as a plasmid molecule or generated in vitro such as from cDNA templates using bacteriophage T7 RNA polymerase, to be devoid of contaminant material, such as cell debris, to be considered "isolated" in the context of this specification. Thus, in the context of the specification RNA will be considered isolated when non-RNA components from the source material, such as cellular proteins, have been partially or completely removed from the RNA. For example, the RNA will be considered "isolated" when greater than 50% of non-RNA material has been removed. It is preferred that greater than 60% of the non-RNA material be removed, more preferably greater than 70%, 80% or 90% of the non-RNA material will be removed. Typically, the RNA will contain less than 10% contaminant material, more typically less than 5% contaminant material. Thus, the RNA will preferably be greater than 95% pure for viral RNA, even more preferably greater than 97% pure or greater than 99% pure.

Preferably the nucleic acid molecule comprises a nucleic acid sequence selected from the group consisting of SEQ ID NO:1, SEQ ID NO:3, SEQ ID NO:5, and SEQ ID NO:7. Those skilled in the art will recognise that, inview of the degeneracy of the genetic code considerable sequence variation is possible among these polynucleotide molecules.

The present invention also provides isolated polynucleotide sequences that are substantially similar to the polynucleotides disclosed herein, for example SEQ ID NO:1, SEQ ID NO:3, SEQ ID NO:5, and SEQ ID NO:7, where such sequences comprise or provide a Picornavirus the capability of lytically infecting a cell substantially in the absence of intercellular adhesion molecule-1 (ICAM-1). The polynucleotide sequence variants possess qualitative biological activity in common with one or more of the sequences of SEQ ID NO:1, SEQ ID NO:3, SEQ ID NO:5, and SEQ ID NO:7. The term "substantially similar" is used herein to denote sequences having at least about 60%, more preferably at least about 70%, even more preferably still at least about 80%, sequence identity to the sequences shown in any one of SEQ ID NO:1, SEQ ID NO:3, SEQ ID NO:5, and SEQ ID NO: 7. Typically, such sequences will more preferably be at least about 90% identical, and most preferably at least about 95% or more identical to any one of SEQ ID NO:1, SEQ ID NO:3, SEQ ID NO:5, and SEQ ID NO:7.

As used herein "sequence identity" refers to the residues in two sequences that are the same when aligned for maximum correspondence over a specified window of comparison by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453).

In addition to the above description of the sequences of the invention it will be appreciated that sequences of the invention include variant sequences such as, for the polypeptide sequences, sequences comprising one or more amino acid substitutions, deletions and/or alterations, such as conservative amino acid changes and, for the polynucleotide sequences, sequences encoding polypeptide sequences comprising one or more amino acid substitutions, deletions and/or alterations, such as one or more conservative amino acid changes. These changes are preferably of a minor nature, that is conservative amino acid substitutions and other substitutions that do not significantly affect the activity of the sequence, such as conferring a capability on a virus of lytically infecting a cell substantially in the absence of intercellular adhesion molecule-1 (ICAM-1). Conservative amino acid substitutions and methods for their introduction are known in the art and generally refer to substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. The following table may be used as a guide:

TABLE 1

Conservative Amino Acid Substitutions

| Basic | Arginine, Lysine, Histidine | Hydrophobic | Leucine, Isoleucine Valine |
|---|---|---|---|
| Acidic | Glutamic acid, Aspartic acid | Aromatic | Phenylalanine, Tryptophan, Tyrosine |
| Polar | Glutamine, Asparagine | Small | Glycine, Alanine, Serine, Threonine, Methionine |

Variant sequences include, for example conservative substitutions of the capsid protein alterations described herein. For example, it would be expected that a sequence comprising a conservative substitution of the mutant VP3 R96H, for example VP3 R96K may have the desired property. Similarly it would be expected that one or more sequences comprising a conservative substitution of the mutant VP3 E101A, for example VP3 E101G, VP3 E101T, VP3 E101S, or VP3 E101M may have the desired property. As a further example, it would be expected that one or more sequences comprising a conservative substitution of the mutant VP3 A239S, such as VP3 A239G, VP3 A239T or VP3 A239M may have the desired property. Still further by way of example, it would be expected that one or more sequences comprising a conservative substitution of the mutant VP2 S164L, such as VP2 S164I or VP2 S164V may have the desired property.

Variant sequences may be readily tested for functionality according to the invention as described herein.

It will also be appreciated that the Picornavirus can be indirectly administered by using the RNA genome or a complementary DNA copy of the genome. When administered, the Picornavirus will still be able to replicate in the cell and cause the desired lytic infection and killing.

Thus, rather than intact virus, viral or other plasmids or expression vectors incorporating nucleic acid for generation of the virus may be injected into the tumor for uptake by tumor cells and generation of intact virus within the cells for effecting the treatment. Suitable expression vectors include plasmids capable of expression of a DNA (eg genomic DNA or cDNA) insert encoding viral proteins necessary for generation of the virus. An expression vector will typically include transcriptional regulatory control sequences to which the inserted nucleic acid is operably linked. By "operably linked" is meant the nucleic acid insert is linked to the transcriptional regulatory control sequences for permitting transcription of the inserted sequence (s) without a shift in the reading frame of the insert. Such transcriptional regulatory control sequences include promoters for facilitating binding of RNA polymerase to initiate transcription, and expression control elements for enabling binding of ribosomes to transcribed mRNA.

More particularly, the term "regulatory control sequence" as used herein is to be taken to encompass any DNA that is involved in driving transcription and controlling (ie regulating) the level of transcription of a given DNA sequence. For example, a 5' regulatory control sequence is a DNA sequence located upstream of a coding sequence and which may comprise the promotor and the 5' untranslated leader sequence. A 3' regulatory control sequence is a DNA sequence located downstream of the coding sequence (s), which may comprise suitable transcription terminated (and/or) regulation signals, including one or more polyadenylation signals. As used herein, the term 'promotor' encompasses any DNA sequence which is recognised and bound (directly or indirectly) by a DNA-dependant RNA polymerase during initiation of transcription. A promotor includes the transcription initiation site, and binding sites for transcription initiation factors and RNA polymerase, and can comprise various other sites or sequences (eg enhances), to which gene expression regulatory proteins may bind.

Numerous expression vectors suitable for transfection of mammalian cells are known in the art. Expression vectors suitable for transfection of mammaliam cells include pSV2neo, pEF-PGk. puro, pTk2 and non-replicating adenoviral shuttle vectors incorporating the polyadenlation site and elongation factor 1-x promotor and pAdEasy based expression vectors most preferably incorporating a cytomegaloviros (CMV) promotor (eg see He et al, 1998). The plasmid pEFBOS which employs the polypeptide elongation factor—alpha 2 as the promotor may also be utilised. cDNA encoding the viral proteins necessary for generation of the virus may be prepared by reverse transcribing the viral RNA genome or fragments thereof and incorporated into a suitable vector utilising recombinant techniques well known in the act as described in for example Sambrook et al (1989), Molecular Cloning: A Laboratory Manual, Second Ed., Cold Spring Harbour Laboratory Press, New York, and Ausubel et al., (1994), Current Protocols in Molecular Biology, USA, Vol. 1 and 2.

Rather than cDNA, cells may be transfected with viral RNA extracted from purified virions or for instance RNA transcripts may be generated invitro from cDNA templates utilising bacteriophage T7 RNA polymerase as described in Ansardi, D. C., et al, 2001.

Similarly, a single plasmid or RNA molecule may be administered for expression of viral proteins and generation of virus, or a plurality of plasmids or RNA molecules encoding different ones of the viral proteins may be administered for transfecting the cells and generation of the virus.

Plasmids or RNA may be administered to tumors, for example either topically or by injection for uptake by the tumor cells in the absence of a carrier vehicle for facilitating transfection of the cells or in combination with such a vehicle. Suitable carrier vehicles include liposomes typically provided as an oil-in-water emulsion conventionally known in the art. Liposomes will typically comprise a combination of lipids, particularly phospholipids such as high phase transition temperature phospholipids usually with one or more steroids or steroid precursors such as cholesterol for providing membrane stability to the liposomes. Examples of lipids useful for providing liposomes include phosphatidyl compounds such as phosphatidylglycerol, phosphatidylcholine, phosphatidylserine, sphingolipids, phosphatidyethanolamine, cerebrosides and gangliosides. Diacyl phosphatidylglycerols are particularly suitable, where the lipid moiety contains from 14 to 18 carbon atoms and more preferably from 16 to 18 carbon atoms, and is saturated.

The Picornavirus or compositions comprising a Picornavirus may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Interaction of the liposomes with the target cells may be passive or active. Active targeting involves modification of the liposome by incorporating in the liposome membrane a specific ligand which binds or otherwise interacts with the corresponding ligand expressed by the target cells. Such ligands include for example a monoclonal antibody or binding fragment thereof (eg. an Fab or F (ab') 2) fragment, a sugar or glycolipid moiety, or a viral protein or monoclonal antibodies specific for DAF, are particularly preferred.

The Picornavirus may be administered in combination with other therapeutic agents. For example the Picornavirus may be administered with one or more different serotype(s) or strain(s) of Picornavirus. The additional serotype(s) or strain(s) of Picornavirus may have the same or different receptor requirements for cell infection as the Picornavirus of the invention.

As a further example the Picornavirus, or combination thereof, may be administered in combination with one or more agents capable of modulating or suppressing an immune response in the individual being treated. In this manner the natural immune response of the individual to viral infection may be altered, thereby preferably allowing a more efficacious viral infection and/or oncolytic outcome. Typically the agent capable of altering an immune response is an agent capable of suppressing an immune response. Agents capable of modulating or suppressing an immune response in an individual, such as a human individual, are described for example in The Merck Index, Thirteenth Edition, Merck & Co. Inc, Whitehouse Station, N.J., USA., the contents of which is incorporated herein by reference.

The Picornavirus, or combination thereof, may be used in combination with one or more chemotherapeutic agents, also referred to as antineoplastic agents. Antineoplastic agents are described for example in The Merck Index, Thirteenth Edition, Merck & Co. Inc, Whitehouse Station, N.J., USA. For example, the Picornavirus may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methortrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. The Picornavirus may be used in combination with one or more of bleomycin, vindesine, vincristine, dactamycin, procarbazine, lomustine or dacarbazine, for example for the treatment of melanoma. The Picornavirus may be used in combination with one or more of cisplatin and carboplatin, for example for the treatment of ovarian cancer. Further examples of chemotherapeutic agents that may be used in combination with the Picornavirus, for example for the treatment of breast cancer, include Cyclophosphamide (Cytoxan), methotrexate (Amethopterin, Mexate, Folex), and fluorouracil (Fluorouracil, 5-FU, Adrucil) [abbreviated CMF]; Cyclophosphamide, doxorubicin (Adriamycin), and fluorouracil [abbreviated CAF]; Doxorubicin (Adriamycin) and cyclophosphamide [abbreviated AC]; Doxorubicin (Adriamycin) and cyclophosphamide with paclitaxel (Taxol); Doxorubicin (Adriamycin), followed by CMF; Cyclophosphamide, epirubicin (Ellence), and fluorouracil. Other chemotherapy drugs used for treating women with breast cancer, for example, include docetaxel (Taxotere), vinorelbine (Navelbine), gemcitabine (Gemzar), and capecitabine (Xeloda).

It will be appreciated that use or administration of the Picornavirus "in combination" with one or more additional agents, such as one or more additional Picornaviruses, one or more agents capable of modulating or stimulating an immune response, or one or more antineoplastic agents, means use or administration in any manner in which the Picornavirus and additional agent(s) have therapeutic effect, such as an overlapping temporal effect. The members of the combination may be administered simultaneously or individually in any order that provides a desired therapeutic effect. When contemplated for combination therapy the Picornavirus and additional agent(s) may be in physical admixture or supplied separately, such as in kit form with or without instructions for administration. Kits according to the present invention may also include other components required to conduct the methods of the present invention, such as buffers and/or diluents. The kits typically include containers for housing the various components and instructions for using the kit components in the methods of the present invention.

It will be appreciated that pharmaceutical compositions of the invention include compositions of the Picornavirus in physical admixture with one or more additional therapeutic agent(s), as well as compositions comprising a Picornavirus as the only therapeutically active agent.

It will also be appreciated that, in the methods of the invention, the Picornavirus may be used in conjunction with other methods for treatment of neoplasms, such as surgical debulking or excision of the neoplasm and/or chemotherapy and/or radiotherapy. For example, where a treatment of a solid neoplasm is desired, the Picornovirus may be used as an adjunct to surgical debulking or excision of the neoplasm.

As used herein, an "isolated" virus is a virus which has been removed from, or from which has been removed, some or all of the components with which it would be found, whether it be a naturally occurring virus or a virus intentionally or unintentionally modified by humans. Such components may be referred to as contaminant components. It will be appreciated that an "isolated" virus need not be a pure preparation of virus in the sense that all contaminant components have been removed. Thus, virus will be considered "isolated" when non-viral components have been partially or completely removed from the virus. For example the virus will be considered "isolated" when greater than approximately 50% of contaminant material has been removed. It is preferred that greater than approximately 60% of contaminant material be removed, more preferably greater than approximately 70% of contaminant material is removed. Typically, the isolated virus has greater than approximately 80% or greater than approximately 90% of contaminant material removed. More typically, greater than approximately 95%, or approximately 97% of contaminant material is removed. In one embodiment greater than 99% of contaminant material is removed.

As used herein, "substantially in the absence of ICAM-1" when used in reference to a cell means that the cell expresses minimal or no ICAM-1. In particular, it will be understood that such a cell expresses insufficient ICAM-1 to provide the basis for a lytic infection of the cell by a virus which requires the presence of ICAM-1 for infection.

As used herein, "contacting" a cell with a virus refers to placing the virus in the culture of the cell such that the virus has the opportunity to make a contact with the cell, which may lead to successful infection by the virus or the induction of cell death by apoptosis.

As used herein, "viral infection" refers to the entry of a virus into a cell and the subsequent replication of the virus in the cell or the induction of cell death by apoptosis.

As used herein, "multiplicity of infection" refers to the ratio of the number of virus to the number of cells when a virus is used to contact cells.

As used herein, "cell lysis" refers to the disruption of cell membrane of a cell and the subsequent release of all or part of the content of the cell or the induction of cell death by apoptosis.

As used herein, "complete lysis" refers to the lysis of every cell in a culture of multiple cells.

As used herein, "culture conditions" refer to the conditions used in a cell culture, including but not limited to the temperature, type of culture containers, humidity, concentration of $CO_2$ or any other gas used in the culture containers, type of the culture medium, the initial density of the cultured cells, and if the cells are infected with a virus, the initial multiplicity of infection.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore.

As used herein, a cell is "disrupted" when the cell membrane is ruptured and at least some of the cell content is released from the cell. A cell may be disrupted, for example, by freeze-thawing, sonication or detergent treatments.

As used herein, "harvest" the virus refers to the act of collecting the produced virus from a cell culture which has been previously infected with the virus. Harvesting of the virus may involve breaking up the host cell if the virus is still cell associated. Alternatively but less preferably, viral particles which have been released into the culture media can be harvested from the media.

As used herein, "cytopathic effect" is indicated by the cells becoming swollen and granular in appearance and the cell membrane becomes disrupted. The cells which show a cytopathic effect stain negative in a viable cell count because they will take up the staining dye or the degradation of cellular DNA.

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture", which is a culture in which the culture medium is stirred continuously during the culture process.

As used herein, "viability of the cells" or "percentage of cells remaining viable" is the percentage of the cells which do not show a cytopathic effect in a population.

As used herein, "harvest time" refers to the time point at which the Picornavirus is collected and purified. The virus is preferably harvested when titer is sufficiently high and the virus is still cell-associated. Although the virus may be harvested even after complete cell lysis has occurred, it is desirable to harvest the virus before it is released from the cells to simplify the purification process. Thus, viability of the cells is routinely measured as an indication of whether the virus is still cell-associated. The virus is generally harvested when at least 5% of the cells are viable. Preferably, the virus is harvested when 20-95% of the cells are viable, more preferably when 35-90% cells remain viable, and most preferably when 50-80% cells remain viable.

In order that the present invention may be more clearly understood preferred forms will be described with reference to the following examples and drawings, which should not be construed as limiting the scope of the invention.

Materials and Methods
Cells and Viruses

Coxsackievirus A21 (CVA21) prototype strain Kuykendall and the three clinical isolates (#272101, #272598 and #275238) were obtained from Dr Margery Kennett, Entero-respiratory Laboratory, Fairfield Hospital, Melbourne, Victoria, Australia. Isolate #272101 was obtained from a 26 year old male infected with HIV, isolate #275238 from an 3 month old baby deceased due to Sudden Infant Death Syndrome and isolate #272598 from an 8 year old boy suffering an acute episode of croup. The clinical CVA21 isolates were passaged approximately three times in HeLa cells and/or human lung fibroblasts or HeLa-T cells and once in ICAM-1 expressing rhabdomyosarcoma (RD) cells (RD-ICAM-1) (Shafren, D. R., D. J. Dorahy, R. A. Ingham, G. F. Burns, and R. D. Barry. 1997. Coxsackievirus A21 binds to decay-accelerating factor but requires intercellular adhesion molecule 1 for cell entry. J. Virol. 71:4736-4743). The prototype strain of CVA21 was passaged approximately ten times in HeLa and/or human lung fibroblasts or HeLa-T cells and 3-4 times in RD-ICAM-1 cells.

The CVA21 prototype strain (Kuykendall, GenBank accession number AF465515) was obtained from Dr Margery Kennett and double-plaque purified in SkMel28 cells (herein designated CVA21 parental). CVA21-DAFv was bioselected to grow in ICAM-1 negative cells by serial passage in RD cells as described herein. Virus for the in vivo study was prepared in monolayers of SkMel28 (CVA21 parental) or RD cells (CVA21-DAFv) and purified by velocity centrifugation in 5-30% sucrose gradients as described previously, and the peak fractions were pooled, dialyzed against PBS and stored at −80° C. Titers of viral stocks (CVA21 parental and CVA21-DAFv) were determined on SkMel28 cells using the endpoint method of Reed and Muench.

HeLa cells were obtained from the American Type Culture Collection, Manassas, Va., USA; while, the Chinese Hamster Ovary (CHO) cells were obtained from Dr Bruce Loveland, Austin Research Institute, Heidelberg, Victoria, Australia.

Human melanoma cell line SkMel28 was obtained from Dr. S. J. Ralph (Department of Biochemistry and Molecular Biology, Monash University, Victoria, Australia); Rhabdomyosarcoma (RD) cells were obtained from Dr Margery Kennett (Entero-respiratory Laboratory, Fairfield Hospital, Melbourne, Victoria, Australia); Chinese Hamster Ovary (CHO) cells were obtained from Dr Bruce Loveland (Austin Research Institute, Heidelberg, Victoria, Australia); ovarian cancerous cell line DOV13 were obtained from Dr Ian Campbell (Peter MacCallum Cancer Centre, Melbourne, Australia). CHO cells stably expressing ICAM-1 or DAF (CHO-DAF and CHO-ICAM-1 cells). CVA21 prototype strain (Kuykendall, GenBank accession number AF465515) was obtained from Dr Margery Kennett and propagated in SkMel28 cells.

Human breast cancer cell lines (MDA-MB157, MDA-MB453, ZR-75-1), epithelial ovarian cancer cell lines (OVHS-1, OAW-42, DOV13) and the immortalized normal human ovarian surface epithelial cell line (HOSE) were obtained from the Peter MacCallum Cancer Centre (Melbourne, Australia); The human prostate cell lines (PC3 and DU145) were obtained from the Garvan Institute, Sydney, Australia and LNCaP cells were obtained from Elizabeth Williams, Bernard O'Brien Institute of Microsurgery, Melbourne, Australia; Human colorectal cancer cell lines (HCTI 16, SW620) were obtained from Peter MacCallum Cancer Centre, HT-29 were obtained from John Hunter Hospital (Newcastle, Australia)

Antibodies

The anti-ICAM-1 MAb WEHI specific for the first domain of ICAM-1 (Berendt, A. R., A. McDowell, A. G. Craig, P. A. Bates, M. J. E. Sternberg, K. Marsh, C. I. Newbold, and N. Hogg. 1992. The binding site on ICAM-1 for *Plasmodium falciparum*-infected erythrocytes overlaps, but is distinct from the LFA-1 binding site. Cell 68:71-81) was supplied by Dr Andrew Boyd, Queensland Institute of Medical Research, Queensland, Australia. Anti-DAF MAb IA10 (IgG2a) recognizes the first short consensus repeat (SCR) of DAF, VIIIA7 (IgG1) recognizes the third SCR and parts of the second SCR (Kinoshita, T., M. E. Medof, R. Silber, and V. Nussenzweig. 1985. Distribution of decay accelerating factor in the peripheral blood of normal individuals and patients with paroxysmal nocturnal hemoglobinuria. J. Exp. Med. 162:75-92), IH4 (IgG1) recognizes the third SCR of DAF (Coyne, K. E., E. S. Hall, M. A. Thompson, M. A. Arce, T. Kinoshoita, T. Fujita, D. J. Anstee, W. Rosse, and D. M. Lublin. 1992. Mapping of epitopes, glycosylation sites, and complement regulatory domains in human decay accelerating factor. J. Immunol. 149:2906-2913), while IIH6 (IgG1) recognizes the fourth SCR (Kinoshita, T., M. E. Medof, R. Silber, and V. Nussenzweig. 1985. Distribution of decay accelerating factor in the peripheral blood of normal individuals and patients with paroxysmal nocturnal hemoglobinuria. J. Exp. Med. 162:75-92). MAbs IA10, VIIIA7 and IIH6 were gifts from Dr Taroh Kinoshita, Department of Immunoregulation, Osaka University, Osaka, Japan. MAb IH4 was a gift from Dr Bruce Loveland, Austin Research Institute, Heidelberg, Victoria, Australia.

The anti-DAF mAb IH4, specific for SCR3 of DAF (Coyne, K. E., S. E. Hall, S. Thompson, M. A. Arce, T. Kinoshita, T. Fujita, D. J. Anstee, W. Rosse, and D. M. Lublin. 1992. Mapping of epitopes, glycosylation sites, and complement regulatory domains in human decay accelerating factor.

J Immunol. 149:2906-2913) and human recombinant soluble DAF (sDAF), were gifts from Dr Bruce Loveland; anti-DAF mAb IA10 directed against SCR1 was a generous gift from Dr Taroh Kinoshita (Department of Immunoregulation, Osaka University, Osaka, Japan); The anti-ICAM-1 WEHI mAb is directed against the N-terminal domain of ICAM-1 (Hoover-Litty, H., and J. M. Greve. 1993. Formation of rhinovirus-soluble ICAM-1 complexes and conformational changes in the virion. J Virol. 67:390-397) and was supplied by Dr Andrew Boyd (Queensland Institute for Medical Research, Queensland, Australia).

Viral Purification and Radiolabeled Binding Assays Confluent monolayers of RD-ICAM-1 cells in 6-well tissue culture plates were inoculated with 500 µl of the appropriate strain of CVA21 ($1\times10^5$ $TCID_{50}$/ml) for 1 h at 37° C. Unbound virus was removed by washing three times with methionine/cysteine free DMEM (ICN Biochemicals, Aurora, Ohio, USA), and following the addition of methionine/cysteine free DMEM, cell monolayers were incubated for a further 2 h before addition of 300 µCi of [$^{35}$S]-methionine/cysteine Trans-Label (ICN Radiochemicals, Irvine, Calif., USA). Infected monolayers were then incubated at 37° C. in a 5% $CO_2$ environment for 12 h. Following three freeze/thaw cycles viral lysates were purified in 5-30% sucrose gradients (Shafren, D. R., R. C. Bates, M. V. Agrez, R. L. Herd, G. F. Burns, and R. D. Barry. 1995. Coxsackieviruses B1, B3 and B5 use decay accelerating factor as a receptor for cell attachment. J. Virol. 9:3873-3877). Fractions were collected from the bottom of each tube and monitored by liquid scintillation counting on a 1450 Microbeta TRILUX (Wallac, Turku, Finland) to locate the 160S peak fractions to be used in radiolabeled virus binding assays.

Radiolabeled viral binding assays using HeLa cells were performed in 24-well tissue culture plates (Shafren et al 1995). Viral binding assays of transfected CHO cells were performed using cell suspensions. Approximately $1\times10^6$ cells in 800 µl of DMEM containing 1% bovine serum albumin (BSA) were incubated in the presence of 300 µl (approximately $1\times10^5$ CPM) of [$^{35}$S]-methionine labeled virus for 2 h at room temperature. Cells were then washed four times with serum-free DMEM dissolved in 200 µl of 0.2 M NaOH-1% sodium dodecyl sulfate (SDS) before the amount of [$^{35}$S]-methionine labeled virus bound was determined by liquid scintillation counting. When required, cells were pre-incubated with 20 µg/ml of anti-DAF or anti-ICAM-1 MAbs or phosphatidylinositol-specific phospholipase C (PI-PLC) (Sigma Chemicals, Sydney, New South Wales, Australia) (1.0 U per $5\times10^6$ cells) (Davitz, M. A., M. G. Low, and V. Nussenzweig. 1986. Release of decay-accelerating factor (DAF) from the cell membrane by phosphatidylinositol-specific phospholipase C (PI-PLC). Selective modification of a complement regulatory protein. J. Exp. Med. 163:1150-1161) for 1 h at 37° C. prior to addition of radiolabeled virus.

Virus Infectivity Assays

RD and RD-ICAM-1 cell monolayers in 96-well tissue culture plates were inoculated with 10-fold serial dilutions (100 µl/well in quadruplicate) of CVA21 in DMEM containing 1% fetal calf serum (FCS) and incubated at 37° C. in a 5% $CO_2$ environment for 48 h. Cell survival was quantitated by staining inoculated monolayers with 100 µl/well of a crystal violet/methanol solution (0.1% crystal violet, 20% methanol, 4.0% formaldehyde in PBS) for 24 h. Following washing in distilled water, the relative absorbance of the stained cell monolayer was read on a multiscan enzyme-linked immunosorbent assay plate reader (Flow Laboratories, McLean, Va., USA) at 540 nm. Fifty percent end point titers were calculated using the method of Reed and Muench (Reed, L. J., and H. A. Muench. 1938. A simple method of estimating fifty percent endpoints. Am. J. Hyg. 27:493-497) by scoring wells as positive if the absorbance values were less than three standard deviations (SD) of the control no virus wells.

Where cell monolayer pre-treatment with anti-receptor MAb was required, cells were incubated in the presence of MAb (1 µg/ml) for 1 h at 37° C. Cell monolayers were then inoculated with quadruplicate samples of the appropriate virus and incubated at 37° C. in a 5% $CO_2$ environment for 48 h before staining as described above.

Cell Transfection

CHO and RD cells were transfected to express ICAM-1 and/or DAF as described previously (Shafren, D. R., D. J. Dorahy, S. J. Greive, G. F. Burns, and R. D. Barry. 1997. Mouse cells expressing human intercellular adhesion molecule-1 are susceptible to infection by coxsackievirus A21. J. Virol. 71:785-789). Briefly, 500 µl aliquots of cells ($5\times10^6$ to $1\times10^7$ cells/ml) were resuspended in electroporation buffer (20 mM HEPES, 137 mM NaCl, 5 mM KCl, 0.7 mM $Na_2PO_4$, 6 mM glucose, pH 7.05) and mixed with 75 µg of pEF-BOS (Mizushima, S., and S. Nagata. 1990. pEF-BOS, a powerful mammalian expression vector. Nucl. Acid. Res. 18:5322) encoding DAF or ICAM-1 and 5 µg of pcDNA.neo in electroporation cuvettes (Bio-Rad, Richmond, Calif., USA). Cells were pulsed at 300 V and 250 µF with a Bio-Rad gene pulser, then seeded in tissue culture flasks and incubated at 37° C. for 48 h until the formation of confluent monolayers. Receptor expressing transfected cells were selected in DMEM containing G-418 (400 µg/ml), and further enriched by fluorescence activated cell sorting using the appropriate anti-receptor MAbs.

Flow Cytometry

DAF and ICAM-1 surface expression on transfected cells was analyzed by flow cytometry. Briefly, dispersed cells ($1\times10^6$) were incubated on ice with the appropriate MAbs (5 µg/ml in PBS) for 20 min. Cells were then washed with PBS, pelleted at 1000×g for 5 min and resuspended in 100 µl R-phycoerythrin-conjugated F(ab')$_2$ fragment of goat anti-mouse immunoglobulin diluted in PBS (DAKO A/S, Denmark) and incubated on ice for 20 min. Cells were washed and pelleted as above, resuspended in PBS and analyzed for DAF and ICAM-1 expression with a FACStar analyzer (Becton Dickenson, Sydney, Australia).

Dispersed cells ($1\times10^6$) were incubated on ice with anti-DAF IH4 or anti-ICAM-1 mAbs (5 µg/ml, diluted in phosphate buffered saline [PBS]) for 20 min. Cells were then washed with PBS, pelleted at 1000×g for 5 min and resuspended in 100 µl R-phycoerythrin-conjugated F(ab')$_2$ fragment of goat anti-mouse immunoglobulin diluted 1:100 in PBS (DAKO A/S, Denmark) and incubated on ice for 20 min. Cells were washed and pelleted as above, resuspended in PBS and analyzed for DAF and ICAM-1 expression using a FACStar analyzer (Becton Dickenson, Sydney, Australia).

Viral RNA Sequence Analysis

CVA21 isolates were propagated in confluent monolayers of RD-ICAM-1 cells. Viral cell lysates were pre-cleared by low speed centrifugation and virions in the supernatant pelleted by ultracentrifugation in SW 41 Ti rotor for 3 h at 40,000 rpm at 4° C. Viral pellets were resuspended in TE buffer (10 mM Tris-HCl, 1 mM EDTA, pH 7.5) and RNA was isolated from each strain using TRIZOL Ls Reagent (Gibco BRL Life Technologies) and the P1 region of the genomes were amplified by using a previously described long distance strategy (Lindberg, A. M., C. Polacek, and S. Johansson. 1997. Amplification and cloning of complete enterovirus genomes by long distance PCR. J. Virol. Meth. 65:191-199). The nucleotide sequences of the CVA21 P1 region, were determined from purified PCR amplicons using a primer walking strategy and employing a ABI Prism BigDye™ terminator cycle sequencing ready reaction kit (PE Biosystems, Sweden) (Lindberg et al 1997) as per the manufacturer's instructions. Nucleotide sequence alignments were generated using the Clustal X program (Thompson, J. D., D. G. Higgins, and T. J. Gobson. 1994. Clustal_W—improving the sensitivity of progressive multiple sequence alignment through sequence weighting, position-specific gap penalties and weight matrix choice. Nucleic Acids Res. 22:4673-4680).

Nucleotide Accession Numbers

The nucleotide sequences of the P1 region (capsid coding region) of CVA21 clinical isolates #272101, #275238 and #272598 described in this study have been submitted to Genbank and assigned accession numbers AY319942, AY319943 and AY319944, respectively Molecular Characterization and Structural Modeling of Viruses Viral RNA was extracted from the CVA21 parental and CVA21-DAFv strains using the QIAamp viral RNA mini kit and the capsid-coding region was amplified with one-step RT-PCR (Qiagen OneStep RT-PCR Kit) as per manufacturer's instructions using CVA21 specific primers. The nucleotide sequences were determined using purified PCR products (QIAquick Gel Extraction kit, QIAGEN GmbH) in a cycle sequencing reaction using ABI Prism BigDye™ terminator cycle sequencing ready reaction kit (PE Biosystems) as per the manufacturer's instructions.

The model of the CVA21 major structural proteins (VP1-3) was built with the program Modeller in a DEC alpha station, in a manner similar as used for the prediction of the poliovirus receptor structure. The CVA21 parental sequence was aligned against homologous enteroviral capsid proteins, for which the molecular structures have previously been determined and contain sequence identities above 50%, which include poliovirus 1, EV1, EV11, CVB3, CVA9 and swine vesicular disease virus (PDB code 1AR7, 1EV1, 1H8T, 1COV, 1D4M, and 1OOP, respectively) with alignment created by FASTA. The positions of ICAM-1 and DAF to the CVA21-DAFv capsid were aligned according to their ligand contact with human rhinovirus 3 and EV12, respectively.

Virus Infectivity Assay

Confluent cell monolayers in 96-well plates were inoculated with 100 µl 10-fold serial dilution of virus and incubated at 37° C. for 72 h. To quantitate cell survival, plates were microscopically examined before fixation with a crystal violet/methanol solution. Fifty percent end point titers were calculated using the method of Reed and Muench (Reed, L. J., and H. A. Muench. 1938. A simple method of estimating fifty percent endpoints. Am. J. Hyg. 27:493-497). For assessing mAb effect of virus-mediated cell lysis, cell monolayers were incubated with 50 µl anti-DAF SCR3 IH4 (5 µg/ml) mAb for 1 h at 37° C. prior to addition of virus and quantitation of cell lysis as above. For cell lysis assay with anti-DAF SCR1 mAb blockade, monolayers of RD cells in 6-well plates were pretreated with anti-DAF SCR1 mAb (15 µg/ml) prior to challenge with virus ($10^6$ $TCID_{50}$). Following incubation for 1 h at 37° C., unbound virus was removed and the monolayers were overlaid with Dulbecco's Modified Eagle's Media (DMEM). Inhibition of anti-DAF SCR1 mAb was assessed studying viral yields by titration on SkMel28 cells.

Radiolabelled Virus Binding Assays

The parental and CVA21-DAFv strains were radiolabeled with $^{35}$S-methionine in SkMel28 and RD cells, respectively, and purified on 5-30% sucrose gradients. Dispersed cells ($1\times10^6$) were preincubated with mAbs (20 µg/ml diluted in DMEM containing 1% bovine serum albumin [BSA]) for 1 h at room temperature and then incubated with $^{35}$S-labelled sucrose purified virus ($5\times10^5$ cpm) in DMEM containing 2% fetal calf serum (FCS) for 1 h at room temperature. Following three washes with DMEM-2% FCS, the amount of $^{35}$S-methionine labeled virus bound was measured by liquid scintillation counting on a 1450 Microbeta TRILUX (Wallac, Turku, Finland).

Sedimentation of DAF and ICAM-1 Bound Virions

Purified radiolabeled 160S CVA21-DAFv virions ($2.5\times10^6$ cpm) were incubated with CHO-DAF or CHO-ICAM-1 cells ($2\times10^7$) in DMEM-1% BSA for 2 h at 4° C. Unbound virions were removed by four washes with DMEM-2% FCS and cell-bound virions were permitted to elute for 2 h at 37° C. The cells were removed by centrifugation and the eluted virions were layered on 5-30% sucrose gradients and centrifuged for 95 min at 4° C. in an SW41Ti rotor at 36,000 rpm. Fractions (~700 µl) were collected from the bottom of the gradient and radioactivity was determined by liquid scintillation counting.

Elution of Cell-Bound Virus by Anti-DAF mAb

CHO-DAF cells ($3\times10^6$) were incubated at 4° C. for 2 h with radiolabeled virus ($4\times10^5$ cpm). Unbound virions were removed by four washes with ice-cold DMEM-2% FCS, cells were resuspended in 100 µl DMEM-2% FCS and incubated with varying concentrations (0-50 µg/ml) of anti-DAF SCR1 mAb (IA10). Following mAb competition for 1 h on ice, the cells were pelleted. The supernatant was harvested and monitored for level of eluted virus and the results are expressed as the percentage of cell eluted radiolabeled virus.

Neutralization of Virus with Soluble DAF

Human recombinant sDAF (85 µg/ml, diluted in PBS) was incubated with 1,000 50% tissue culture infectious doses ($TCID_{50}$) of CVA21-DAFv. After incubation at 37° C. for 1 h, the virus-DAF mixtures were applied to monolayers of RD cells in a 96-well plate and further incubated for 48 h.

CVA21-DAFV Therapy of Prostate Tumor Xenografts

SCID mice were housed in pathogen-free conditions according to a protocol approved by the University of Newcastle Animal Care and Ethics Committee. PC3 cells were grown in vitro, harvested, washed twice with PBS, and resuspended in sterile PBS. More than 95% of cells used for xenotransplantation were viable as assessed by trypan blue staining. Prior to xenotransplantation, animals were anaesthetized with 3% isofluorane. Tumor cells were xenografted into the flanks of anaesthetized 7 weeks old SCID mice by subcutaneous injections of $2\times10^6$ PC3 cells on the flank. Xenograft growth was monitored daily and measured with calipers. Estimates of tumor volumes were calculated using the formula for a spheroid. Once palpable tumors had been established (50-100 mm$^3$), the PC3 tumors were administered CVA21 parental, CVA21-DAFv ($3\times10^7$ TCID50) or PBS by intravenous injection and monitored for a period of 42 days. Viral titers in the serum were monitored by viral infectivity assay.

Results

I. Enterovirus Capsid Interations

Clinical Strains of CVA21 Bind to DAF and ICAM-1

To determine whether clinical isolates of CVA21 bind to DAF and ICAM-1 in a manner that is either similar or different to that of the prototype Kuykendall strain, CHO cells stably transfected to express either DAF or ICAM-1 were used in radiolabeled viral binding assays. No significant binding to CHO cells in the absence of DAF or ICAM-1 was observed for any of the CVA21 isolates (FIG. 1). All of the CVA21 strains bound to CHO cells expressing DAF (FIG. 1A), an interaction previously demonstrated for the prototype CVA21 Kuykendall strain. As expected, all clinical CVA21 isolates also bound to ICAM-1 expressed on the surface of CHO cells (FIG. 1B). Confirmation of the specificity of the CVA21/ICAM-1 interaction was verified by the action of an anti-ICAM-1 domain 1 specific MAb which completely abolished viral binding to ICAM-1 (FIG. 1B). Overall, these results confirm that clinical isolates of CVA21 bind to two separate cellular receptors, DAF and ICAM-1 in a similar manner to the prototype strain.

To further characterize the interaction of clinical isolates of CVA21 with DAF/ICAM-1, CVA21 viral binding assays were undertaken on HeLa cells ubiquitously co-expressing DAF and ICAM-1. CVA21 binding was assessed by MAb blockade of individual receptors or MAb blockade in combination (FIG. 2). The cellular attachment of the prototype Kuykendall strain (FIG. 2A) was compared to that of clinical CVA21 isolate #272101 (FIG. 2B) and both exhibited high level binding to HeLa cells in the absence of MAbs receptor blockade (FIG. 2). Specific MAb blockade of DAF SCR 1 partially blocked viral binding, however, it was unable to completely abolish viral attachment due to interaction with ICAM-1. When access to ICAM-1 was inhibited by MAb blockade, viral binding was reduced, more so for the clinical isolate #272101 (FIG. 2B) than the prototype, but not completely inhibited due to alternate viral attachment to DAF. The specificity of the clinical and prototype strains of CVA21 for the N-terminal domains of the DAF and ICAM-1 was demonstrated by the capacity of anti-DAF SCR1 and anti-ICAM-1 domain 1 MAbs to inhibit viral attachment to the same degree as pre-treating the cells with a combination of phosphatidylinositol-specific phospholipase-C (which cleaves GPI-linked proteins), and an anti-ICAM-1 MAb. Taken together, these results confirm that clinical isolate #272101, similar to the prototype strain, binds to the first SCR of DAF and the N-terminal domain of ICAM-1.

CVA21 Binding to DAF and ICAM-1 is Not Additive

The capacity of the CVA21 clinical isolates to bind either DAF or ICAM-1 alone or in combination was assessed to determine whether the presence of both receptors on the surface of a host cell contributed to additive virion cell attachment. To address this question, CHO cells were transfected to express either DAF or ICAM-1 alone or in combination. Flow cytometric analysis revealed comparable levels of DAF or ICAM-1 expression on cells expressing either receptor alone or in combination (FIG. 3A). Minimal levels of background binding to CHO cells were observed for all CVA21 strains. Significant levels of binding to individually expressed DAF or ICAM-1 were exhibited by all strains CVA21 (FIG. 3B). Surprisingly, the amount of radiolabeled virus that bound to CHO cells co-expressing both DAF and ICAM-1 was significantly reduced compared to the amount bound when either of these receptors was expressed alone (FIG. 3B).

Clinical Isolates of CVA21 can Induce Lytic Infection of ICAM-1 Negative Cells Via Interactions with DAF ICAM-1 is the major determinant for successful host cell entry of the CVA21 prototype strain. However, CVA21-mediated lytic infection of cells lacking ICAM-1 expression is possible in the presence of MAb cross-linked DAF. We investigated whether the clinical CVA21 isolates could lytically infect ICAM-1 negative cells via discrete interactions with cross-linked DAF. Monolayers of RD cells were either untreated or pre-treated with specific MAbs directed against individual SCRs 1, 2, 3, or 4, or a combination of anti-SCR 1 and SCR 3 of DAF prior to challenge with a single input multiplicity of CVA21. CVA21-mediated lytic infection was observed in cultures of RD cells pre-treated with MAbs directed against DAF SCR 2, 3 and 4 (FIG. 4). Confirmation that indeed, specific CVA21 capsid/DAF interactions mediated the lytic cell infection, were supplied by findings that addition of an anti-SCR 1 DAF MAb to cells pre-treated with anti-SCR 3 DAF MAb completely blocked cell lysis.

Interestingly, two of the clinical CVA21 isolates, #275238 and #272598, were capable of lytically infecting the ICAM-1 negative RD cells in the absence of cross-linking by anti-DAF MAbs (FIG. 4). In general, enteroviral binding to DAF is regarded as sequestration of virions for interactions with additional internalizing receptors, consequently to date there have been no conclusive reports demonstrating cell lytic infection mediated solely via interactions with DAF. The capacity of CVA21 clinical isolates #275238 and #2727598 to lytically infect cells in the absence of both antibody cross-linking of DAF and ICAM-1 is the first demonstration of such a receptor usage. The complete inhibition of cell lysis (FIG. 4) and significant reductions in progeny virus production by these strains of CVA21 following blockade with an anti DAF SCR 1 MAb further confirms the integrity of this finding.

To continue the analysis of this novel DAF usage, clinical and prototype strains of CVA21 were titrated for lytic infectivity on monolayer cell cultures expressing DAF alone (RD) or in combination with ICAM-1 (RD-ICAM-1). All strains of CVA21 exhibited high levels of cell lytic activity in cells expressing both DAF and ICAM-1 while only isolates #275238 and #2727598 were observed to induce lytic titers in DAF-only expressing RD cells comparable to those obtained in RD-ICAM-1 cells. In fact, isolate #275238 obtained a lytic titer in RD cells approximately 20-fold higher than in RD-ICAM-1 cells. Interestingly, at high viral input multiplicities isolate #272101, additionally exhibited a significant level of lytic infection of DAF-only expressing RD cells. The minimal but detectable level of lytic activity in RD cells by the prototype strain may be due a minority population of virions with an enhanced DAF usage phenotype.

Analysis of the ICAM-1 Binding Footprint of CVA21 Clinical Isolates

As all strains of CVA21 examined exhibited a strong ICAM-1 attachment/internalization phenotype (FIG. 1) we investigated whether they possessed a conserved ICAM-1 binding footprint. The residues constituting the CVA21-ICAM-1 receptor binding footprint have previously been identified using Cryo-electron microscopy with purified ICAM-1 and prototype Kuykendall virions. Amino acid sequence analysis of the P1 coding regions of all CVA21 strains revealed the presence of a conserved ICAM-1 footprint, identical to the previously published footprint except for a conservative coding change at VP2 168 of an Ala to Val (FIG. 5).

In an attempt to explain the increased capacity of CVA21 clinical isolates to lytically infect DAF expressing cells in the absence of ICAM-1 (FIG. 4) with respect to the prototype we searched for amino acid differences outside the ICAM-1 binding footprint (FIG. 5). A number of amino acid changes were detected in the P1 region between the three CVA21 clinical isolates and the prototype strain (FIG. 5). No amino acid changes were detected between any of the CVA21 strains in the VP4 coding region. In the VP3, VP2 and VP1 capsid proteins 13 identical changes in the same positions were detected in all clinical isolates with respect to the prototype strain. In addition, isolate #272101 exhibited a dissimilar change at position VP3 239 with a Ser compared to an Ala in the other two clinical isolates and possessed a further 9 separate amino acid changes with respect to the prototype strain scattered throughout VP1, VP2, VP3 (FIG. 5). At the amino acid level isolates #272598 and #272238 were identical, while at the nucleotide level a number a silent mutations between the two were detected.

II. Bioselection and Molecular Characterization of Coxsackievirus A21 Variant Bioselection of a CVA21 Variant that Lytically Infects Cells Independently of ICAM-1 Interactions Cellular attachment of the CVA21 prototype strain is mediated by binding to DAF and/or ICAM-1. Only ICAM-1 interactions facilitate cell internalization and interactions between CVA21 and DAF do not induce productive lytic cell infection unless DAF is cross-linked by anti-DAF mAbs. CVA21 can also lytically infect DAF-expressing RD cells when the cells are transfected with ICAM-1, highlighting that the inability of CVA21 to replicate in RD cells is only at the level of cell entry. The human melanoma cells line SkMel28 supports growth of the prototype strain of CVA21 to high viral titers, and flow cytometric analysis revealed high levels of both ICAM-1 and DAF (geometric mean fluorescence [GMF] 43.2) surface expression (FIG. 6A).

A preparation of the CVA21 prototype strain, double-plaque purified in SkMel28 cells (here designated CVA21 parental), was adapted to produce a rapid lytic infection of RD cells by repeated passages (4 passages). Flow cytometric analysis revealed that RD cells express a comparable high level of DAF (GMF 64.0) to SkMel28 cells, but do not express surface ICAM-1 (FIG. 6A). Sequential passage of the parental CVA21 in RD cells bioselected for a CVA21 variant (designated CVA21-DAFv) from the parental population that possessed the capacity to induce rapid lytic infection in the absence of ICAM-1. Dual ICAM-1 and DAF expressing SkMel28 cells supported lytic infection of both the parental and CVA21-DAFv of titers in excess of $10^7$ TCID$_{50}$/ml, while only the CVA21-DAFv induced a comparable lytic titer in RD cells (FIG. 6B).

Phenotypic Properties of CVA21-DAFv

Following adaptation to ICAM-1 negative RD cells, CVA21-DAFv produced plaques with similar efficiency on monolayers of both SkMel28 and RD cells ($5 \times 10^7$ PFU/ml). No plaques could be observed for the parental strain on RD cells despite high viral input multiplicities ($1 \times 10^8$ PFU/ml on SkMel28 cells). The CVA21-DAFv induced plaques with subtle difference in phenotype on the different cell substrates; on RD cells large, cloudy plaques were observed within 2 days post infection, whereas only small plaques of high definition were observed on SkMel28 cells (FIG. 6C). Ten successive back passages of the CVA21-DAFv in SkMel28 cells failed to select revertants to the parental phenotype with the CVA21-DAFv still retaining the capacity to lytically infect RD cells at low multiplicities of infection (1 TCID$_{50}$/96-well, data not shown). Therefore, the enhanced DAF-usage of the CVA21-DAFv appears to be a stable and desirable phenotype. Of further interest was the finding that the CVA21-DAFv ($10^2$ TCID$_{50}$) required higher levels of pooled immunoglobulin to be neutralized compared to the parental strain ($10^2$ TCID$_{50}$) (1:63 vs 1:178), hinting of partial alteration of the serological specificity of the CVA21-DAFv during the bioselection in RD cells.

CVA21-DAFv Binds to the N-Terminal Domains of DAF and ICAM-1

The prototype strain of CVA21 binds to the N-terminal domains of both ICAM-1 and DAF. To examine whether CVA21-DAFv binds directly to ICAM-1 and/or DAF in a similar manner as the prototype strain, radiolabeled binding assays were performed using CHO cells stably expressing ICAM-1 or DAF, RD cells and an ovarian carcinoma cell line, DOV13. Flow cytometric studies displayed high level of surface expression of DAF or ICAM-1 on respective transfected CHO cell line (GMF for DAF expression on CHO-DAF cells 296.2) with only DAF expressed on the surface of RD and DOV13 cells (GMF for DAF expression on RD and DOV13 cells, 64.0 and 84.0, respectively) (FIG. 6A and FIG. 7A). The CVA21 parental strain bound to both ICAM-1 and DAF (FIGS. 7B and 7C). Significant levels of CVA21-DAFv bound to both CHO-DAF and CHO-ICAM-1 cells, while only background binding was observed for CHO cells (FIGS. 7B and 7C). The specificities of the viral interactions with surface expressed ICAM-1 and DAF on the transfected CHO cells were confirmed using specific anti-DAF and anti-ICAM-1 mAb blockade of viral attachment. As anti-ICAM-1 (WEHI) and anti-DAF SCR1 (IA10) mAb blockade reduced binding of both viruses to background levels, while anti-DAF SCR3 (IH4) mAb blockade did not effect viral binding of either CVA21 preparation to the transfected CHO cells (FIGS. 7B and 7C), it is concluded that like the parental strain, CVA21-DAFv can bind to the N-terminal domains of ICAM-1 and DAF.

Figure 7:
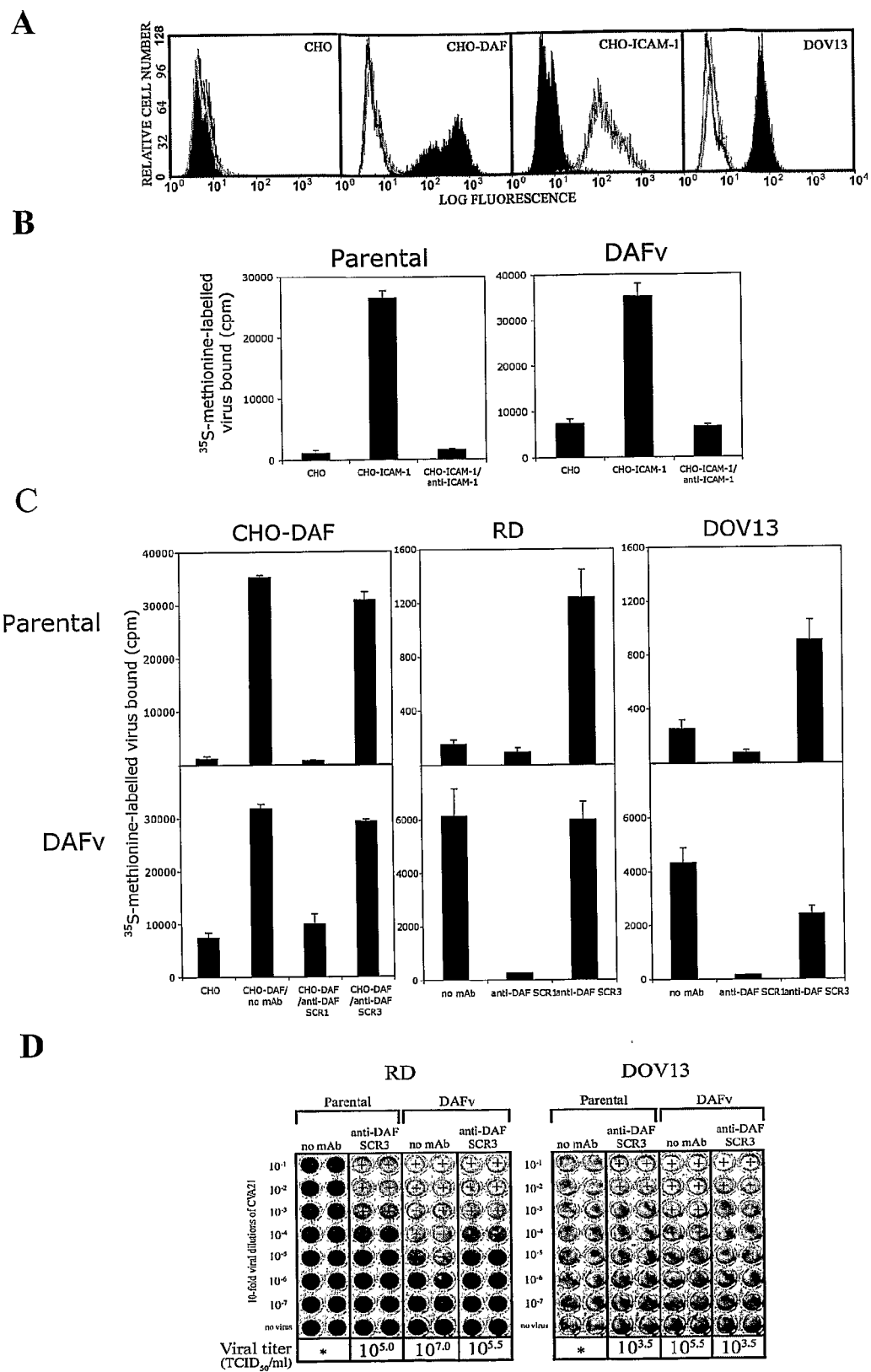
FIG. 7. Effect of anti-DAF and anti-ICAM-1 mAbs on CVA21-DAFv binding and lytic infection. (A). Flow cytometric analysis of surface levels of DAF and ICAM-1 on CHO, CHO-DAF, CHO-ICAM-1 and DOV13 cells. The solid histogram represents binding of conjugate only, the dotted histogram represents binding of anti-ICAM-1 mAb, and binding of anti-DAF mAb is shown by the filled histogram. Radiolabeled viral binding to surface expressed ICAM-1 (B) and DAF (C) on CHO, CHO-ICAM-1, CHO-DAF, RD and DOV13 cells measured by liquid scintillation counting. Results are expressed as triplicate samples+SD. (D) Effect of mAb cross-linking of DAF on CVA21 lytic infection of RD and DOV13 cells. Monolayers in 96-well plates were preincubated with anti-DAF SCR3 mAb prior to challenge with CVA21 parental and CVA21-DAFv (1-$10^6$ TCID$_{50}$/well). Following incubation for 72 h at 37° C., cell monolayers were fixed and stained with a crystal violet solution. + indicates CPE detected by microscopical examination. *viral titer less than $10^1$ TCID$_{50}$/ml.

Antibody Cross-Linking of DAF does not Enhance the Cell Infectivity of CVA21-DAFv To investigate whether subtle differences, if any, exist in the DAF binding/usage between the CVA21 parental and CVA21-DAFv strains, radiolabeled viral binding assays were employed to assess the relative levels of attachment to RD and DOV13 cells in the presence and absence of surface DAF cross-linking. Parental CVA21 and CVA21-DAFv both bind to CHO cells expressing high level of surface DAF (FIG. 7), while the prototype strain of CVA21 binds poorly to DAF-expressing, ICAM-1 negative RD cells. This is most likely due to a higher level of surface expressed DAF on the CHO-DAF cells used in this study than on the RD and DOV13 cells (FIG. 6A and FIG. 7A). The bio-selected CVA21-DAFv exhibited significant levels of attachment to both RD and DOV13 cells while little to no attachment to these cells was observed for the parental strain (FIG. 7C). Similar to CHO-DAF cells, CVA21-DAFv specific binding to RD and DOV13 cells was reduced to background levels by pretreatment by anti-SCR1 mAb (FIG. 7C).

Cross-linking of surface expressed DAF with a mAb directed against the non virus-binding SCR3 domain of DAF increased binding of the prototype CVA21 to RD cells and render the cells susceptible to lytic infection. Next, we investigated whether cross-linking of DAF on the surface of CHO-DAF and DOV13 cells results in increased viral binding as observed for RD cells. Anti-SCR3 pretreatment enhanced parental CVA21 viral binding by 8-fold on RD cells and by 4-fold on DOV13 cells (FIG. 7C). In case of CVA21-DAFv, anti-DAF SCR3 pretreatment had little to no effect on enhancing the binding to either RD or DOV13 cells. In fact, a slight decrease in binding of CVA21-DAFv to DOV13 cells was observed (FIG. 7C). The capacity of CVA21-DAFv to bind at significant levels to RD and DOV13 cells in the absence of mAb cross-linked DAF suggests an enhanced DAF-binding phenotype of the CVA21-DAFv compared to the parental strain. Viral attachment to CHO-DAF cells for both viruses was not affected by pretreatment with the anti-DAF SCR3 mAb (FIG. 7C). The level of surface expressed DAF on the stably transfected CHO-DAF cells was significantly higher than on transiently DAF-expressing CHO cells, offering a possible explanation why anti-DAF SCR3 mAb pretreatment was unable to increase viral attachment of the parental CVA21.

To determine whether anti-DAF SCR3 mAb pretreatment impacted on the susceptibility of RD and DOV13 cells to lytic infection by either CVA21 parental or CVA21-DAFv, confluent monolayers of RD and DOV13 cells were pre-incubated with anti-DAF SCR3 mAb, before viral challenge. Viral infections were allowed to proceed for 3 days at 37° C. before monolayers were assessed for lytic infection. In the absence of cross-linking anti-DAF SCR3 mAb, RD and DOV13 cells were both refractile to infection by the CVA21 parental strain even at high viral input multiplicities ($10^6$ TCID$_{50}$/well). In contrast, RD and DOV13 cells were rendered susceptible to parental CVA21 lytic infection by pretreatment with an anti-DAF SCR3 mAb (FIG. 7D). CVA21-DAFv induces lytic viral titers (>$10^{5.5}$ TCID$_{50}$/ml) in both the ICAM-1 negative RD and DOV13 cells. Surprisingly, anti-DAF SCR3 mAb pretreatment reduced the lytic titer of the CVA21-DAFv in both the RD and DOV13 cells ~100-fold compared to titers observed when no mAb was present (FIG. 7D). The CVA21-DAFv binding to the DAF-expressing cells was not enhanced by the pretreatment with the anti-DAF SCR3 mAb (FIG. 7C) and in the case of DOV13 lead to reduced attachment. These findings suggests that mAb blockade of DAF SCR3 may interfere with the cell entry mechanism of DAF SCR1-bound CAV21-DAFv (FIG. 7).

ICAM-1 not DAF Interactions Induce Capsid Conformation Changes of CVA21-DAFv

Against the background of the increased capacity of CVA21-DAFv to bind to DAF and lytically infect ICAM-1 negative cells (FIG. 6 and FIG. 7), we compared the relative binding stringency to DAF of the parental CVA21 strain and CVA21-DAFv. Radiolabeled virions were bound to CHO-DAF cells for 2 h at 4° C. and following removal of unbound virions, the cell bound virions were eluted from the cells with increasing concentrations of anti-DAF SCR1 mAb. Approximately 10-fold higher concentrations of anti-DAF SCR1 mAb were required to displace CVA21-DAFv virions compared to CVA21 parental virions from the surface of CHO-DAF cells (FIG. 8A). This finding suggests that the CVA21-DAFv binds to DAF at a less accessible site of the capsid than does CVA21 parental, or binds to DAF with higher affinity.

DAF is postulated to function as an enteroviral sequestration receptor and in general, DAF-enteroviral interactions are unable to induce the formation of detectable capsid conformational changes. To investigate whether CVA21-DAFv A-particle formation was induced by interaction with surface expressed DAF or ICAM-1, purified 160S virions were incubated with CHO-DAF or CHO-ICAM-1 cells for 2 h at 4° C. Following removal of unbound virions, cell-bound virions were permitted to elute for 2 h at 37° C. and then submitted to velocity centrifugation on 5-30% sucrose gradients. CVA21-DAFv virions eluted from ICAM-1 displayed a reduced sedimentation coefficient indicating formation of A particles and retained little to no infectivity, similar to that observed for the CVA21 prototype strain. Despite the enhanced DAF interaction of CVA21-DAFv, CVA21-DAFv virions eluted from DAF without any detectable conformational changes (FIG. 8B) and the virions retained a high level of infectivity.

Blockade of DAF Inhibits Lytic Infection of CVA21-DAFv in RD Cells

Figure 8:
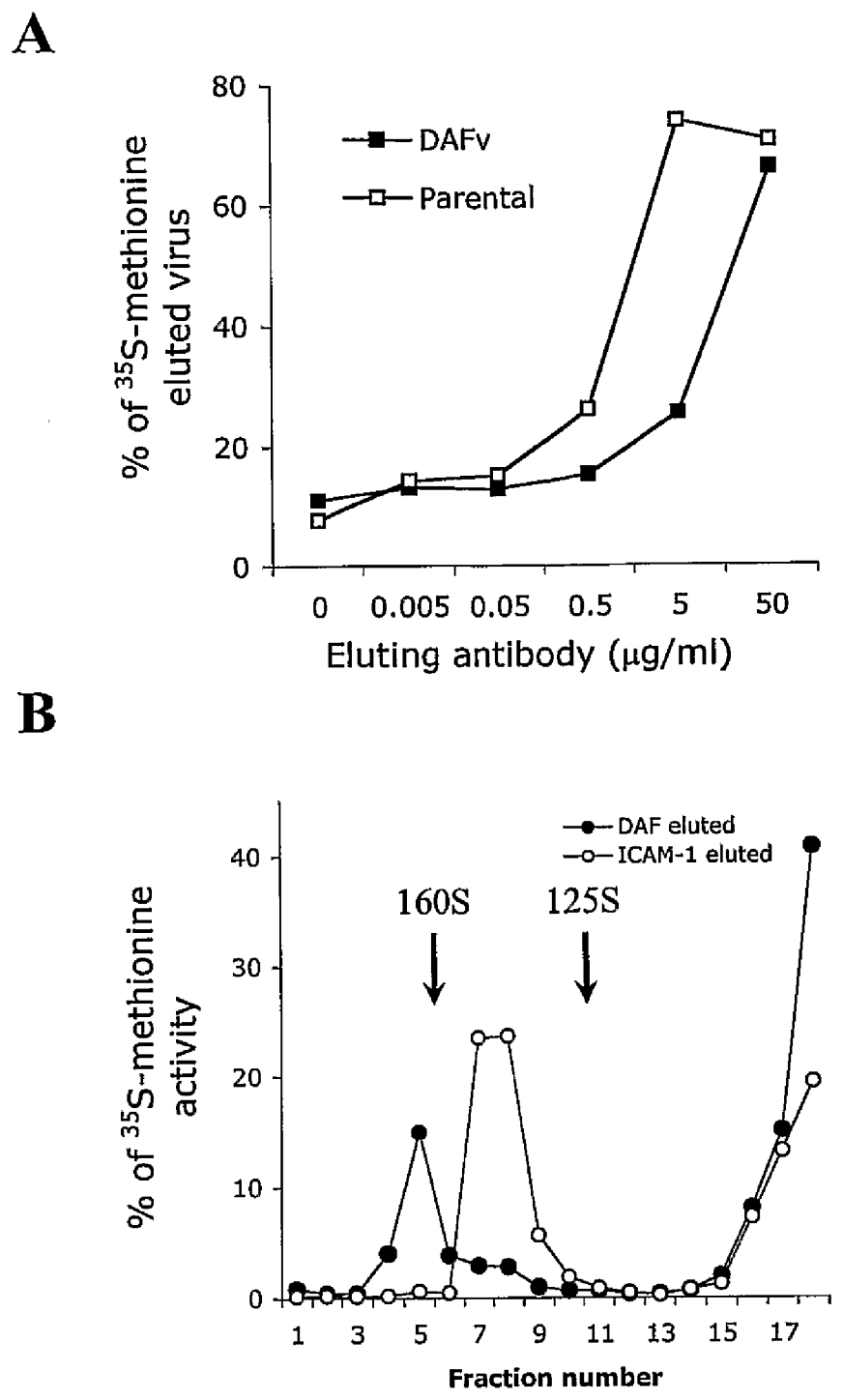

Lytic cell infection and competitive binding assays suggest an enhanced interaction between surface expressed DAF and the CVA21-DAFv compared to the parental CVA21 strain (FIG. 7 and FIG. 8). Due to this observed increased interaction, we investigated whether anti-DAF SCR1 mAb, in contrast to the parental strain, could block CVA21-DAFv lytic infection of RD cells. Anti-DAF SCR1 mAb provided complete protection against CVA21-DAFv induced lytic infection of RD cells even of input multiplicities of $10^6$ TCID$_{50}$/well (FIG. 9A). Furthermore, pretreatment of RD cells with anti-DAF SCR1 mAb significantly inhibited production of progeny virus To further confirm that the CVA21-DAFv required direct interaction with surface DAF for cell infectivity, the capacity of human recombinant sDAF (Dr. Bruce Loveland, unpublished communication) to inhibit infection of RD cells was assessed. Soluble DAF interaction with CVA21-DAFv significantly inhibited cell lytic infection, but had no detectable effect on reducing infection by the non-DAF binding CVA20. While CVA20 also binds to ICAM-1, it requires a yet unidentified receptor for cell entry (FIG. 9B). Overall, these findings demonstrate that CVA21-DAFv lytic infection is inhibited by anti-DAF SCR1 mAb and sDAF, confirming the significance of DAF interaction in the entry of CVA21-DAFv.

Molecular Determinants Conferring the DAF Phenotype of CVA21-DAFv

In order to investigate further the expanded cell tropism and increased DAF-usage phenotype of CVA21-DAFv, the nucleotide sequences of the capsid-coding region of both the CVA21 parental strain and the CVA21-DAFv were determined. The capsid protein sequences were compared to that of the CVA21 Kuykendall prototype strain, for which the interactions with DAF and ICAM-1 have been well characterized. Sequence analysis of the capsid-coding region of the double plaque-purified parental strain revealed one coding substitution in VP2 (S164L) when compared to the CVA21 prototype sequence (GenBank AF465515). The DAF and ICAM-1 binding properties of the CVA21 parental strain (FIG. 7) were not altered with respect to the prototype strain by this VP2 amino acid substitution. Following bioselection in RD cells, the VP2 L164 residue remained in the CVA21-DAFv, while two additional amino acid substitutions were detected in VP3 (R96H and E101A) and one silent mutation in VP2 (V209). As the VP2 L164 amino acid substitution is shared between the parental strain and CVA21-DAFv, it is unlikely to be involved in conferring the enhanced DAF-binding phenotype of CVA21-DAFv. CVA21-DAFv exhibited a mixed population (C/A) at nucleotide position 2038 (VP3 101) resulting in Ala/Glu, while only A (Glu) was encoded by the parental CVA21 at this position.

Figure 10:
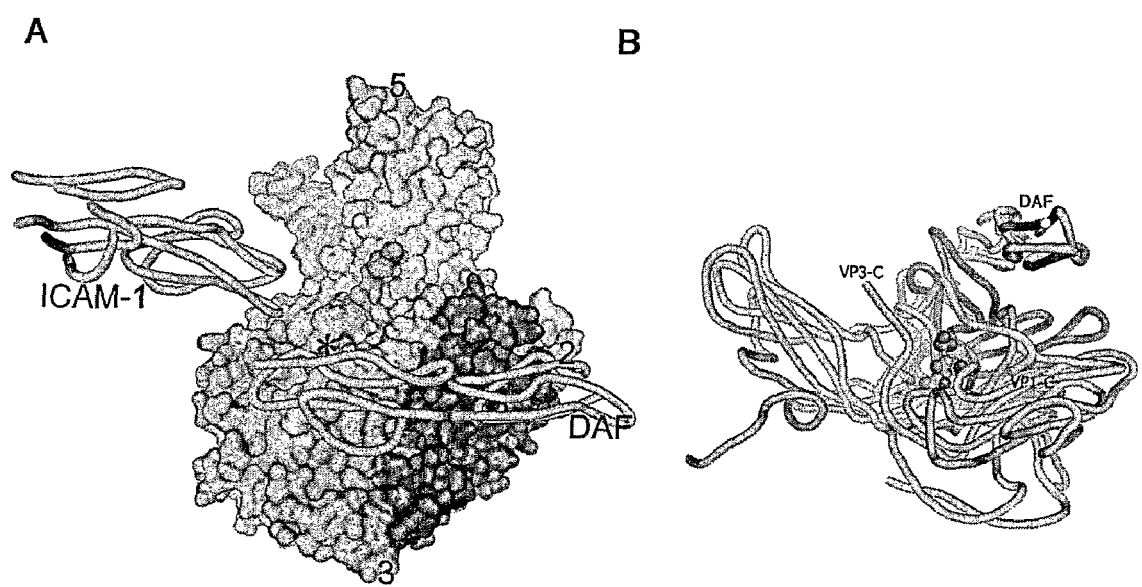
FIG. 10. Close view of predicted receptor-virus binding surface of CVA21. (A). Top view of one CVA21 protomer presented as isosurface where VP1 is depicted in yellow, VP2 in pink and VP3 in magenta. Numbers indicates the corresponding positions of icosahedaral 5-, 3-, and 2-fold axes. The interacting ICAM-1 and DAF molecules are shown as worm drawings, with DAF in wheat color and the canyon-binding ICAM-1 in green. The position of the VP3 R96 residue in CVA21 parental (space-fill mode) is partially covered by the VP1 C-terminal loop and only one nitrogen atom (blue surface next to the asterisk) in the arginine side chain can be viewed from viral surface. (B) Side view of the CVA21 protomer with proteins colored as above and VP3 residues R96 and E101 highlighted in space-fill mode. The figure was generated with program pymol (http://www.pymol.org)."

As the molecular structure of CVA21 has not been determined at atomic resolution, we modeled the architecture of the parental CVA21 based on similarities to previously determined structures of related picornaviruses in an attempt to offer an explanation for the differences in DAF-binding between CVA21 parental and CVA21-DAFv. The mutations possibly conferring the enhanced DAF-binding phenotype of CVA21-DAFv (VP3 R96H and E101A) are predicted to be embedded at the interface of capsid proteins VP1, VP2 and VP3 (FIG. 5 and FIG. 10). The VP3 residues R96 and E101 are covered by the VP3 C terminus on the side and the VP1 C terminus on the top with only the side chain nitrogen atom of arginine (R96) being solvent accessible (blue sphere in FIG. 10A). The CVA21-DAFv attachment to DAF is postulated to occur outside the capsid canyon as is the case for EV12. While the CVA21-DAFv VP3 H96 and A101 mutations are not directly located in the proposed EV12-DAF binding site, their positioning may impart an enhanced conformation or accessibility to the DAF binding footprint, resulting in an increased binding affinity to DAF compared to that of the parental strain (FIG. 8A).

III. DAF and Coxsackievirus A21 Mediated Cell Infectivity

CVA21 Binds to the N-terminal Domain of DAF

Preliminary antibody blockage studies against individual short consensus repeats (SCRs) of DAF have suggested that CVA21 binds to the DAF SCR1. However, the possibility that mapping the location of enteroviral DAF binding epitopes may be indirectly influenced by steric hindrance from DAF bound mAbs is feasible. To address such questions, surface expressed chimeric DAF molecules and DAF deletion constructs have been used to map the DAF binding domains of EV70 to SCR1 (Karnauchow, T. M., S. Dawe, D. M. Lublin, and K. Dimock 1998. Short consensus repeat domain 1 of decay-accelerating factor is required for enterovirus 70 binding. J. Virol. 72:9380-9383), CVB3 SCR2-3 (Bergelson, J. M., J. G. Mohanty, R. L. Crowell, N. F. St. John, D. M. Lublin, and R. W. Crowell 1995. Coxsackievirus B3 adapted to growth in RD cells binds to decay-accelerating factor (CD55). J. Virol. 69:1903-1906) and EV7 to SCR3 (Powell, R. M., T. Ward, D. J. Evans, and J. W. Almond 1997. Interaction between echovirus 7 and its receptor, decay-accelerating factor (CD55): evidence for a secondary cellular factor in A-particle formation. J. Virol. 71:9306-9312). In an attempt to confirm the location of the CVA21-DAF binding region, we employed chimeric DAF/CD46 receptors (FIG. 11A), in which CD46 membrane cofactor protein (MCP [CD46]), domains were replaced by the corresponding domains DAF and assessed for their capacity to bind radiolabelled CVA21. Relative levels of surface expression of the chimeric and wild-type receptors were assessed by flow cytometric analysis using mAbs specific for individual DAF SCRs and for CD46 (FIG. 11B). The anti-DAF SCR1 (IA10), SCR3 (IH4) and SCR4 (IIH6) mAbs bound only to the wild type DAF and the DAF/CD46 chimeric receptor bearing the DAF SCR1/2, SCR3 or SCR4, respectively. None of the anti-DAF mAbs bound to wild-type CD46. The anti-CD46 mAb (MCI20.6) which recognizes SCR1 of CD46 bound only to wild type CD46 or DAF/CD46 chimeric receptor bearing SCR1 of CD46. Significant levels of radiolabelled CVA21 bound to wild type DAF and DAF SCR1/CD46 chimeric receptor but not to wild type CD46 or the remaining chimeric constructs (FIG. 11C). CVA21 binding to both the wild-type DAF and the chimeric DAF SCR1/CD46 molecule was inhibited by antibody blockade with the anti-DAF SCR1 mAb. Despite, the unavailability of a DAF SCR2/CD46 chimeric receptor for this investigation, the above findings clearly demonstrate that the CVA21 capsid binding epitope like that of EV70 most probably resides in the first SCR of the DAF molecule.

Binding and Elution of CVA21 from DAF

Picornaviral cell attachment and subsequent cell entry is characterised by elution of high levels of viral particles from their specific cell surface receptor(s) following initial attachment, suggesting that receptor mediated virus elution may play an important role in the pathogenesis of picornaviral infections. Similar to many picornaviruses, when CVA21 is eluted from its natural internalizing receptor, in this case ICAM-1, it possesses a significantly reduced infectivity, hence minimizing its capacity to initiate subsequent infections. However, the characterization of the relative kinetics and infectivity of CVA21 particles eluted directly from surface expressed DAF has not previously been undertaken. Therefore, we focussed our investigations on the effects of time, temperature and pH on elution of CVA21 from DAF, where radiolabeled virus binding assays were performed using DAF expressing CHO cells as the CVA21 binding substrate. Elution of CVA21 from DAF reached maximal levels at 15 min with no further significant elution increase after this time (FIG. 12A). The amount of CVA21 eluted from DAF increased by gradually elevating the temperature from 4° C. to 42° C. while maintaining a constant elution time of 30 min (FIG. 12B). In this environment, maximal levels of CVA21 were eluted at 42° C. Not surprisingly, the infectivity of virus eluted at 42° C. was significantly less than virus eluted at 37° C. Temperatures above 37° C. may have an adverse effect on the integrity of the virion capsid resulting in reduced receptor binding and hence, diminished infective capacity. Increasing the pH of the elution environment from pH 5.5 to pH 8.0 while maintaining an elution time of 30 min and a temperature of 37° C. resulted in a continual increase in the level of CVA21 eluted from DAF (FIG. 12C).

CVA21 Eluted from DAF Retains Infectivity

A large proportion of eluted picornaviral particles is generally recognized to be non-infectious as a result of cell bound virions undergoing specific receptor induced capsid conformational changes. To compare the relative effects that binding to and elution from either surface expressed DAF or ICAM-1 exert on CVA21 infectivity, radiolabeled virus binding and cell lytic assays were performed using CHO-DAF and CHO-ICAM-1 expressing cells as the CVA21 binding substrates. Flow cytometric analysis revealed high level expression of DAF and ICAM-1 on the appropriate transfected CHO cell surface. Similar levels of radiolabeled CVA21 bound to and eluted from both DAF and ICAM-1 on the surface of the transfected cells (FIG. 13A). In contrast to virus eluted from ICAM-1, only CVA21 eluted from DAF displayed a significant retention of infectivity ($>10^5$ $TCID_{50}/100$ CPM) (FIG. 13B). To determine whether CVA21 retained high level infectivity following elution from cross-linked DAF, a similar protocol was employed, with DAF cross-linked by pretreatment with an anti-DAF SCR3 mAb (IH4). Elution from ICAM-1 was assessed from RD cells transfected with ICAM-1 (RD-ICAM-1). Minimal levels of CVA21 were eluted from both receptors at 0° C., while between 15% and 20% of bound virus was eluted from both receptors at 37° C. (FIG. 14A). However, as previously observed (FIG. 13A), CVA21 eluted from ICAM-1 possessed little infectivity (<1.0 $TCID_{50}/100$ CPM), while CVA21 eluted from cross-linked DAF exhibited significant infectivity ($>10^{2.5}$ $TCID_{50}/100$ CPM) (FIG. 14B). Despite the presence of low levels of DAF on the surface of RD-ICAM-1 cells, the lack of infectious CVA21 in the viral eluate suggests a preference for CVA21 binding to ICAM-1 over DAF when both receptors are co-expressed on the cell surface.

In an attempt to assess the relative stringency of CVA21 binding to surface DAF and ICAM-1, radiolabeled virions were bound to ICAM-1 on RD-ICAM-1 cells or mAb cross-linked DAF on the surface of RD cells at 0° C. Following removal of unbound virions, increasing concentrations of CVA21 receptor blocking mAbs (anti-DAF SCR1 or anti-ICAM-1 domain 1) were added to the appropriate cross-linked DAF or ICAM-expressing cell suspensions. Addition of an anti-ICAM-1 domain 1 mAb to the RD-ICAM-1 cells had little to no effect on displacing ICAM-1 bound CVA21 (FIG. 14C). In contrast, treatment of crosslinked-DAF RD cells with an anti-DAF SCR1 mAb at a concentration as low as 0.1 µg/ml facilitated release of approximately 50% of DAF bound CVA21, while increasing the mAb concentration to 1.0 µg/ml resulted in the expulsion of essentially all DAF bound virus (FIG. 14C).

CVA21 can Bind to DAF, Retain Infectivity and Initiate Productive Infection Following Delayed Expression of ICAM-1

Having established that CVA21 eluted from surface expressed DAF retains a high level of infectivity (FIG. 13 and FIG. 14), investigations focussed on whether DAF-eluted virus could play an active role in the pathogenesis of natural CVA21 infections. The specific question to be addressed was to determine whether virus sequestered by surface expressed DAF could initiate a productive infection utilizing a delayed induction of cell surface ICAM-1. It is generally accepted that surface expression of endogenous ICAM-1 throughout the human body is relatively low, waiting induction by the action of inflammatory cytokines such as tumour necrosis factor (TNF)-α and interleukin (IL)-1β. In an attempt to simulate such an environment, DAF expressing RD cells (ICAM-1 negative) normally refractive to CVA21 lytic infection, were transduced to express ICAM-1 or CD36 (using recombinant adenovirus vectors) at 0, 6 and 24 h following CVA21 binding to surface DAF. Flow cytometric analysis revealed significant levels of surface ICAM-1 expression at 4 h post-transduction, increasing to maximal levels approximately 16 h post adenovirus inoculation (FIG. 15A). Additional flow cytometric analysis (FIG. 15B) and Western blot assays confirmed high level expression of both ICAM-1 and CD36 at 24 h post-transduction of the RD cells by the appropriate receptor bearing recombinant adenovirus, while endogenous DAF expression was comparable between all cells. Viral infectivity assays were performed to compare the levels of progeny CVA21 propagated in the presence of transduced ICAM-1 and CD36 receptor expression at times 0, 6 or 24 h after viral binding to endogenous DAF. RD cells induced to express ICAM-1 at 0, 6 or 24 h after initial inoculation with CVA21 produced significantly higher viral yields (approximately 200-fold) than cells induced to express a mock receptor (CD36) or non-transduced RD cells (FIG. 15C). Multi-cycle replication of CVA21 in RD cells transduced to express ICAM-1 at 0, 6, 24 post DAF-binding resulted in complete lytic destruction of the cell monolayers, whereas no cell lysis was observed in cells expressing CD36 or non-transduced cells (FIG. 15D).

IV. In Vitro Lysis of Human Breast, Prostate, Colon and Ovarian Cancer Cells by Coxsackievirus A21 DAF Variant (CVA21-DAFv)

Figure 16:
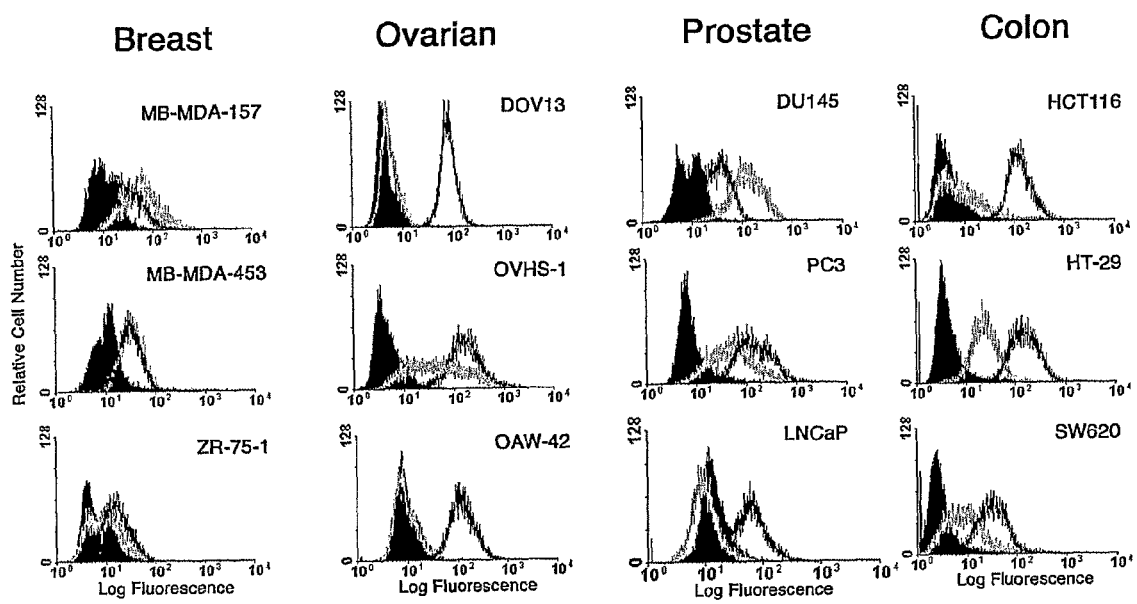
FIG. 16. Receptor expression on breast, ovarian, prostate and colon cancer cell lines. Flow cytometric analysis of ICAM-1 and DAF expression on 3 human breast, ovarian, prostate and colon cell lines. The black solid histogram represents conjugate only, ICAM-1 expression is represented by the grey histogram and DAF expression is shown by the back open histogram.

The CVA21 prototype strain is able to rapidly target and lyse malignant melanoma cells expressing high levels of the CVA21 cellular receptors, intercellular adhesion molecule-1 (ICAM-1) and decay-accelerating factor (DAF). Recently, we have shown that the bioselected CVA21-DAFv strain exhibits enhanced receptor specificity and is able to rapidly infect and lyse cells expressing either ICAM-1 or DAF or a combination of both receptors. In this study, the viral receptor expression was investigated on a panel of twelve human cancer cell lines of diverse tissue origin; three tumor cell lines from derived from human breast cancers (MDA-MB157, MDA-MB453, ZR-75-1), three ovarian cancer cell lines (DOV13, OAW-42, OVHS-1), three prostate cancerous cells (DU145, LNCaP, PC3) and three human colon cancer cells (HCT116, HT-29, SW620). As determined by flow cytometry, significant levels ICAM-1 was detected on 3/3 breast, 1/3 ovarian, 2/3 prostate and 3/3 colon cancer cells lines, while all twelve cell lines were found to express high levels of DAF (FIG. 16).

Figure 17:
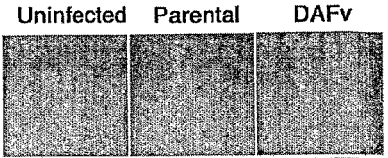
FIG. 17. In vivo oncolysis by CVA21-DAFv. Photomicrographs of CVA21-DAFv-induced infection of in vitro cultures of human breast, ovarian, prostate and colon cancer cells. Cell monolayers were infected with CVA21 parental or CVA21-DAFv and monitored for cytopathic effect. Following 72 hours post infection the monolayers were photographed.
Figure 18:
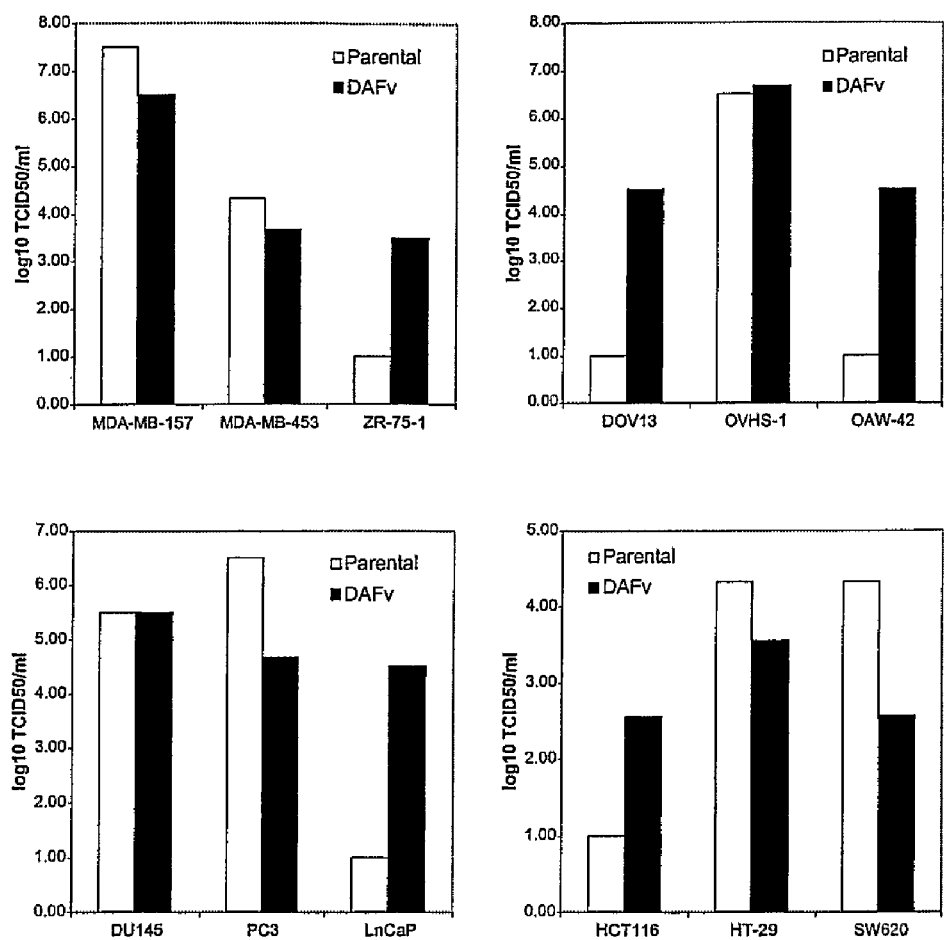
FIG. 18. Quantification of the oncolytic capacity of CVA21-DAFv in human breast, ovarian, prostate and colon cancer cell lines. Monolayers of cancer cells in 96-well plates were inoculated with 10-fold dilutions of a stock preparation of CVA21 parental or CVA21-DAFv. Following incubation for 72 hours, the monolayers examined for the presence of cytopathic effect. Fifty percent infectious end point titers were calculated using the method of Reed and Muench by scoring wells that exhibited microscopically detectable cytopathic effect (CPE) as positive.

To investigate whether CVA21-DAFv exhibits a broader oncolytic capacity than that of the CVA21 parental strain, CVA21-DAFv was used to challenge the panel of breast, ovarian, prostate and colon cancerous cells. Microscopic examination revealed that all twelve in vitro cultures challenged with CVA21-DAFv displayed a rounded phenotype (characteristics of cytopathic effect) that culminated in cell death. In contrast, cytopathic effect was only observed only for 7/12 cancerous cells lines challenged with the parental strain of CVA21 (FIG. 17). Quantification of the oncolytic capacity of CVA21-DAFv demonstrated that CVA21-DAFv supported lytic infection at titers of $>10^3$ $TCID_{50}$/ml of all twelve tested in vitro cultures, while the CVA21 parental strain induced significant lytic infection ($>10^4$ $TCID_{50}$/ml) in only 7/12 cancerous cell lines (2/3 breast, 1/3 ovarian, 2/3 prostate and 2/3 colon cancer cells) (FIG. 18). It was observed that the cell lines expressing negligible amounts of surface ICAM-1 (ZR-75-1, DOV13, OAW-42, LNCaP and HCT116) did not support replication of the parental strain of CVA21, while these cell line were readily infected by CVA21-DAFv. As only the presence of surface DAF, but not ICAM-1, is required for lytic infection by the bioselected CVA21-DAFv strain, this strain is thus clearly more effective in killing a broader range of human cancerous cell lines than the parental CVA21 strain.

V. In Vivo Oncolysis of Human Prostate Xenografts By CVA21-DAFv

Figure 19:
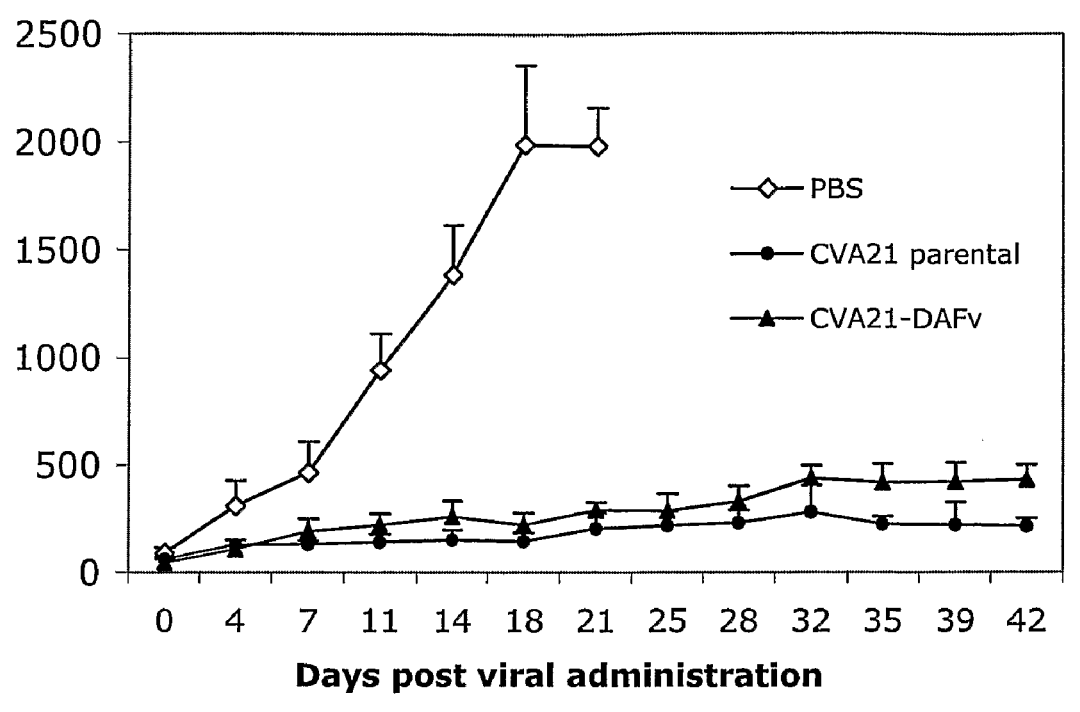

The in vivo data demonstrated that CAV21-DAFv specifically and effectively targets human cancerous cells expressing ICAM-1 and/or DAF on the cell surface. To examine whether the observed in vitro oncolysis of the panel of cancerous cells is predictive of CVA21-DAFv as anti-cancer therapeutic in vivo, we evaluated the therapeutic effect of CVA21-DAFv on prostate tumor xenografts. SCID mice bearing preformed PC3 prostate xenografts (50-100 mm$^3$) received a single intravenous dose of CVA21-DAFv, CVA21 parental, or PBS and the tumor burdens were assessed over a period of 42 days (FIG. 19). Significant reduction in tumor volumes of mice treated with either CVA21-DAFv or CVA21 parental were observed as early as 11 days following viral administration. For ethical reasons, the mice treated with PBS were euthanized 14 days post viral treatment as their tumor burden reached the upper limits imposed by the University Animal Ethics committee. Similar serum viral loads (approximately $10^5$ to $10^7$ $TCID_{50}$/ml) were observed for both CVA21-DAFv and CVA21 parental treated mice as determined by lytic viral infectivity assays (data not shown). These results demonstrate that CVA21-DAFv is as effective as the CVA21 parental strain in reducing the tumor burden of human prostate xenografts.

Discussion

I. Enterovirus Capsid Interations

Productive cell infection by the prototype strain of CVA21 is mediated by discrete interactions with surface expressed DAF and ICAM-1. In this relationship DAF functions to sequester CVA21 to the cell surface for subsequent interactions with ICAM-1 that induce capsid conformational changes and cell entry. However, the question as to whether multiple in vitro cell passages contribute to this pattern of receptor usage or not, is a subject of much contention. In particular, the DAF-binding phenotype was an area of much conjecture considering that the phylogenetically related prototype group A Coxsackieviruses A13, A15, A18 and A20, which also employ ICAM-1 as a cell internalization receptor, do not bind to surface expressed DAF. Investigations were thus undertaken to observe whether the DAF binding phenotype of the CVA21 prototype strain Kuykendall, was conserved in low in vitro passaged clinical isolates of CVA21, or was simply an artifact of multiple passage in cell cultures.

Radiolabeled viral binding assays presented herein indicate that three clinical isolates of CVA21 showed similar receptor attachment patterns as the prototype CVA21 strain (Kuykendall), characterized by the capacity to bind independently to either DAF or ICAM-1 (FIG. 1). The inability of MAb blockade directed against either DAF or ICAM-1 to completely inhibit viral binding (FIG. 2) indicates that both receptors play an essential role in the attachment/infection process of clinical isolates of CVA21. While studies into CVA21 binding in environments of high level co-expression of DAF and ICAM-1 demonstrate a reduced degree of viral binding, than in environments with two receptors expressed individually (FIG. 3). These findings suggest that high level co-expression of multiple receptors may indeed be inhibitory to optimal lytic infection. It is possible that the close proximity of DAF and ICAM-1 when co-expressed on a host cell surface results in steric hindrance causing a reduction in the availability of the receptor binding sites. If this is the case it can be reasoned that while high level expression of both receptors on a host cell does not necessarily correlate with an increased attachment level, an environment with dissimilar expression levels of the two different cellular receptors for the one virus, may be potentially advantageous. Such an environment is likely to occur on the mucosal surface of the human enteric tract where DAF expression is ubiquitous, and at significantly higher levels than ICAM-1, whose endogenous expression level is relatively low, awaiting induction by appropriate cytokines.

An unexpected finding of this study was the capacity of low passage clinical CVA21 isolates to utilize DAF interactions in a more functional role by lytically infecting RD cells solely via DAF binding in the absence of antibody crosslinking (FIG. 4). A possible explanation for these novel findings is that the viral capsids of the clinical CVA21 isolates are able to cross-link DAF in a more substantial fashion than the prototype strain, thereby, permitting viral internalization, in a mechanism similar to the artificial cross-linking action of anti-DAF MAbs (FIG. 4). Similarly, differences in receptor usage have been observed between CVB3 prototypes and low passage clinical isolates. More recently, variation in the utilization of different av integrins has been reported between laboratory and field-strains of foot-and-mouth disease virus (FMDV) demonstrating that virus isolates can exhibit altered affinities for their cellular receptors.

Here we confirm that in the absence of ICAM-1, MAb cross-linked DAF can serve as a functional internalization receptor for both prototype and clinical CVA21 strains (FIG. 4). It has previously been proposed that entry of CVA21 mediated by MAb cross-linked DAF occurs via caveolae, in contrast to the clathrin-coated pits entry route employed during viral interaction with ICAM-1. The CVA21 entry via caveolae containing the cross-linked DAF hypothesis is supported by evidence indicating that MAb clustered DAF is endocytosed following recruitment to caveolae. A possible role for DAF interaction in caveolae mediated CVA21 entry has been confirmed by recent reports of cell internalization of a DAF binding strain of EV11 via lipid rafts and/or caveolae.

The widespread expression of DAF throughout the mammalian body offers an adaptive advantage to viruses which display a higher affinity for DAF and can utilize this receptor for internalization. Such viruses may have an increased pathogenicity compared to other strains due to the expression of DAF on erythrocytes offering DAF-binding viruses a readily available vehicle for travel throughout the human body. Interestingly, serial passage of Coxsackievirus B3 and B5 isolates in polarized epithelial cells (where their natural internalization receptor, the coxsackie- and adenovirus receptor, is located in tight cell-cell junctions and DAF on the apical surface) selected for DAF binding variants, suggesting an important role for DAF infection of epithelial cell mucosal surfaces.

Genetic analysis of the P1 region of the genome coding for the capsid structural proteins, detected a number of differences in the deduced amino acid sequences between clinical CVA21 isolates and the prototype strain (FIG. 5). None of the observed coding changes mapped to the previously determined ICAM-1 footprint and the differences were scattered throughout VP1, VP2 and VP3. Residues constituting the ICAM-1 footprint were conserved in both the prototype Kuykendall strain and all clinical isolates except for amino acid 168 in VP2 (FIG. 5). At position 168 of VP2 the amino acid substitution is a Val to Ala is conservative and potentially of little significance in the conformation of the ICAM-1 binding site. Clinical isolate #272101 which exhibited significant lytic activity in DAF-only expressing RD cells but not as great as the remaining clinical isolates possessed 13 of 14 coding changes observed between all clinical isolates with respect to the prototype stain. The presence of a further 9 additional changes in #272101 compared to the other clinical isolates may have exerted some type of suppression on the enhanced DAF usage phenotype exhibited by isolates #275238 and #2727598. Repeated in vitro cell passage of the clinical CVA21 isolates possessing the elevated DAF usage phenotype in environments of both high DAF and ICAM-1 may exert pressure for the bio-selection of virions with enhanced ICAM-1 usage at the cost of reducing functional DAF interactions. Generation of such populations of virions may yield the identification of key P1 amino acid changes responsible for the altered receptor usage phenotypes.

A possible explanation for the reduced DAF usage of isolate #272101 is supplied from a report where bio-selected EV11 variants that had lost their DAF binding phenotype possessed specific amino acid changes in the BC loop of VP1 and in the puff region of VP2. Our sequence analysis revealed the presence of such unique differences in the BC loop of VP1 and the puff region of VP2 of #272101 but not in same capsid region of the other CVA clinical isolates (FIG. 5). While not shown to be conclusive, in the environment of viral attachment/cell entry, these observed 13 amino acid changes between all clinical isolates and the prototype may potentially play a role in the development of the enhanced DAF usage phenotype. However, while not addressed in this study, the involvement of additional changes located at other regions of the viral genome (e.g. 5' untranslated region) in mediating cell lytic infection cannot be discarded.

A significant difference however, between the DAF/EV7, DAF/CVB3 interaction and the DAF/CVA21 interaction is that DAF SCRs 2, 3 or 4 are involved in EV and CVB binding, while DAF SCR 1 is involved in CVA21 attachment. Given the overall structural similarities between the EV7, CVB3 and CVA21 capsids, it is proposed that the involvement of the N-terminal domains of two separate receptors with their own separate binding sites on the CVA21 capsid (i.e. DAF and ICAM-1) may occur at any stage during infection. However, the involvement of SCRs 2-4 of DAF in EV7/CVB3 binding suggests that interactions with additional receptors, such as CAR in the case of CVB3, may occur after those of DAF in order to minimize interference with access to the specific DAF binding epitopes on the viral capsid. Of some interest maybe the detection of a slight difference in the migration of VP1 of the prototype strain relative to the clinical isolates able to lytically infect ICAM-1 negative RD cells. Similarly, a variant of a CVB3 prototype (CB3-RD), generated following serial passage in RD cells, exhibited an altered VP1 mobility to the prototype, and correlated with an altered receptor specificity towards DAF compared to the parental strain.

Taken together, the results in the presented study indicate that the overall binding capability of clinical isolates to their cellular receptors has been conserved with respect to the prototype strain, however, there appears to be some discrete differences in the capacity of clinical CVA21 isolates to utilize these receptors. Similar to CVB3 field strains, the clinical CVA21 isolates possess a phenotype that facilitates the increased use of DAF in cell lytic infection, most probably as a result of passage in humans. The capacity of CVA21 to utilize both DAF and ICAM-1 for attachment and/or infection of host cells suggests the conservation of an advantageous phenotype allowing individual and/or multiple receptor usage, thereby extending the tissue tropism of the virus and significantly increasing the chances of productive infection.

II. Bioselection and Molecular Characterization of Coxsackievirus A21 Variant

As it does for many other enteroviruses, DAF serves as an attachment receptor for the prototype strain of CVA21, although ICAM-1 is required for productive CVA21 infection. In this study we describe a variant of CVA21 bioselected in vitro in ICAM-1 negative cells, which has acquired an altered and expanded cell tropism (FIGS. 6 and 7). Radiolabeled viral binding assays presented herein indicate that despite multiple passages in ICAM-1 negative RD cells, CVA21-DAFv retained the capacity to independently bind to either the N-terminal domain of ICAM-1 or DAF SCR1 (FIG. 7). In environments of extremely high levels of surface-expressed DAF, (i.e. CHO-DAF cells selected for maximal level of expression), both parental and CVA21-DAFv bound to DAF at similar levels, while only the CVA21-DAFv attached to RD and DOV13 cells which exhibited significantly less surface expression of endogenous DAF. In accordance with a previous study, mAb cross-linking of DAF by an anti-DAF SCR3 mAb significantly increased binding of the parental CVA21 to DAF-expressing RD and DOV13 cells and facilitated lytic infection in the absence of ICAM-1 (FIG. 7). However, no increase in viral binding or lytic infection by the CVA21-DAFv to mAb cross-linked RD or DOV13 cells was observed. This finding suggests that, in comparison with the parental strain, the bioselected CVA21-DAFv has optimized its interactions with DAF and that such interactions are not further enhanced by mAb cross-linking of DAF. The data indicating that parental CVA21 virions are more easily displaced than CVA21-DAFv from surface-expressed DAF during incubation with an epitope competing anti-DAF SCR1 mAb, further supports the postulate of an enhanced DAF-binding phenotype of the CVA21-DAFv compared to the parental strain (FIG. 8).

Figure 9:
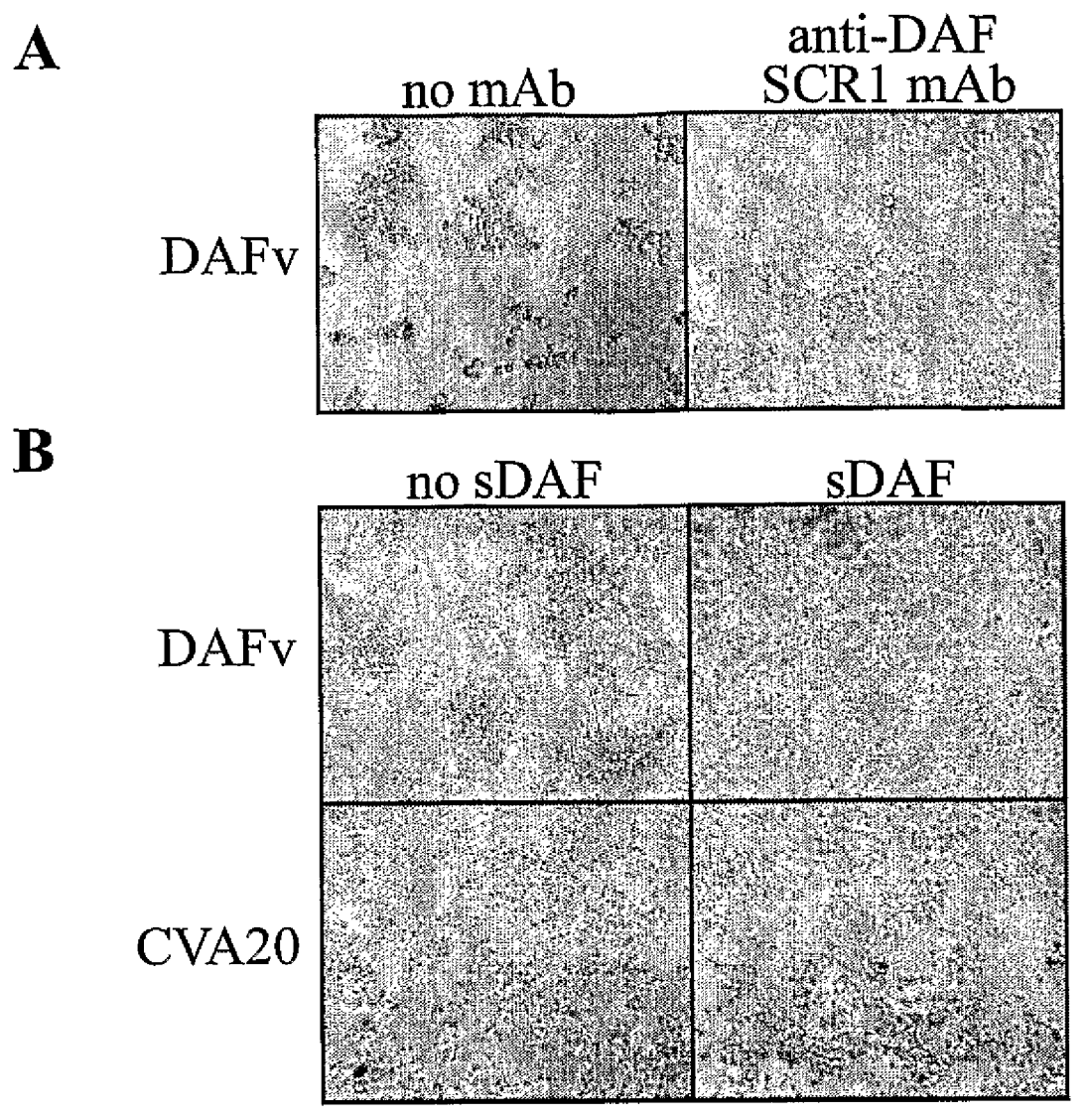

It is postulated that the role of DAF for the CVA21 prototype strain is to hold the virus in an infectious state, awaiting interactions with the entry receptor, ICAM-1, and direct binding to DAF alone does not initiate productive infection by the CVA21 prototype strain. Despite high level of surface expression of DAF or ICAM-1 on the surface of transfected CHO cells (FIG. 7A), no detectable cell infection by the parental CVA21 or CVA21-DAFv could be observed (data not shown). However, evidence in support of the enhanced DAF-usage by the CVA21-DAFv is supplied by the lytic infection of ICAM-1 negative RD and DOV13 cells which can be completely blocked by anti-DAF SCR1 mAb blockade alone even at high viral inputs (FIG. 9). This is in contrast to the partial block observed by the same mAb for the CVA21 prototype strain when used in a multiple receptor environment of DAF and ICAM-1 co-expression, where mAbs against both DAF and ICAM-1 are required to totally block infection. These findings support the postulate that CVA21-DAFv employs surface DAF as a functional cellular receptor. The observation that infection by CVA21-DAFv was inhibited by sDAF at concentrations comparable to those previously shown to exhibit an inhibitory effect on enteroviral infections, further highlights the importance of the role of DAF in CVA21-DAFv infection of RD cells (FIG. 9). Additionally, it provides evidence against the possibility that during the bioselection process, the CVA21-DAFv has adapted to use another, yet unidentified, secondary cellular receptor involved in cellular internalization in the absence of ICAM-1. The enhanced DAF-binding phenotype of CVA21-DAFv compared to that of the parental CVA21 (FIGS. 7 and 8), appears to be translated into increased cellular lytic infection (FIG. 7), not only in RD cells, but also in DAF-expressing ovarian cancer cells (DOV13).

There are numerous discrete differences in the binding interactions of many human enteroviruses to DAF. The DAF-binding sites on the CVB3, EV7 and EV12 virions are postulated to be located outside the capsid canyon at the icosahedral two-fold symmetry axes. While EV11 also interacts with DAF outside the canyon region, the DAF binding footprint is postulated to be located near the five-fold axes of the virion. Of the human enteroviruses that attach to DAF, only enterovirus 70 and CVA21 bind to the N-terminal SCR1 domain of DAF, with the remaining DAF-binding enteroviruses interacting with the central domains (SCR2-4). In addition to the fact that enteroviral binding to DAF is located outside the canyon, these interactions are reported not to result in cell infection or formation of A-particles. In the case of EV11, for which DAF binding has been assessed quantitatively, interactions with DAF are of low affinity as opposed to the interactions of the canyon-binding ICAM-1 molecule to rhinovirus 3, which is of similar affinity but of slower kinetics.

Despite that CVA21-DAFv is exhibiting an enhanced DAF-binding phenotype, only two amino acids in the capsid-coding region differ from the parental strain. During the bioselection process, CVA21-DAFv retained the capacity to bind ICAM-1 (FIG. 7). Therefore, not surprisingly, none of the observed capsid mutations were located in the previously determined ICAM-1 binding footprint, which is postulated to span the north and south canyon rims. The observed mutations of CVA21-DAFv are predicted to be located outside the capsid canyon in the VP3 α-helix (CD-loop) surrounded by the VP2 EF-loop and the C-termini of VP1 and VP3 (FIG. 10). The two mutations are predicted to be in close contact with the C-termini of VP1 and VP3 via interactions with VP1 R270 and VP3 H329. It is proposed that the observed mutations in CVA21-DAFv VP3 may be involved in enhancing the conformation of the VP3 α-helix and the C-terminal region of VP1, which corresponds to the DAF binding footprint on the surface of EV12. Such conformational changes would result in better contact between the CVA21-DAFv capsid and DAF. The postulate of an increased affinity between DAF and the two-fold depression of CVA21-DAFv virions due to the presence of VP3 H96 and A101 is in agreement with the finding that it is more difficult to displace CVA21-DAFv than parental virions from surface-expressed DAF by challenge with an anti-DAF SCR1 mAb (FIG. 8A). Low-passage clinical isolates of CVA21, which to varying degrees can lytically infect DAF-expressing RD cells in the absence of mAb cross-linking of DAF and ICAM-1 expression, also encode VP3 H96, but not the A101 mutation observed in CVA21-DAFv. In comparison, the prototype CVA21 strain encodes VP3 R96. The enhanced capacity of radiolabeled CVA21-DAFv virions to attach to surface DAF reflects mutations within the capsid-coding region rather than involvement of other viral genomic regions.

Cross-linked DAF-mediated cell lytic infection by the prototype CVA21 occurs at a slower rate than that mediated via ICAM-1 interactions, with the cell entry suggested to occur via different entry mechanisms. The cross-linked DAF-mediated entry of prototype CVA21 occurs without detectable A-particle formation and is postulated to involve caveolae, a novel entry route recently implicated in the entry of EV1 and a DAF-binding strain of EV11. Attachment of EV1 to its receptor α2β1 on the cell surface results in integrin clustering and is suggested to facilitate viral entry in a similar manner as prototype CVA21 mediated entry via cross-linked DAF. Following mAb cross-linking, DAF is postulated to be presented in a more favorable conformation on the cell surface, thereby rendering cells susceptible to infection by the prototype CVA21. Binding of the CVA21-DAFv to surface DAF appears to occur in the absence of detectable formation of A-particles (FIG. 8B). A possible explanation for this finding, is that in a similar fashion as previously postulated for low-passage clinical CVA21 isolates (also possessing the VP3 H96 residue), the CVA21-DAFv virions can effectively cross-link DAF and thereby gain entry into the cell by a mechanism related to the artificial action of cross-linking mAb. The apparent lack of detectable CVA21-DAFv A-particles eluted from the cell surface does not prove that no A-particles are being formed. A-particles will fail to accumulate if the subsequent uncoating events occur a faster rate than the initial DAF mediated conversion of 160S to 135S particles. EV1, which uses the $\alpha 2\beta 1$ integrin for cell entry, binds to the functional $\alpha 21$ domain of the $\alpha 2\beta 1$ integrin in the capsid canyon Despite being a classical canyon-binding receptor, the EV1 interaction with $\alpha 21$ does not result in viral uncoating, in contrast to binding of the soluble forms of the poliovirus receptor to poliovirus and ICAM-1 to rhinovirus. Interaction between ($\alpha 2\beta 1$-expressing cells and EV1 has, however, been implied to mediate conformational changes of the virion, but it remains uncertain whether additional cellular molecules are required for EV1 uncoating. In a similar manner, it cannot be ruled out that additional cellular protein(s) are required for CVA21-DAFv uncoating or if the presence of the mutations in the viral capsid may destabilize the capsid and thereby evade the need for a receptor mediated conformational change.

The capacity of CVA21-DAFv to lytically infect two cancerous cell lines of varying phenotype and tissue origin (RD and DOV13) highlights that the acquired use of DAF as functional receptor is not restricted to the particular cellular substrate employed in the bioselection process. The expression of DAF and other complement regulatory proteins is enhanced on the surface of many tumor cells of different origins relative to normal cells to protect the cells from the complement-mediated attack. It is suggested that CVA21-DAFv-mediated oncolysis via specific capsid interactions with surface-expressed DAF, due to the enhanced DAF-binding phenotype, could potentially be effective in the control of some human malignancies. In support of this strategy is the successful application of the prototype strain of CVA21 which is effective in the control of melanoma tumors, targeted via ICAM-1 and DAF, which both are over-expressed on the surface of malignant melanoma cells. A major finding of the present study is that viral bioselection may be a viable alternative to direct genetic manipulation in the development of novel tumor targeting oncolytic enteroviruses.

III. Coxsackievirus A21-DAF Mediated Cell Infectivity

Enteroviral interactions with DAF appear to vary between prototype and clinical isolates. In the absence of ICAM-1 expression and antibody cross-linked DAF, clinical isolates of CVA21, to varying degrees, achieve host cell lytic infection possibly by cross-linking DAF via specific viral capsid interactions. However, despite detailed descriptions of DAF interactions for numerous clinical enterovirus isolates, direct functional roles for DAF during lytic infection have not been forthcoming. The general consensus from many studies investigating enteroviral-DAF interactions is that DAF functions as a viral sequestration receptor, thereby enhancing viral presentation to additional functional internalizing receptors.

Figure 11:
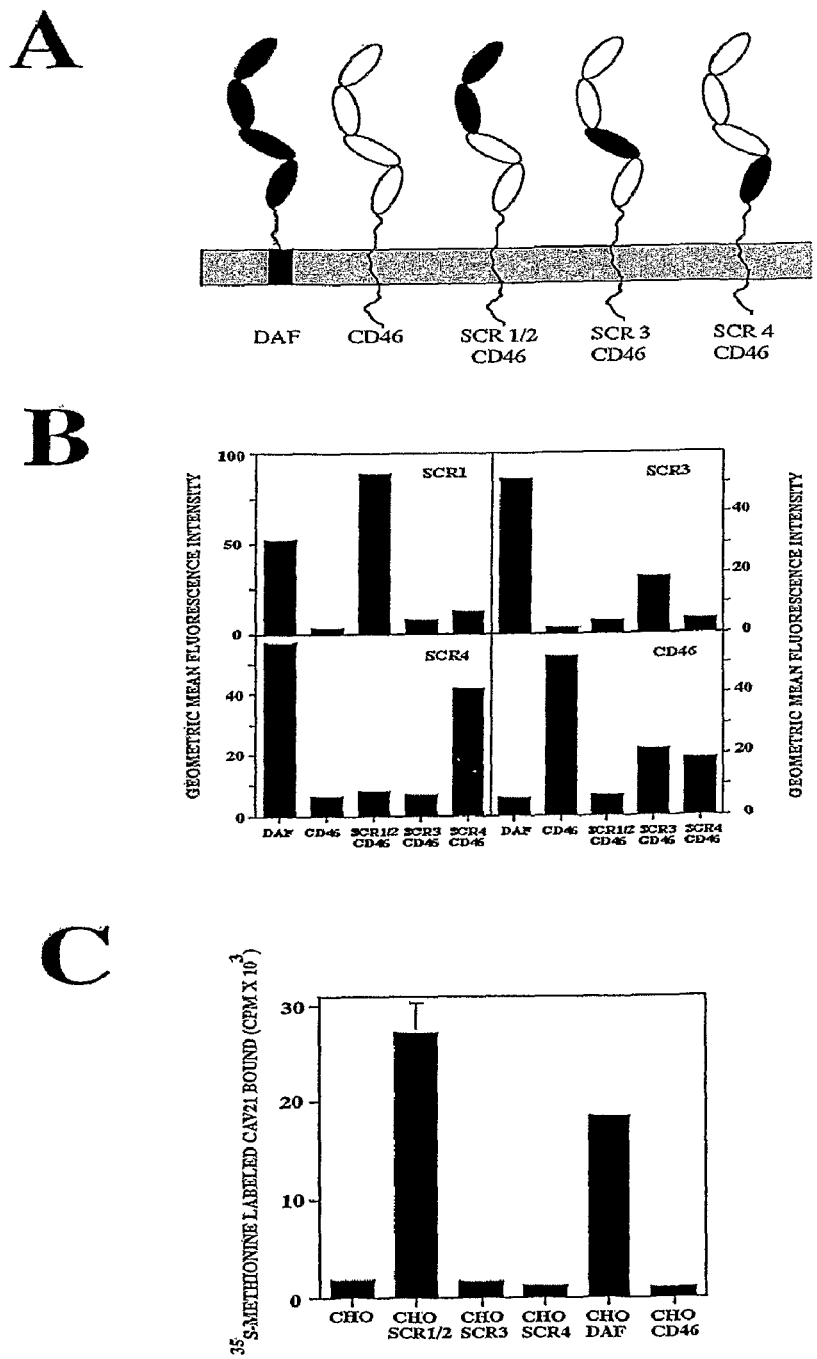
FIG. 11. Binding of radiolabelled CVA21 to chimeric DAF/CD46 receptors. (A) Schematic representation of wild type DAF, CD46 and the DAF/CD46 chimeric molecules. (B) Flow cytometric analysis of the binding of mAbs against individual SCRs of DAF and CD46. Anti-DAF mAbs were IA10 (SCR1), IH4 (SCR3), IIH6 (SCR4) and the anti-CD46 mAb (SCR1) being MCI20.6. Following incubation with the appropriate mAbs the cells were washed with PBS, resuspended in 100 µl R-phycoerythrin-conjugated F(ab')$_2$ fragment of goat anti-mouse immunoglobulin in PBS (DAKO A/S, Denmark) and incubated on ice for 20 min. Cells were washed and pelleted as above, resuspended in PBS and analyzed for DAF and CD46 expression using a FACStar analyzer (Becton Dickenson, Sydney, Australia). (C) Radiolabelled CVA21 binding to CHO cells expressing DAF, CD46 or chimeric DAF/CD46 molecules. Cells were incubated with approximately 2×$10^5$ cpm of $^{35}$S-labelled CVA21 for 1 h at 37° C. and then washed four times with PBS. The amount of cell bound CVA21 was measured by liquid scintillation. Results are expressed as the mean of triplicates+SD.
Figure 12:
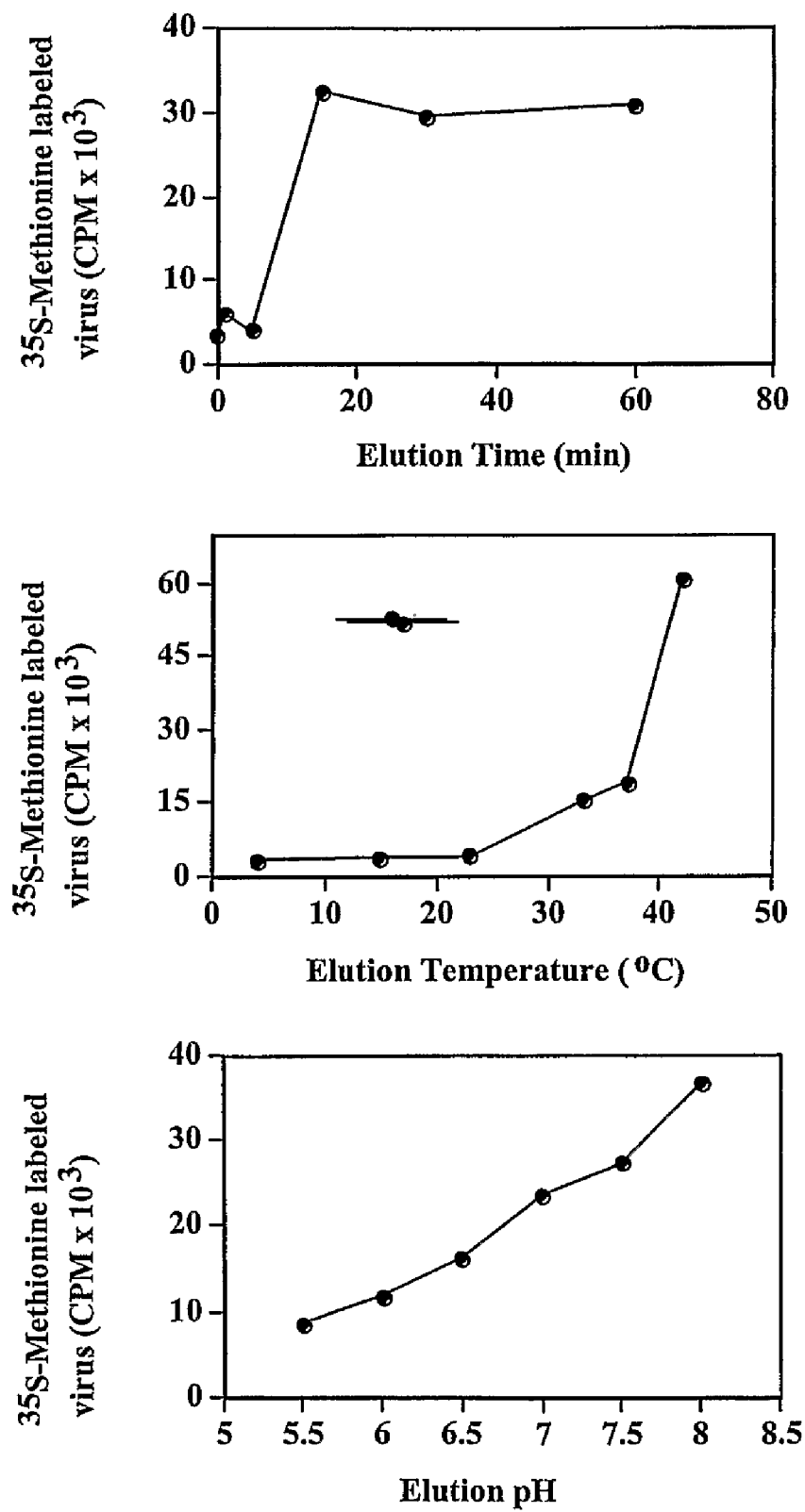
FIG. 12. CVA21 elution from DAF expressing CHO cells in response to time, temperature, and pH of the incubation media. (A) CVA21 was bound to cell surface expressed DAF at 4° C. and eluted after 2 h by increasing the temperature to 37° C. for a further 0, 1, 5, 15, 30 and 60 min. Levels of CVA21 eluted was determined by liquid scintillation counting. (B) CVA21 was bound to cell surface expressed DAF at 4° C. for 2 h then eluted by incubation at the appropriate temperature for a further 30 min. (C) CVA21 was bound to cell surface expressed DAF at 4° C. for 2 h then eluted by incubation in media of the appropriate pH at 37° C. for a further 30 min.
Figure 13:
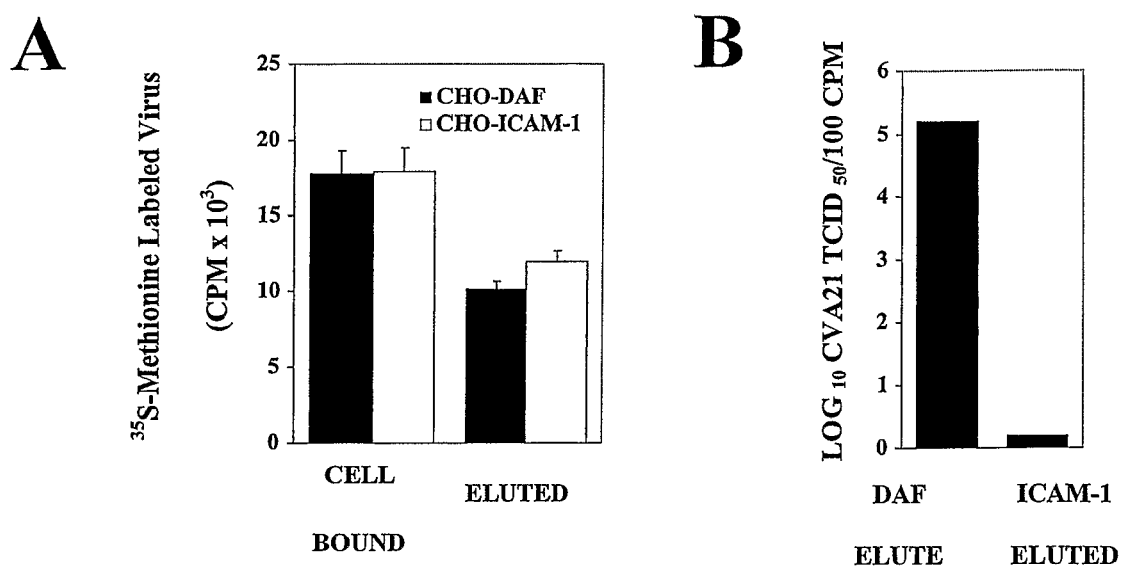
FIG. 13. Infectivity of CVA21 following elution from DAF and ICAM-1. (A) Levels of [$^{35}$S]-methionine labeled CVA21 binding to cell surface expressed DAF and ICAM-1 at 4° C., and subsequent elution of radiolabeled virus from each receptor following incubation at 37° C. Levels of [$^{35}$S]-methionine labeled virus bound was measured by liquid scintillation counting on a 1450 Microbeta TRILUX (Wallac, Turku, Finland). Results are expressed as triplicate samples+SD. (B) Lytic infection of RD-ICAM-1 cells by CVA21 following binding to and elution from cell surface expressed DAF and ICAM-1. Cell survival was quantitated from quadruplicate wells by staining with a crystal violet/methanol solution and the relative absorbance of stained cell monolayers was read on a multiscan enzyme-linked immunosorbent assay plate reader (Flow Laboratories, McLean, Va., USA) at 540 nm. Fifty percent end point titres were calculated using the method of Reed and Muench, where a well was scored as positive if the absorbance was less than the no virus control minus three standard deviations.
Figure 14:
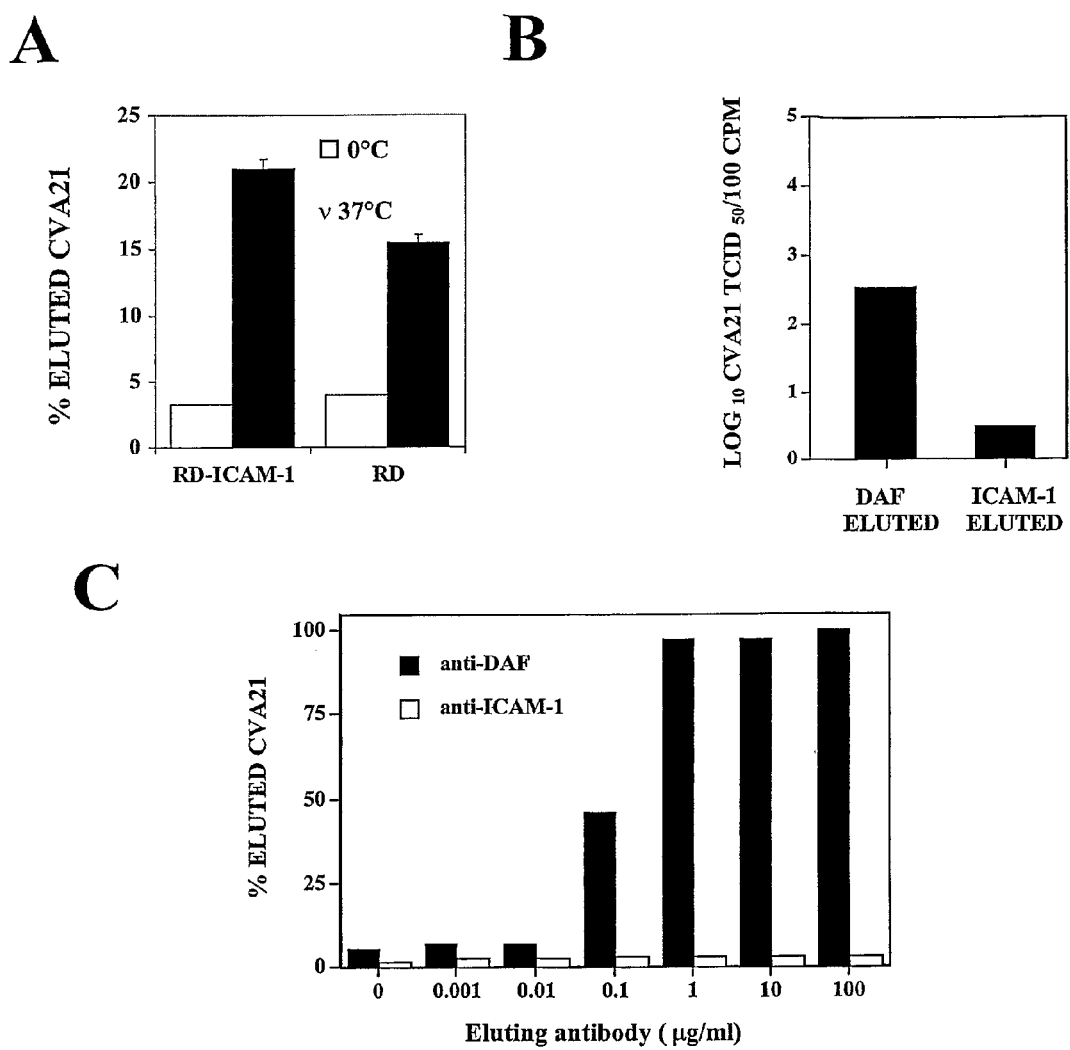
FIG. 14. Infectivity of CVA21 following elution from crosslinked-DAF (A) Elution of [$^{35}$S]-methionine labeled CVA21 from cell surface expressed ICAM-1 on RD cells (RD-ICAM-1) and mAb cross-linked DAF on RD cells at 0° C. and 37° C. Levels of [$^{35}$S]-methionine labeled virus eluted was measured by liquid scintillation counting on a 1450 Microbeta TRILUX (Wallac, Turku, Finland). Results are expressed as percentage virus eluted from triplicate samples+SD. (B) Lytic infection of RD-ICAM-1 cells by CVA21 following binding to and elution from ICAM-1 or mAb cross-linked DAF compared to control CVA21. Cell survival was quantitated from quadruplicate wells by staining with a crystal violet/methanol solution and the relative absorbance of stained cell monolayers was read on a multiscan enzyme-linked immunosorbent assay plate reader (Flow Laboratories, McLean, Va., USA) at 540 nm. Fifty percent end point titres were calculated as described in FIG. 13. (C) Stringency of CVA21 binding to ICAM-1 or crosslinked DAF. RD-ICAM-1 cells or DAF-crosslinked RD-cells [RD cells preincubated with an anti-DAF SCR3 (IH4) mAb] were incubated with approximately 2×10$^5$ cpm of $^{35}$S labelled CVA21 for 2 h at 0° C. Following four washes with cold PBS the cells were divided into multiple tubes and incubated with varying concentrations (0-100 μg/ml) of either anti-DAF mAb or anti-ICAM-1 domain 1 mAb for 1 h at 0° C. Cells and supernatant were monitored for radioactivity by liquid scintillation counting and the results expressed as the % of cell eluted $^{35}$S-labelled CVA21.

In this study we confirm, that unlike the DAF-binding echo- and coxsackie B group viruses, CVA21 binds to the N-terminal SCR of DAF (FIG. 11). Studies addressing the impact of biophysical parameters, such as time, temperature and pH on the elution of CVA21 from DAF, highlight that CVA21 particles are eluted relatively rapidly from DAF, and this elution is susceptible to increases in temperature and pH (FIG. 12). Elution of CVA21 from ICAM-1 is characterized by a dramatic reduction in iral infectivity compared to virions eluted from DAF (FIG. 13 and FIG. 14). CVA21 virions eluted from ICAM-1 undergo irreversible capsid conformational changes as a result of receptor binding leaving them incapable of binding and initiating lytic infection. In contrast, interaction of CVA21 with mAb cross-linked DAF does not result in A particle formation. A conformational change to non-infectious A particles upon receptor binding is characteristic for numerous picornaviruses such as PV, major group HRVs, and CVB3. The capacity of DAF eluted particles to remain infectious is most probably a result of the inability of DAF to induce CVA21 capsid conformational changes. CVA21 particles eluted from DAF expressing CHO cells possessed a similar sedimentation coefficient in sucrose gradients as infectious 160S particles, whereas CVA21 particles eluted from ICAM-1 expressing CHO cells exhibited a reduced sedimentation coefficient closer to that of 135S altered particles. The maintenance of CVA21 infectivity following DAF interaction, may be as a result of different regions of the virion capsid being involved in DAF binding compared to those involved in ICAM-1 binding. The CVA21 canyon is the attachment site for ICAM-1, while DAF is postulated to bind in the more easily accessible twofold depression of the capsid, a proposal recently confirmed for EV7 using cryoelectron microscopy reconstruction. Similarly, EV11 is postulated to also bind DAF in a region of the capsid outside of the canyon, however in this case, binding is proposed to involve the icosahedral fivefold axes. These findings support the theory that DAF is primarily involved in cell attachment, as binding in the twofold depression is not postulated to trigger detectable changes in the capsid conformation.

The nature of DAF binding to enteroviral capsids is suggested to be of low affinity as a consequence of a result of a very fast dissociation rate constant. In contrast, interactions of ICAM-1 with viral capsids of similar architecture are of comparable affinity but with significantly slower kinetics consistent with binding to a relatively inaccessible site, the capsid canyon. The finding that DAF-bound virions are more easily displaced than ICAM-1 bound virions during exposure to mAbs competing for their receptor binding epitopes suggest a more stringent binding to ICAM-1 than DAF. Therefore, it is suggested that the apparent differences in mAb-mediated displacement of DAF-bound CVA21 may be due to relative access to the individual locations of receptor binding sites on the capsid surface, ie. easier dissociation of viral DAF binding due to enhanced mAb accessibility possibly in the twofold depression and difficult dissociation of viral ICAM-1 binding due to restricted access of the mAb to the capsid canyon.

Figure 15:
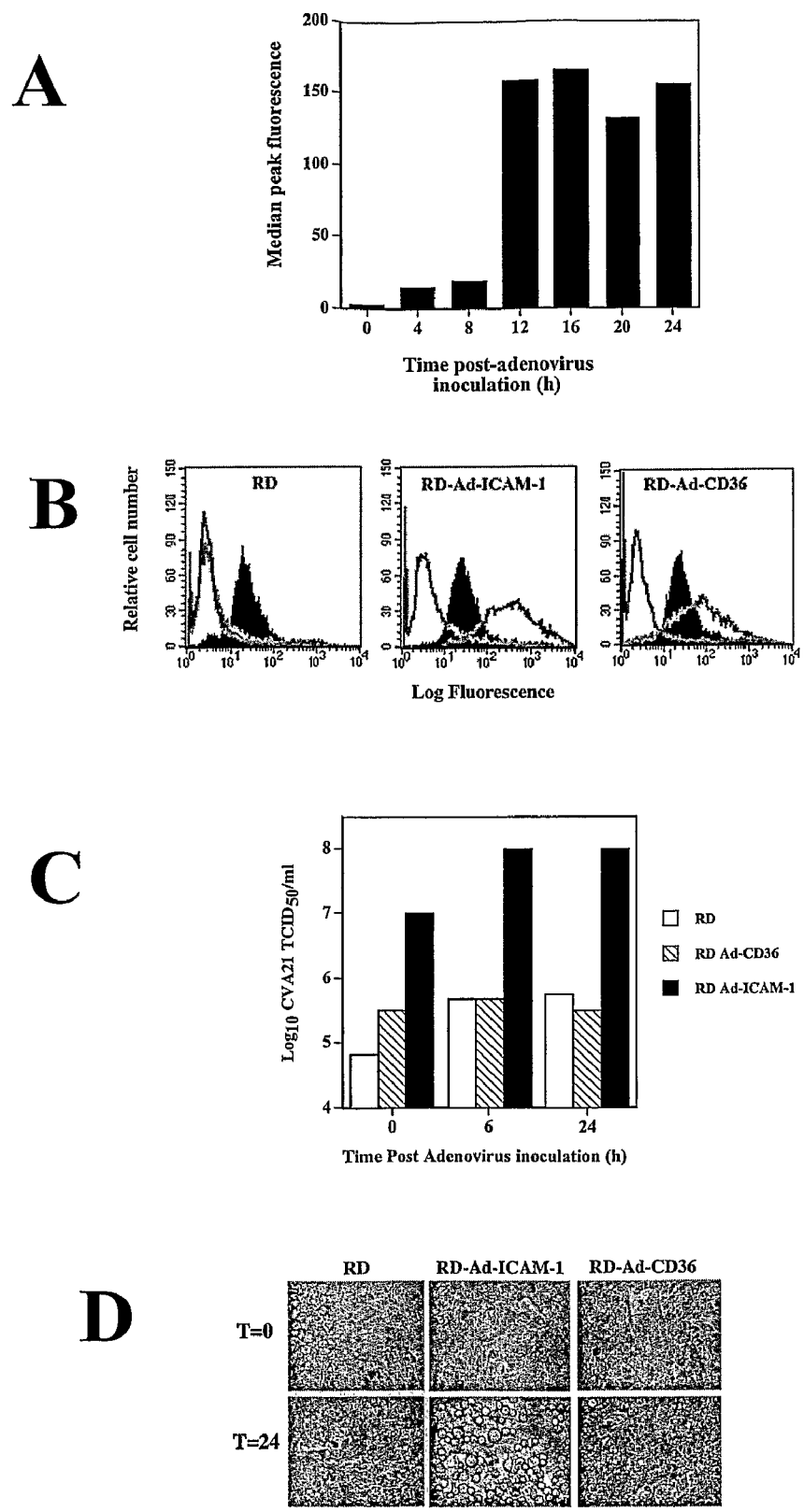
FIG. 15. CVA21 induced lytic infection of RD cells following delayed induction of ICAM-1 expression. (A) Time course of adenovirus transduced ICAM-1 expression. RD cells were induced to express the human ICAM-1 by transduction with 2.5×10$^7$ TCID$_{50}$/ml of a recombinant adenovirus containing the human ICAM-1 cDNA. Cells were assessed by flow cytometry for ICAM-1 expression at various times post-adenovirus inoculation using the anti-ICAM-1 domain mAb (IH4). (B) Flow cytometric analysis of RD cells showing surface expression of DAF, ICAM-1 and CD36 24 h following mock transduction or transduction with recombinant adenoviruses containing human ICAM-1 or CD36 cDNA. The closed histograms represent the DAF expression, while the pink histogram represents ICAM-1 expression and the blue histogram representing CD36 expression. The recombinant adenoviruses containing ICAM-1 cDNA or CD36 cDNA were constructed using an Adeno-quest Kit (Quantum Biotechnologies Inc) as per the manufacturer's instructions. (C) CVA21 lytic infection of RD cells via the delayed expression of ICAM-1 up to 24 h later. RD cells were induced to express the ICAM-1 or CD36 receptor by transduction with 2.5×10$^7$ TCID$_{50}$1 ml of a recombinant adenovirus containing ICAM-1 or CD36 cDNA 0, 6 and 24 h following CVA21 (moi=1.0 TCID$_{50}$) binding to DAF. Non-transduced RD cells served as the control. Cell survival from quadruplicate wells was quantitated by staining with a crystal violet/methanol solution and the relative absorbance of stained cell monolayers was read on a multiscan enzyme-linked immunosorbent assay plate reader (Flow Laboratories, McLean, Va., USA) at 540 nm. Fifty percent end point titres were calculated using the method of Reed and Muench, where a well was scored as positive if the absorbance was less than the no virus control minus three standard deviations. (D) CVA21 induced lytic infection. Photomicrographs (×200) of RD cell monlayers at 24 h following mock transduction or transduction with recombinant adenoviruses containing human ICAM-1 or CD36 cDNA immediately after incubation with CVA21 (moi=1.0 TCID$_{50}$).

The reversible nature of the CVA21 interaction with DAF was highlighted by the capacity of CVA21 to bind to DAF (on ICAM-1 negative cells) and remain in a infectious state for up to 24 h. The retention of infectivity allowed DAF-bound virions to undergo cell entry and subsequent lytic infection when presented with delayed ICAM-1 expression (FIG. 15). In the absence of detectable changes in cell cytopathology, relatively high levels of infectious CVA21 on monolayers of RD cells and RD cells transduced with adeno-CD36 (FIG. 15C) persisted throughout the course of investigations; most likely due to residual viral inoculum bound to DAF retaining infectivity (FIG. 13 and FIG. 14). Alternatively, it may be due to the presence of a sub-population of virions within the CVA21 prototype preparation that possess an enhanced DAF usage phenotype, allowing cross-linking of DAF and initiating a subsequent a slow infection, a finding previously described for clinical isolates of CVA21.

The capacity of CVA21 to use DAF as an attachment receptor and retain a highly infectious capacity is an extremely advantageous mechanism given the widespread distribution of DAF throughout the mammalian body, particularly on erythrocytes. In this environment, DAF expressing erythrocytes provide the virus with a ready transport vehicle through the body, where infectious virus can leave the erythrocyte surface and interact with ICAM-1 expressing cells for lytic infection. Cell surface expression of ICAM-1 is enhanced in the presence of inflammatory cytokines such as tumour necrosis factor (TNF)-α and interleukin (IL)-1β. During natural human rhinovirus infections, infected cells release such cytokines which mediate enhanced ICAM-1 expression on surrounding cells.

The data presented herein, confirm that a major role of DAF during CVA21 lytic infection is to act as a sequestration receptor, holding the virus in an infectious state awaiting the opportunity for cell entry via ICAM-1 interactions. It is most probable that CVA21 binds and elutes from DAF numerous times during cell infection, as indicated by the relatively short cycling of binding and elution. We suggest that elution from DAF is not detrimental to the capacity of CVA21 to initiate productive infection at a later stage, and in fact increases the chances of this virus achieving host cell entry by at least two distinct mechanisms. Firstly the virus can bind to DAF and elute while still retaining receptor binding capacity and hence, cell infectivity. Secondly, CVA21 can bind to DAF and wait for the availability of significant levels of ICAM-1 expression on the same cell or proximal cells to allow viral internalization and subsequent lytic infection. In aspects of both viral evolution and pathogenesis, the capacity to bind to DAF must be viewed as most advantageous for the prototype strain of CVA21 and other DAF-binding enteroviruses in maximizing cell infectivity, a phenotype that is retained and even enhanced in virulent clinical CVA2I isolates.

IV. In Vitro Lysis of Human Breast, Prostate, Colon and Ovarian Cancer Cells by Coxsackievirus A21 DAF Variant (CVA21-DAFv)

The work presented here describes the specific oncolytic capacity by CVA21-DAFv, isolated by an in vitro selection approach. Using a panel of twelve human cancerous cells lines, we have demonstrated that this bioselected strain rapidly infects all tumor-derived cell lines tested. In contrast, the CVA21 parental strain, from which the CVA21-DAFv was derived from, only mediated oncolysis in 7 out of 12 cancerous cell lines tested. Importantly, the superior oncolytic activity of CVA21-DAFv compared to the parental CVA21 was not limited to RD cells, in which this bioselected strain was generated, but was observed in the majority of other human cancer cell lines of diverse tissue origin tested (FIG. 18). Our observation that CVA21-DAFv lytically infects a larger number of tumor cell lines tested in comparison to parental CVA21, which requires the presence of ICAM-1 for cell entry, may have profound clinical impact. Human solid tumors are commonly large masses of densely packed cells, which may not always express ICAM-1. Furthermore, the expression of ICAM-1 has been shown to correlate with the metastatic potential of prostate cancer cells, i.e. ICAM-1 is expressed on the more metastatic cell lines DU145 and PC3 as compared to less metastatic LNCaP cells. In our study we have shown that while the LNCaP cells are resistant to infection by the parental strain of CVA21, this cell line as well as DU145 and PC3 are lysed by the bioselected variant of CVA21-DAFv.

V. In Vivo Oncolysis of Human Prostate Xenografts By CVA21-DAFv

While CVA21-DAFv displayed oncolytic activity against a broader range of cancerous cell lines than the CVA21 parental strain, a single dose of the bioselected strain was equally effective in reducing the tumor burden in an in vivo human prostate xenograft model. Taken together, the evidence presented here demonstrates that CVA21-DAFv has the potential to be used with great efficacy as a bio-therapeutic for numerous heterogenous cancer types.

SUMMARY

Low cell culture passage clinical isolates of CVA21 have been shown to bind DAF in addition to ICAM-1 with the DAF-binding phenotype, therefore, not likely to be acquired from multiple passages in cell culture. Increasing evidence for a more functional role of DAF in enteroviral infections has been demonstrated by the enhanced DAF using phenotype of such clinical CVA21 isolates which possess the capacity to lytically infect DAF-expressing cells in the absence of anti-DAF mAb cross-linkage or surface expressed ICAM-1.

We investigated the nature of the receptor usage of a variant of CVA21, CVA21-DAFv, bioselected to lytically infect ICAM-1 negative Rhabdomyosarcoma (RD) cells. We showed that after multiple passages in DAF-expressing RD cells, CVA21-DAFv exhibits an enhanced capacity to bind to DAF compared to the parental strain while retaining the potential to bind ICAM-1. Lytical infection of RD cells was completely abolished by an anti-DAF SCR1 mAb blockade suggesting that interactions with DAF alone mediate lytic infection. In an attempt to gain a better understanding of the molecular basis of the cellular interactions of CVA21-DAFv, the nucleotide sequence of the capsid coding region of CVA21-DAFv was determined and compared to that of the parental CVA21. Sequence comparisons revealed the presence of two unique amino acid substitutions in VP3 of CVA21-DAFv which are predicted to confer enhanced viral capsid interactions with DAF.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An isolated selected Coxsackie A21 virus capable of lytically infecting or inducing apoptosis in a cell substantially in the absence of intercellular adhesion molecule-1 (ICAM-1), wherein the selected virus comprises:
  (i) a capsid protein encoded by the nucleotide sequence of SEQ ID NO: 7, or
  (ii) a variant capsid protein encoded by a variant of the nucleotide sequence of SEQ ID NO: 7, the variant capsid protein comprising:
    (a) VP3 H96 or a conservative variation thereof wherein the conservative variation includes K, or
    (b) VP3 A101 or a conservative variation thereof wherein A101 is substituted by an amino acid selected from the group consisting of G, T, S, and M, or
    (c) both (a) and (b).

2. The Coxsackie A21 virus according to claim 1, wherein the selected virus is capable of lytically infecting a cell through decay-accelerating factor (DAF) on the cell.

3. The Coxsackie A21 virus according to claim 1, wherein the virus is bioselected by passaging a Coxsackie A21 virus not capable of lytically infecting a cell without ICAM-1 in a DAF-expressing cell line without ICAM-1 and recovering the selected Coxsackie A21 virus which is capable of lytically infecting a cell without ICAM-1.

4. The Coxsackie A21 virus according to claim 1, wherein the virus is altered, mutated or modified by site directed mutagenesis or passage in a cell where access to ICAM-1 is blocked by use of an anti-ICAM-1 antibody.

5. The Coxsackie A21 virus according to claim 1, wherein the virus comprises a capsid protein having VP3 H96 and VP3 A101.

6. The Coxsackie A21 virus according to claim 1, wherein the cell is a neoplasm.

7. The Coxsackie A21 virus according to claim 6, wherein the neoplasm is a DAF-expressing neoplasm.

8. The Coxsackie A21 virus according to claim 7, wherein the neoplasm is selected from the group consisting of lung cancer, prostate cancer, colorectal cancer, thyroid cancer, renal cancer, adrenal cancer, liver cancer, leukemia, melanoma, pre-cancerous cells, oesophageal cancer, breast cancer, brain cancer, ovarian cancer, stomach and intestinal cancer.

9. An isolated nucleic acid molecule encoding an isolated selected Coxsackie A21 virus according to claim 1.

10. The isolated nucleic acid molecule according to claim 9, wherein the nucleic acid is a single stranded RNA or complementary DNA.

11. An isolated selected Coxsackie A21 virus in the form of CVA21-DAFv comprising a capsid protein encoded by the nucleotide sequence as set forth in SEQ ID NO: 7.

12. An isolated selected Coxsackie A21 virus capable of lytically infecting or inducing apoptosis in a cell substantially in the absence of intercellular adhesion molecule-1 (ICAM-1), wherein the selected virus comprises:
  (i) a capsid protein having the amino acid sequence as set forth in SEQ ID NO: 8, or
  (ii) a capsid protein that is a variant of the amino acid sequence set forth in SEQ ID NO: 8, the variant comprising:
    (a) a conservative substitution of VP3 H96 being VP3 H96K, or
    (b) a conservative substitution of VP3 A101 selected from the group consisting of VP3 A101G, VP3 A101T, VP3 A101S, and VP3 A101M, or
    (c) both (a) and (b).

* * * * *

SEQUENCE LISTING

```
<160> NUMBER OF SEQ ID NOS: 8

<210> SEQ ID NO 1
<211> LENGTH: 2637
<212> TYPE: DNA
<213> ORGANISM: Coxsackievirus A

<400> SEQUENCE: 1
```

```
atgggggctc aagtctcaac tcaaaagacc ggtgcgcacg agaatcaaaa cgtggcagct      60
aatggatcca ccattaatta tactactatc aattactaca aagatagcgc gagtaattcg     120
gccactagac aagatctttc ccaagatcca tcaaaattca cggaaccggt taaggactta     180
atgttgaaaa cagcaccagc tttaaattca ccaaatgtgg aagcatgtgg atacagtgac     240
cgtgtaagac aaattaccct gggtaactca accattacca cacaagaagc agctaatgct     300
attgttgctt atggtgagtg gcctacttac ataaatgact cagaagcaaa cccagtagat     360
gcacccactg aaccagacgt tagtagcaac aggttttaca ccctagaatc ggtgtcttgg     420
aagactacct caaggggttg gtggtggaaa ctaccagact gtctaaaaga catgggaatg     480
tttggtcaga acatgtacta ccactactta ggacgctctg ttataccat tcatgtccag      540 tgcaatgcct caaaatttca ccaaggggca ttaggagttt ttctgatacc agagtttgtc     600
atggcctgca acactgagag caaaacatca tatgtttcat acattaacgc aaatcctggt     660
gagaggggcg gtgagttcac aaacacctac aacccatcaa acacagatgc tagtgagggc     720
agacaattcg cagcactaga ctatctgctg ggttctggcg ttctagctgg aaacgcattt     780
gtgtacccgc accagatcat taacttgcgt accaataaca gtgcaacaat cgtggtgcca     840
tatgtgaact cacttgtcat tgattgcatg gcaaaacata taactgggg cattgtcatt      900 ctaccactgg caccccttggc ctttgctgca acatcgtcac cacaggtgcc tattacagtg     960
accattgcac ccatgtgcgc agaattcaat ggattgagaa acatcaccat cccagtgcat    1020
caagggttgc aacaatgaa tacacctggt tccaatcaat tcctcacatc tgatgacttc     1080 cagtcacccct gcgccttacc caattttgat gtcactccgc caatacacat acccggagaa    1140
gtgaagaaca tgatggaact ggctgaaatt gacacgctga tcccaatgaa tgcagtggac    1200
ggaaaggtga acactatgga aatgtatcaa ataccattaa atgacaattt gagcaaggca    1260
cccatatttt gcctatctct gtcgcctgct tctgacaaac gattaagtca tacaatgttg    1320
ggtgaaattc taaattatta cacccattgg acagggtcca ttaggttcac ctttctattt    1380
tgtggtagta tgatggctac tggtaagcta cttctcagtt attccccacc aggagctaaa    1440
ccaccaacca atcgcaaaga tgcaatgttg ggcacacaca tcatctggga cctggggtta    1500
caatccagtt gttccatggt tgcaccgtgg atctctaata cagtatacag gcggtgcgca    1560
cgtgatgact tcacagaagg cgggtttata acttgctttt atcaaactag aattgttgtg    1620
cctgcttcaa ctcctaccag tatgtttatg ttaggctttg tgagtgcatg tccagatttc    1680
agtgtcagac tgcttaggga cacttcccac attagtcaat caaaactaat agcacgctca    1740
caaggcattg aagaccttat tgactcagcg ataaagaatg ctttgagagt gtctcaacca    1800
tctacggccc agtcaactga agcaaccagt ggagcaaata gtcaggaagt gccagcacta    1860
actgctgtgg aaacaggagc atctggtcag gcaatcccca gtgacgtgat ggaaaccaga    1920
cacgtgataa attacaaaac taggtctgaa tcatgccttg agtcattctt tgggagagct    1980
gcgtgtgtca atcctatc tctgaccaac tcttccaaga gtggcgagga gaaaaagcat      2040
ttcaacattt ggaatatcac atacaccgac actgttcagt tgcgtagaaa attagagttt    2100
ttcacatatt ccagatttga ccttgaaatg acttttgtgt tcacagagaa ctaccccagt    2160
acagctagtg gagaagtgcg caaccaagta taccagatca tgtacattcc accaggggca    2220
ccccgtccat catcctggga tgactataca tggcaatcct cctccaaccc ttccatcttt    2280
tacatgtatg ggaacgcacc accgcggatg tcaattcctt acgtgggat tgccaatgcc     2340 tattcacact tctatgacgg ttttgcacga gtgccacttg agggtgagaa tactgatgct    2400
```

```
ggtgatacgt tttatggatt ggtgtccata aacgattttg gagtcttagc agtcagagca    2460
gtaaaccgca gtaatccaca tacaatacac acatccgtga gagtgtacat gaaaccaaaa    2520
cacattcggt gttggtgccc cagacccct  cgcgctgtat tatacagagg agaaggagta    2580
gacatgatat ccagtgcaat tctacccctg actaaagtgg actcaattac cactttt      2637
```

<210> SEQ ID NO 2
<211> LENGTH: 879
<212> TYPE: PRT
<213> ORGANISM: Coxsackievirus A

<400> SEQUENCE: 2

```
Met Gly Ala Gln Val Ser Thr Gln Lys Thr Gly Ala His Glu Asn Gln
1               5                   10                  15

Asn Val Ala Ala Asn Gly Ser Thr Ile Asn Tyr Thr Thr Ile Asn Tyr
            20                  25                  30

Tyr Lys Asp Ser Ala Ser Asn Ser Ala Thr Arg Gln Asp Leu Ser Gln
        35                  40                  45

Asp Pro Ser Lys Phe Thr Glu Pro Val Lys Asp Leu Met Leu Lys Thr
    50                  55                  60

Ala Pro Ala Leu Asn Ser Pro Asn Val Glu Ala Cys Gly Tyr Ser Asp
65                  70                  75                  80

Arg Val Arg Gln Ile Thr Leu Gly Asn Ser Thr Ile Thr Thr Gln Glu
                85                  90                  95

Ala Ala Asn Ala Ile Val Ala Tyr Gly Glu Trp Pro Thr Tyr Ile Asn
            100                 105                 110

Asp Ser Glu Ala Asn Pro Val Asp Ala Pro Thr Glu Pro Asp Val Ser
        115                 120                 125

Ser Asn Arg Phe Tyr Thr Leu Glu Ser Val Ser Trp Lys Thr Thr Ser
    130                 135                 140

Arg Gly Trp Trp Trp Lys Leu Pro Asp Cys Leu Lys Asp Met Gly Met
145                 150                 155                 160

Phe Gly Gln Asn Met Tyr Tyr His Tyr Leu Gly Arg Ser Gly Tyr Thr
                165                 170                 175

Ile His Val Gln Cys Asn Ala Ser Lys Phe His Gln Gly Ala Leu Gly
            180                 185                 190

Val Phe Leu Ile Pro Glu Phe Val Met Ala Cys Asn Thr Glu Ser Lys
        195                 200                 205

Thr Ser Tyr Val Ser Tyr Ile Asn Ala Asn Pro Gly Glu Arg Gly Gly
    210                 215                 220

Glu Phe Thr Asn Thr Tyr Asn Pro Ser Asn Thr Asp Ala Ser Glu Gly
225                 230                 235                 240

Arg Gln Phe Ala Ala Leu Asp Tyr Leu Leu Gly Ser Gly Val Leu Ala
                245                 250                 255

Gly Asn Ala Phe Val Tyr Pro His Gln Ile Ile Asn Leu Arg Thr Asn
            260                 265                 270

Asn Ser Ala Thr Ile Val Val Pro Tyr Val Asn Ser Leu Val Ile Asp
        275                 280                 285

Cys Met Ala Lys His Asn Asn Trp Gly Ile Val Ile Leu Pro Leu Ala
    290                 295                 300

Pro Leu Ala Phe Ala Ala Thr Ser Ser Pro Gln Val Pro Ile Thr Val
305                 310                 315                 320

Thr Ile Ala Pro Met Cys Ala Glu Phe Asn Gly Leu Arg Asn Ile Thr
                325                 330                 335
```

```
Ile Pro Val His Gln Gly Leu Pro Thr Met Asn Thr Pro Gly Ser Asn
            340                 345                 350

Gln Phe Leu Thr Ser Asp Asp Phe Gln Ser Pro Cys Ala Leu Pro Asn
            355                 360                 365

Phe Asp Val Thr Pro Pro Ile His Ile Pro Gly Glu Val Lys Asn Met
370                 375                 380

Met Glu Leu Ala Glu Ile Asp Thr Leu Ile Pro Met Asn Ala Val Asp
385                 390                 395                 400

Gly Lys Val Asn Thr Met Glu Met Tyr Gln Ile Pro Leu Asn Asp Asn
                405                 410                 415

Leu Ser Lys Ala Pro Ile Phe Cys Leu Ser Leu Ser Pro Ala Ser Asp
            420                 425                 430

Lys Arg Leu Ser His Thr Met Leu Gly Glu Ile Leu Asn Tyr Tyr Thr
            435                 440                 445

His Trp Thr Gly Ser Ile Arg Phe Thr Phe Leu Phe Cys Gly Ser Met
            450                 455                 460

Met Ala Thr Gly Lys Leu Leu Leu Ser Tyr Ser Pro Pro Gly Ala Lys
465                 470                 475                 480

Pro Pro Thr Asn Arg Lys Asp Ala Met Leu Gly Thr His Ile Ile Trp
                485                 490                 495

Asp Leu Gly Leu Gln Ser Ser Cys Ser Met Val Ala Pro Trp Ile Ser
            500                 505                 510

Asn Thr Val Tyr Arg Arg Cys Ala Arg Asp Asp Phe Thr Glu Gly Gly
            515                 520                 525

Phe Ile Thr Cys Phe Tyr Gln Thr Arg Ile Val Val Pro Ala Ser Thr
            530                 535                 540

Pro Thr Ser Met Phe Met Leu Gly Phe Val Ser Ala Cys Pro Asp Phe
545                 550                 555                 560

Ser Val Arg Leu Leu Arg Asp Thr Ser His Ile Ser Gln Ser Lys Leu
                565                 570                 575

Ile Ala Arg Ser Gln Gly Ile Glu Asp Leu Ile Asp Ser Ala Ile Lys
            580                 585                 590

Asn Ala Leu Arg Val Ser Gln Pro Ser Thr Ala Gln Ser Thr Glu Ala
            595                 600                 605

Thr Ser Gly Ala Asn Ser Gln Glu Val Pro Ala Leu Thr Ala Val Glu
            610                 615                 620

Thr Gly Ala Ser Gly Gln Ala Ile Pro Ser Asp Val Met Glu Thr Arg
625                 630                 635                 640

His Val Ile Asn Tyr Lys Thr Arg Ser Glu Ser Cys Leu Glu Ser Phe
                645                 650                 655

Phe Gly Arg Ala Ala Cys Val Thr Ile Leu Ser Leu Thr Asn Ser Ser
            660                 665                 670

Lys Ser Gly Glu Glu Lys Lys His Phe Asn Ile Trp Asn Ile Thr Tyr
            675                 680                 685

Thr Asp Thr Val Gln Leu Arg Arg Lys Leu Glu Phe Phe Thr Tyr Ser
            690                 695                 700

Arg Phe Asp Leu Glu Met Thr Phe Val Phe Thr Glu Asn Tyr Pro Ser
705                 710                 715                 720

Thr Ala Ser Gly Glu Val Arg Asn Gln Val Tyr Gln Ile Met Tyr Ile
                725                 730                 735

Pro Pro Gly Ala Pro Arg Pro Ser Ser Trp Asp Asp Tyr Thr Trp Gln
            740                 745                 750

Ser Ser Ser Asn Pro Ser Ile Phe Tyr Met Tyr Gly Asn Ala Pro Pro
            755                 760                 765
```

```
Arg Met Ser Ile Pro Tyr Val Gly Ile Ala Asn Ala Tyr Ser His Phe
    770             775                 780
Tyr Asp Gly Phe Ala Arg Val Pro Leu Glu Gly Glu Asn Thr Asp Ala
785             790                 795                 800
Gly Asp Thr Phe Tyr Gly Leu Val Ser Ile Asn Asp Phe Gly Val Leu
                805                 810                 815
Ala Val Arg Ala Val Asn Arg Ser Asn Pro His Thr Ile His Thr Ser
            820                 825                 830
Val Arg Val Tyr Met Lys Pro Lys His Ile Arg Cys Trp Cys Pro Arg
        835                 840                 845
Pro Pro Arg Ala Val Leu Tyr Arg Gly Glu Gly Val Asp Met Ile Ser
    850                 855                 860
Ser Ala Ile Leu Pro Leu Thr Lys Val Asp Ser Ile Thr Thr Phe
865                 870                 875

<210> SEQ ID NO 3
<211> LENGTH: 2637
<212> TYPE: DNA
<213> ORGANISM: Coxsackievirus A

<400> SEQUENCE: 3
atgggggctc aagtctcaac tcaaaagacc ggtgcgcacg agaatcaaaa cgtggcagct      60
aatggatcca ccattaatta tactactatc aattactaca agatagcgc gagtaattcg     120
gccactagac aagatctttc caagatcca tcgaaattca cggaaccggt taaggactta     180
atgttgaaaa cagcaccagc tttaaattca ccaaatgtgg aagcatgtgg atacagtgac    240
cgtgtaagac aaattaccct gggtaactca accattacca cacaagaagc agctaatgct    300
attgttgctt atggtgagtg gcctacttac ataaatgact cagaagcaaa cccagtagat    360
gcacccactg aaccagacgt tagtagcaac aggttttaca ccctagaatc ggtgtcttgg    420
aagactacct caaggggttg gtggtggaaa ctaccagact gtctaaaaga catgggaatg    480
tttggtcaga acatgtacta ccactactta ggacgctctg gttataccat tcatgtccag    540
tgcaatgcct caaaatttca ccaaggggca ttaggagttt ttctgatacc agagtttgtc    600
atggcctgca cactgagag caaaacatca tatgtttcat acattaacgc aaatcctggt    660
gagaggggcg gtgagttcac aaacacttac aacccatcaa acacagatgc tagtgagggc    720
agacaattcg cagcactaga ctatctgctg ggttctggcg ttctagctgg aaacgcattt    780
gtgtacccgc accagatcat taacttgcgt accaataaca gtgcaacaat cgtggtgcca    840
tatgtgaact cacttgtcat tgattgcatg gcaaaacata taactgggg cattgtcatt    900
ctaccactgg cacccttggc ctttgctgca acatcgtcac acaggtgcc tattacagtg    960
accattgcac ccatgtgcgc agaattcaat ggattgagaa acatcaccat cccagtgcat   1020
caagggttgc caacaatgaa tacctggt tccaatcaat tcctcacatc tgatgacttc   1080
cagtcaccct gcgccttacc caattttgat gtcactccgc aatacacat accggagaa   1140
gtgaagaaca tgatggaatt ggctgaaatt gacacgctga tcccaatgaa tgcagtggac    1200
ggaaaggtga acactatgga aatgtatcaa ataccattaa atgacaattt gagcaaggca    1260
cccatatttt gcctatctct gtcgcctgct tctgacaaac gattaagtca tacaatgttg    1320
ggtgaaattc taaattatta cacccattgg acagggtcca ttaggttcac ctttctatt    1380
tgtggtagta tgatggctac tggtaagcta cttctcagtt attcccccacc aggagctaaa    1440
ccaccaacca atcgcaaaga tgcaatgttg ggcacacaca tcatctggga cctggggtta   1500
```
caatccagtt gttccatggt tgcaccgtgg atctctaata cagtatacag gcggtgcgca 1560
cgtgatgact tcacagaagg cgggtttata acttgctttt atcaaactag aattgttgtg 1620
cctgcttcaa ctcctaccag tatgtttatg ttaggctttg tgagtgcatg tccagatttc 1680
agtgtcagac tgcttaggga cacttcccac attagtcaat caaaactaat agcacgctca 1740
caaggcattg aagaccttat tgactcagcg ataaagaatg ctttgagagt gtctcaacca 1800
tctacggccc agtcaactga agcaaccagt ggagcaaata gtcaggaagt gccagcacta 1860
actgctgtgg aaacaggagc atctggtcag gcaattccca gtgacgtgat ggaaaccaga 1920
cacgtgataa attacaaaac taggtctgaa tcatgccttg agtcattctt tgggagagct 1980
gcgtgtgtca caatcctatc tctgaccaac tcttccaaga gtggcgagga gaaaaagcat 2040
ttcaacattt ggaatatcac atacaccgac actgttcagt tgcgtagaaa attagagttt 2100
ttcacatatt ccagatttga ccttgaaatg acttttgtgt tcacagagaa ctaccccagt 2160
acagctagtg gagaagtgcg caaccaagta taccagatca tgtacattcc accaggggca 2220
ccccgtccat catcctggga tgactataca tggcaatcct cctccaaccc ttccatcttt 2280
tacatgtatg ggaacgcacc accgcggatg tcaattcctt acgtggggat tgccaatgcc 2340
tattcacact tctatgacgg ttttgcacga gtgccacttg agggtgagaa tactgatgct 2400
ggtgatacgt tttatggatt ggtgtccata aacgattttg gagtcttagc agtcagagca 2460
gtaaaccgca gtaatccaca tacaatacac acatccgtga gagtgtacat gaaaccaaaa 2520
cacattcggt gttggtgccc cagacccccct cgcgctgtat tatacagagg agaaggagta 2580
gacatgatat ccagtgcaat tctacccctg actaaagtgg actcaattac cactttt 2637

<210> SEQ ID NO 4
<211> LENGTH: 879
<212> TYPE: PRT
<213> ORGANISM: Coxsackievirus A

<400> SEQUENCE: 4

Met Gly Ala Gln Val Ser Thr Gln Lys Thr Gly Ala His Glu Asn Gln
1 5 10 15

Asn Val Ala Ala Asn Gly Ser Thr Ile Asn Tyr Thr Thr Ile Asn Tyr
20 25 30

Tyr Lys Asp Ser Ala Ser Asn Ser Ala Thr Arg Gln Asp Leu Ser Gln
35 40 45

Asp Pro Ser Lys Phe Thr Glu Pro Val Lys Asp Leu Met Leu Lys Thr
50 55 60

Ala Pro Ala Leu Asn Ser Pro Asn Val Glu Ala Cys Gly Tyr Ser Asp
65 70 75 80

Arg Val Arg Gln Ile Thr Leu Gly Asn Ser Thr Ile Thr Thr Gln Glu
85 90 95

Ala Ala Asn Ala Ile Val Ala Tyr Gly Glu Trp Pro Thr Tyr Ile Asn
100 105 110

Asp Ser Glu Ala Asn Pro Val Asp Ala Pro Thr Glu Pro Asp Val Ser
115 120 125

Ser Asn Arg Phe Tyr Thr Leu Glu Ser Val Ser Trp Lys Thr Thr Ser
130 135 140

Arg Gly Trp Trp Trp Lys Leu Pro Asp Cys Leu Lys Asp Met Gly Met
145 150 155 160

Phe Gly Gln Asn Met Tyr Tyr His Tyr Leu Gly Arg Ser Gly Tyr Thr
165 170 175

Ile His Val Gln Cys Asn Ala Ser Lys Phe His Gln Gly Ala Leu Gly

```
                180             185             190
Val Phe Leu Ile Pro Glu Phe Val Met Ala Cys Asn Thr Glu Ser Lys
            195                 200                 205

Thr Ser Tyr Val Ser Tyr Ile Asn Ala Asn Pro Gly Glu Arg Gly Gly
    210                 215                 220

Glu Phe Thr Asn Thr Tyr Asn Pro Ser Asn Thr Asp Ala Ser Glu Gly
225                 230                 235                 240

Arg Gln Phe Ala Ala Leu Asp Tyr Leu Leu Gly Ser Gly Val Leu Ala
                245                 250                 255

Gly Asn Ala Phe Val Tyr Pro His Gln Ile Ile Asn Leu Arg Thr Asn
            260                 265                 270

Asn Ser Ala Thr Ile Val Val Pro Tyr Val Asn Ser Leu Val Ile Asp
        275                 280                 285

Cys Met Ala Lys His Asn Asn Trp Gly Ile Val Ile Leu Pro Leu Ala
    290                 295                 300

Pro Leu Ala Phe Ala Ala Thr Ser Ser Pro Gln Val Pro Ile Thr Val
305                 310                 315                 320

Thr Ile Ala Pro Met Cys Ala Glu Phe Asn Gly Leu Arg Asn Ile Thr
                325                 330                 335

Ile Pro Val His Gln Gly Leu Pro Thr Met Asn Thr Pro Gly Ser Asn
            340                 345                 350

Gln Phe Leu Thr Ser Asp Asp Phe Gln Ser Pro Cys Ala Leu Pro Asn
        355                 360                 365

Phe Asp Val Thr Pro Pro Ile His Ile Pro Gly Glu Val Lys Asn Met
    370                 375                 380

Met Glu Leu Ala Glu Ile Asp Thr Leu Ile Pro Met Asn Ala Val Asp
385                 390                 395                 400

Gly Lys Val Asn Thr Met Glu Met Tyr Gln Ile Pro Leu Asn Asp Asn
                405                 410                 415

Leu Ser Lys Ala Pro Ile Phe Cys Leu Ser Leu Ser Pro Ala Ser Asp
            420                 425                 430

Lys Arg Leu Ser His Thr Met Leu Gly Glu Ile Leu Asn Tyr Tyr Thr
        435                 440                 445

His Trp Thr Gly Ser Ile Arg Phe Thr Phe Leu Phe Cys Gly Ser Met
    450                 455                 460

Met Ala Thr Gly Lys Leu Leu Leu Ser Tyr Ser Pro Pro Gly Ala Lys
465                 470                 475                 480

Pro Pro Thr Asn Arg Lys Asp Ala Met Leu Gly Thr His Ile Ile Trp
                485                 490                 495

Asp Leu Gly Leu Gln Ser Ser Cys Ser Met Val Ala Pro Trp Ile Ser
            500                 505                 510

Asn Thr Val Tyr Arg Arg Cys Ala Arg Asp Asp Phe Thr Glu Gly Gly
        515                 520                 525

Phe Ile Thr Cys Phe Tyr Gln Thr Arg Ile Val Val Pro Ala Ser Thr
    530                 535                 540

Pro Thr Ser Met Phe Met Leu Gly Phe Val Ser Ala Cys Pro Asp Phe
545                 550                 555                 560

Ser Val Arg Leu Leu Arg Asp Thr Ser His Ile Ser Gln Ser Lys Leu
                565                 570                 575

Ile Ala Arg Ser Gln Gly Ile Glu Asp Leu Ile Asp Ser Ala Ile Lys
            580                 585                 590

Asn Ala Leu Arg Val Ser Gln Pro Ser Thr Ala Gln Ser Thr Glu Ala
        595                 600                 605
```

```
Thr Ser Gly Ala Asn Ser Gln Glu Val Pro Ala Leu Thr Ala Val Glu
610                 615                 620

Thr Gly Ala Ser Gly Gln Ala Ile Pro Ser Asp Val Met Glu Thr Arg
625                 630                 635                 640

His Val Ile Asn Tyr Lys Thr Arg Ser Glu Ser Cys Leu Glu Ser Phe
                645                 650                 655

Phe Gly Arg Ala Ala Cys Val Thr Ile Leu Ser Leu Thr Asn Ser Ser
                660                 665                 670

Lys Ser Gly Glu Glu Lys Lys His Phe Asn Ile Trp Asn Ile Thr Tyr
            675                 680                 685

Thr Asp Thr Val Gln Leu Arg Arg Lys Leu Glu Phe Phe Thr Tyr Ser
        690                 695                 700

Arg Phe Asp Leu Glu Met Thr Phe Val Phe Thr Glu Asn Tyr Pro Ser
705                 710                 715                 720

Thr Ala Ser Gly Glu Val Arg Asn Gln Val Tyr Gln Ile Met Tyr Ile
                725                 730                 735

Pro Pro Gly Ala Pro Arg Pro Ser Ser Trp Asp Tyr Thr Trp Gln
                740                 745                 750

Ser Ser Ser Asn Pro Ser Ile Phe Tyr Met Tyr Gly Asn Ala Pro Pro
            755                 760                 765

Arg Met Ser Ile Pro Tyr Val Gly Ile Ala Asn Ala Tyr Ser His Phe
770                 775                 780

Tyr Asp Gly Phe Ala Arg Val Pro Leu Glu Gly Glu Asn Thr Asp Ala
785                 790                 795                 800

Gly Asp Thr Phe Tyr Gly Leu Val Ser Ile Asn Asp Phe Gly Val Leu
                805                 810                 815

Ala Val Arg Ala Val Asn Arg Ser Asn Pro His Thr Ile His Thr Ser
                820                 825                 830

Val Arg Val Tyr Met Lys Pro Lys His Ile Arg Cys Trp Cys Pro Arg
            835                 840                 845

Pro Pro Arg Ala Val Leu Tyr Arg Gly Glu Gly Val Asp Met Ile Ser
850                 855                 860

Ser Ala Ile Leu Pro Leu Thr Lys Val Asp Ser Ile Thr Thr Phe
865                 870                 875

<210> SEQ ID NO 5
<211> LENGTH: 2637
<212> TYPE: DNA
<213> ORGANISM: Coxsackievirus A

<400> SEQUENCE: 5
atgggggctc aagtctcaac tcaaaagacc ggtgcgcacg agaatcaaaa cgtggcagct      60
aatggatcca ccattaatta tactactatt aattactaca aagatagcgc gagtaattcg     120
gctactagac aagatctttc ccaagatcca tcaaaattca cggaaccggt taaggactta     180
atgttgaaaa cagcaccagc tttaaattca ccaaatgtgg aagcatgtgg atacagtgac     240
cgtgtaagac agattaccct gggtaattca accattacca cacaagaagc agctaatgct     300
attgttgctt atggtgagtg gcctacttac ataaatgact cagaagcaaa cccagtagat     360
gcacccactg aaccagacgt tagtagcaac aggttttaca ccttagaatc ggtgtcttgg     420
aagactacct caaggggttg gtggtggaaa ctaccagact gtctaaaaga catgggaatg     480
tttggtcaaa acatgtacta ccactactta ggacgctctg ttataccat tcatgtccag     540 tgcaatgcgt caaatttca ccaaggggca ttaggagttt ttctgatacc agagtttgtc     600
atggcctgca cactgagag caaaacatca tatgtttcat acattaacgc aaatcctggt     660
```

```
gagaggggcg gtgagtttac aaacacctat aacccatcag acacagatgc taatgagggc    720
agacaattcg cagcactaga ctatttgctg ggttctggtg ttctagctgg aaacgcattt    780 gtgtaccogc accagatcat taacttgcgt accaataaca gtgcaacaat tgtggtacca    840
tatgtgaact cacttgtcat tgattgcatg gcaaaacaca taactgggg cattgtcatt     900 ctgccactgg caccottggc ctttgctgca acatcgtcac cacaggtgcc tattacagtg    960
accattgcac ccatgtgcgc agaattcaat ggattgagaa acatcaccat cccagtgcat    1020
caagggttgc caacaatgaa tacacctggt tccaatcaat tcctcacatc tgatgacttc    1080
cagtcgccct gcgccttgcc caatttcgat gtcactccgc caatacacat acccggagaa    1140
gtgaagaaca tgatggaact ggctgaaatt gacacactga tcccaatgaa tgcagtggac    1200
ggaaaggtga acactatgga aatgtatcaa ataccattaa atgacaattt gagcaaggca    1260
cccatatttt gcctatctct gtcgcctgct tctgacagac gactacgtca tacaatgttg    1320
ggtgaaattc taaattatta cacccattgg acagggtcca ttaggttcac ctttctattt    1380
tgtggtagta tgatggctac tggtaagcta cttctcagtt attccccacc aggagctaaa    1440
ccaccaacca atcgcaaaga tgcaatgttg ggcacacaca tcatctggga cctgggatta    1500
caatccagtt gttccatggt tgcaccgtgg atctctaata cagtatacag gcggtgcgca    1560
cgtgatgact tcacagaagg cgggtttata acttgctttt atcaaactag aattgttgtg    1620
cctgcttcaa ctcctaccag tatgtttatg ttaggctttg tgagtgcatg tccagatttc    1680
agtgtcagac tgcttaggga cacttcccat attagtcaat caaaattaat agcacgcgca    1740
caaggcattg aagacttat tgactcagcg ataaagagtg ctttgagagt gtctcaacca     1800
tctacggccc agtcaactga agcaaccagt ggagcaaata gtcaggaagt gccagcacta    1860
actgctgtgg aaacaggagc atctggtcag gcaatcccca gtgacgtgat ggaaaccaga    1920
cacgtgataa attacaaaac caggtctgaa tcatgccttg agtcattctt tgggagagct    1980
gcgtgtgtca atcctatc tctgactaac tcttccgaga gggggagga gaggaagcat       2040 ttcaacattt ggaatatcac atacaccgac actgttcagt tgcgtagaaa attggagttt    2100
ttcacatatt ccagatttga ccttgaaatg acttttgtgt tcacagagaa ctatcccagt    2160
acagccagtg gagaagtgcg caaccaagta taccagatca tgtacattcc accaggggca    2220
ccccgtccat catcctggga tgactataca tggcaatcct cctccaaccc ttccatcttt    2280
tacatgtatg ggaacgcacc accgcggatg tcaattcctt acgtggggat tgccaatgcc    2340
tattcacact tctacgacgg tttttgcacga gtgccacttg agggtgagaa tactgatgct    2400
ggtgacacgt tttatggatt ggtgtccata aacgattttg gagtcttagc agtcagagca    2460
gtaaaccgca gtaatccaca tacaatacac acatccgtga gagtgtacat gaagccaaaa    2520
cacattcggt gttggtgccc cagacccct cgtgctgtat tatacagagg agaaggagta    2580
gacatgatat ccagtgcaat tctacccctg actgaagtgg actcaattac cactttt     2637

<210> SEQ ID NO 6
<211> LENGTH: 879
<212> TYPE: PRT
<213> ORGANISM: Coxsackievirus A

<400> SEQUENCE: 6

Met Gly Ala Gln Val Ser Thr Gln Lys Thr Gly Ala His Glu Asn Gln
1               5                   10                  15

Asn Val Ala Ala Asn Gly Ser Thr Ile Asn Tyr Thr Thr Ile Asn Tyr
            20                  25                  30
```

```
Tyr Lys Asp Ser Ala Ser Asn Ser Ala Thr Arg Gln Asp Leu Ser Gln
         35                  40                  45

Asp Pro Ser Lys Phe Thr Glu Pro Val Lys Asp Leu Met Leu Lys Thr
 50                  55                  60

Ala Pro Ala Leu Asn Ser Pro Asn Val Glu Ala Cys Gly Tyr Ser Asp
 65                  70                  75                  80

Arg Val Arg Gln Ile Thr Leu Gly Asn Ser Thr Ile Thr Thr Gln Glu
                 85                  90                  95

Ala Ala Asn Ala Ile Val Ala Tyr Gly Glu Trp Pro Thr Tyr Ile Asn
                100                 105                 110

Asp Ser Glu Ala Asn Pro Val Asp Ala Pro Thr Glu Pro Asp Val Ser
                115                 120                 125

Ser Asn Arg Phe Tyr Thr Leu Glu Ser Val Ser Trp Lys Thr Thr Ser
                130                 135                 140

Arg Gly Trp Trp Trp Lys Leu Pro Asp Cys Leu Lys Asp Met Gly Met
145                 150                 155                 160

Phe Gly Gln Asn Met Tyr Tyr His Tyr Leu Gly Arg Ser Gly Tyr Thr
                165                 170                 175

Ile His Val Gln Cys Asn Ala Ser Lys Phe His Gln Gly Ala Leu Gly
                180                 185                 190

Val Phe Leu Ile Pro Glu Phe Val Met Ala Cys Asn Thr Glu Ser Lys
                195                 200                 205

Thr Ser Tyr Val Ser Tyr Ile Asn Ala Asn Pro Gly Glu Arg Gly Gly
                210                 215                 220

Glu Phe Thr Asn Thr Tyr Asn Pro Ser Asp Thr Asp Ala Asn Glu Gly
225                 230                 235                 240

Arg Gln Phe Ala Ala Leu Asp Tyr Leu Leu Gly Ser Gly Val Leu Ala
                245                 250                 255

Gly Asn Ala Phe Val Tyr Pro His Gln Ile Ile Asn Leu Arg Thr Asn
                260                 265                 270

Asn Ser Ala Thr Ile Val Val Pro Tyr Val Asn Ser Leu Val Ile Asp
                275                 280                 285

Cys Met Ala Lys His Asn Asn Trp Gly Ile Val Ile Leu Pro Leu Ala
                290                 295                 300

Pro Leu Ala Phe Ala Ala Thr Ser Ser Pro Gln Val Pro Ile Thr Val
305                 310                 315                 320

Thr Ile Ala Pro Met Cys Ala Glu Phe Asn Gly Leu Arg Asn Ile Thr
                325                 330                 335

Ile Pro Val His Gln Gly Leu Pro Thr Met Asn Thr Pro Gly Ser Asn
                340                 345                 350

Gln Phe Leu Thr Ser Asp Asp Phe Gln Ser Pro Cys Ala Leu Pro Asn
                355                 360                 365

Phe Asp Val Thr Pro Pro Ile His Ile Pro Gly Glu Val Lys Asn Met
                370                 375                 380

Met Glu Leu Ala Glu Ile Asp Thr Leu Ile Pro Met Asn Ala Val Asp
385                 390                 395                 400

Gly Lys Val Asn Thr Met Glu Met Tyr Gln Ile Pro Leu Asn Asp Asn
                405                 410                 415

Leu Ser Lys Ala Pro Ile Phe Cys Leu Ser Leu Ser Pro Ala Ser Asp
                420                 425                 430

Arg Arg Leu Arg His Thr Met Leu Gly Glu Ile Leu Asn Tyr Tyr Thr
                435                 440                 445

His Trp Thr Gly Ser Ile Arg Phe Thr Phe Leu Phe Cys Gly Ser Met
```

-continued

```
            450                 455                 460
Met Ala Thr Gly Lys Leu Leu Ser Tyr Ser Pro Pro Gly Ala Lys
465                 470                 475                 480

Pro Pro Thr Asn Arg Lys Asp Ala Met Leu Gly Thr His Ile Ile Trp
                485                 490                 495

Asp Leu Gly Leu Gln Ser Ser Cys Ser Met Val Ala Pro Trp Ile Ser
                500                 505                 510

Asn Thr Val Tyr Arg Arg Cys Ala Arg Asp Asp Phe Thr Glu Gly Gly
                515                 520                 525

Phe Ile Thr Cys Phe Tyr Gln Thr Arg Ile Val Val Pro Ala Ser Thr
530                 535                 540

Pro Thr Ser Met Phe Met Leu Gly Phe Val Ser Ala Cys Pro Asp Phe
545                 550                 555                 560

Ser Val Arg Leu Leu Arg Asp Thr Ser His Ile Ser Gln Ser Lys Leu
                565                 570                 575

Ile Ala Arg Ala Gln Gly Ile Glu Asp Leu Ile Asp Ser Ala Ile Lys
                580                 585                 590

Ser Ala Leu Arg Val Ser Gln Pro Ser Thr Ala Gln Ser Thr Glu Ala
                595                 600                 605

Thr Ser Gly Ala Asn Ser Gln Glu Val Pro Ala Leu Thr Ala Val Glu
610                 615                 620

Thr Gly Ala Ser Gly Gln Ala Ile Pro Ser Asp Val Met Glu Thr Arg
625                 630                 635                 640

His Val Ile Asn Tyr Lys Thr Arg Ser Glu Ser Cys Leu Glu Ser Phe
                645                 650                 655

Phe Gly Arg Ala Ala Cys Val Thr Ile Leu Ser Leu Thr Asn Ser Ser
                660                 665                 670

Glu Arg Gly Glu Glu Arg Lys His Phe Asn Ile Trp Asn Ile Thr Tyr
                675                 680                 685

Thr Asp Thr Val Gln Leu Arg Arg Lys Leu Glu Phe Phe Thr Tyr Ser
                690                 695                 700

Arg Phe Asp Leu Glu Met Thr Phe Val Phe Thr Glu Asn Tyr Pro Ser
705                 710                 715                 720

Thr Ala Ser Gly Glu Val Arg Asn Gln Val Tyr Gln Ile Met Tyr Ile
                725                 730                 735

Pro Pro Gly Ala Pro Arg Pro Ser Ser Trp Asp Asp Tyr Thr Trp Gln
                740                 745                 750

Ser Ser Ser Asn Pro Ser Ile Phe Tyr Met Tyr Gly Asn Ala Pro Pro
                755                 760                 765

Arg Met Ser Ile Pro Tyr Val Gly Ile Ala Asn Ala Tyr Ser His Phe
770                 775                 780

Tyr Asp Gly Phe Ala Arg Val Pro Leu Glu Gly Glu Asn Thr Asp Ala
785                 790                 795                 800

Gly Asp Thr Phe Tyr Gly Leu Val Ser Ile Asn Asp Phe Gly Val Leu
                805                 810                 815

Ala Val Arg Ala Val Asn Arg Ser Asn Pro His Thr Ile His Thr Ser
                820                 825                 830

Val Arg Val Tyr Met Lys Pro Lys His Ile Arg Cys Trp Cys Pro Arg
                835                 840                 845

Pro Pro Arg Ala Val Leu Tyr Arg Gly Glu Gly Val Asp Met Ile Ser
        850                 855                 860

Ser Ala Ile Leu Pro Leu Thr Glu Val Asp Ser Ile Thr Thr Phe
865                 870                 875
```

<210> SEQ ID NO 7
<211> LENGTH: 2637
<212> TYPE: DNA
<213> ORGANISM: Coxsackievirus A

<400> SEQUENCE: 7

| | | | | | |
|---|---|---|---|---|---|
| atgggggctc | aagtttcaac | gcaaaagacc | ggtgcgcacg | agaatcaaaa | cgtggcagcc | 60 |
| aatggatcca | ccattaatta | cactactatc | aactattaca | aagacagtgc | gagtaattcc | 120 |
| gctactagac | aagacctctc | ccaagatcca | tcaaaattca | cagaaccggt | taaggactta | 180 |
| atgttgaaaa | cagcaccagc | tctaaactcg | cctaacgtgg | aagcatgtgg | gtacagtgac | 240 |
| cgtgtgaggc | aaatcacttt | aggcaactcg | actattacta | cacaagaagc | agccaatgct | 300 |
| attgttgctt | acggtgaatg | gcccacttac | ataaatgatt | cagaagctaa | tccggtagat | 360 |
| gcacccactg | agccagatgt | tagtagcaac | cggttttaca | ccctagaatc | ggtgtcttgg | 420 |
| aagaccactt | caaggggatg | tgtggtggaag | ttaccagatt | gtttgaagga | catgggaatg | 480 |
| tttggtcaga | atatgtacta | tcactacttg | gggcgctctg | gttacaccat | tcatgtccag | 540 |
| tgcaacgctt | caaaatttca | ccaaggggcg | ttaggagttt | ttctgatacc | agagtttgtc | 600 |
| atggcttgca | acactgagag | taaaacgtca | tacgtttcat | acatcaatgc | aaatcctggt | 660 |
| gagagaggcg | tgagtttac | gaacacctac | aatccgttaa | atacagacgc | cagtgagggc | 720 |
| agaaagtttg | cagcattgga | ttatttgctg | ggttctggtg | ttctagcagg | aaacgccttt | 780 |
| gtgtacccgc | accagatcat | caacctacgt | accaacaaca | gtgcaacaat | tgtggtgcca | 840 |
| tacgtaaact | cacttgtgat | tgattgtatg | gcaaaacaca | ataactgggg | cattgtcata | 900 |
| ttaccactgg | cacccttggc | ctttgccgca | catcgtcac | cacaggtgcc | tattacagtg | 960 |
| accattgcac | ccatgtgtac | agaattcaat | gggttgagaa | acatcaccgt | cccagtacat | 1020 |
| caagggttgc | cgacaatgaa | cacacctggt | tccaatcaat | tccttacatc | tgatgacttc | 1080 |
| cagtcgccct | gtgccttacc | taattttgat | gttactccac | aatacacat | acccggggaa | 1140 |
| gtaaagaata | tgatggaact | agctgaaatt | gacacattga | tcccaatgaa | cgcagtggac | 1200 |
| gggaaggtga | cacaatggga | gatgtatcaa | ataccattga | atgacaattt | gagcaaggca | 1260 |
| cctatattct | gtttatccct | atccctgct | tctgataaac | gactgagcca | caccatgttg | 1320 |
| ggtgmaatcc | taaattatta | cacccattgg | acggggtcca | tcaggttcac | ctttctattt | 1380 |
| tgtggtagta | tgatggccac | tggtaaactg | ctcctcagct | attccccacc | gggagctaaa | 1440 |
| ccaccaacca | atcgcaagga | tgcaatgcta | ggcacacaca | tcatctggga | cctagggtta | 1500 |
| caatccagtt | gttccatggt | tgcaccgtgg | atctccaaca | cagtgtacag | acggtgtgca | 1560 |
| cgtgatgact | tcactgaggg | cggatttata | acttgcttct | atcaaactag | aattgtggta | 1620 |
| cctgcttcaa | cccctaccag | tatgttcatg | ttaggctttg | ttagtgcgtg | tccagacttc | 1680 |
| agtgtcagac | tgcttaggga | cactcccccat | attagtcaat | cgaaactaat | aggacgtaca | 1740 |
| caaggcattg | aagacctcat | tgacacagcg | ataaagaatg | ccttaagagt | gtcccaacca | 1800 |
| ccctcgaccc | agtcaactga | agcaactagt | ggagtgaata | gccaggaggt | gccagctcta | 1860 |
| actgctgtgg | aaacaggagc | atctggtcaa | gcaatcccca | gtgatgtggt | ggaaactagg | 1920 |
| cacgtggtaa | attacaaaac | caggtctgaa | tcgtgtcttg | agtcattctt | gggagagct | 1980 |
| gcgtgtgtca | aatcctatc | cttgaccaac | tcctccaaga | gcggagagga | gaaaaagcat | 2040 |
| ttcaacatat | ggaatattac | atacaccgac | actgtccagt | tacgcagaaa | attagagttt | 2100 |
| ttcacgtatt | ccaggtttga | tcttgaaatg | acttttgtat | tcacagagaa | ctatcctagt | 2160 |

```
acagccagtg gagaagtgcg aaaccaggtg taccagatca tgtatattcc accaggggca   2220
ccccgcccat catcctggga tgactacaca tggcaatcct cttcaaaccc ttccatcttc   2280
tacatgtatg gaaatgcacc tccacggatg tcaattcctt acgtagggat tgccaatgcc   2340
tattcacact tctacgatgg ctttgcacgg gtgccacttg agggtgagaa caccgatgct   2400
ggcgacacgt tttacggttt agtgtccata aatgattttg gagttttagc agttagagca   2460
gtaaaccgca gtaatccaca taatatacac acatctgtga gagtgtacat gaaaccaaaa   2520
cacattcggt gttggtgccc cagacctcct cgagctgtat tatacagggg agagggagtg   2580
gacatgatat ccagtgcaat tctacctctg accaaggtag actcaattac cactttt      2637
```

<210> SEQ ID NO 8
<211> LENGTH: 879
<212> TYPE: PRT
<213> ORGANISM: Coxsackievirus A
<220> FEATURE:
<221> NAME/KEY: misc_feature
<222> LOCATION: (442)..(442)
<223> OTHER INFORMATION: Xaa can be any naturally occurring amino acid

<400> SEQUENCE: 8

```
Met Gly Ala Gln Val Ser Thr Gln Lys Thr Gly Ala His Glu Asn Gln
  1               5                  10                  15

Asn Val Ala Ala Asn Gly Ser Thr Ile Asn Tyr Thr Thr Ile Asn Tyr
             20                  25                  30

Tyr Lys Asp Ser Ala Ser Asn Ser Ala Thr Arg Gln Asp Leu Ser Gln
         35                  40                  45

Asp Pro Ser Lys Phe Thr Glu Pro Val Lys Asp Leu Met Leu Lys Thr
     50                  55                  60

Ala Pro Ala Leu Asn Ser Pro Asn Val Glu Ala Cys Gly Tyr Ser Asp
 65                  70                  75                  80

Arg Val Arg Gln Ile Thr Leu Gly Asn Ser Thr Ile Thr Thr Gln Glu
                 85                  90                  95

Ala Ala Asn Ala Ile Val Ala Tyr Gly Glu Trp Pro Thr Tyr Ile Asn
            100                 105                 110

Asp Ser Glu Ala Asn Pro Val Asp Ala Pro Thr Glu Pro Asp Val Ser
        115                 120                 125

Ser Asn Arg Phe Tyr Thr Leu Glu Ser Val Ser Trp Lys Thr Thr Ser
    130                 135                 140

Arg Gly Trp Trp Trp Lys Leu Pro Asp Cys Leu Lys Asp Met Gly Met
145                 150                 155                 160

Phe Gly Gln Asn Met Tyr Tyr His Tyr Leu Gly Arg Ser Gly Tyr Thr
                165                 170                 175

Ile His Val Gln Cys Asn Ala Ser Lys Phe His Gln Gly Ala Leu Gly
            180                 185                 190

Val Phe Leu Ile Pro Glu Phe Val Met Ala Cys Asn Thr Glu Ser Lys
        195                 200                 205

Thr Ser Tyr Val Ser Tyr Ile Asn Ala Asn Pro Gly Glu Arg Gly Gly
    210                 215                 220

Glu Phe Thr Asn Thr Tyr Asn Pro Leu Asn Thr Asp Ala Ser Glu Gly
225                 230                 235                 240

Arg Lys Phe Ala Ala Leu Asp Tyr Leu Leu Gly Ser Gly Val Leu Ala
                245                 250                 255

Gly Asn Ala Phe Val Tyr Pro His Gln Ile Ile Asn Leu Arg Thr Asn
            260                 265                 270

Asn Ser Ala Thr Ile Val Val Pro Tyr Val Asn Ser Leu Val Ile Asp
```

-continued

```
                275                 280                 285
Cys Met Ala Lys His Asn Asn Trp Gly Ile Val Ile Leu Pro Leu Ala
290                 295                 300
Pro Leu Ala Phe Ala Ala Thr Ser Ser Pro Gln Val Pro Ile Thr Val
305                 310                 315                 320
Thr Ile Ala Pro Met Cys Thr Glu Phe Asn Gly Leu Arg Asn Ile Thr
                325                 330                 335
Val Pro Val His Gln Gly Leu Pro Thr Met Asn Thr Pro Gly Ser Asn
                340                 345                 350
Gln Phe Leu Thr Ser Asp Asp Phe Gln Ser Pro Cys Ala Leu Pro Asn
            355                 360                 365
Phe Asp Val Thr Pro Ile His Ile Pro Gly Glu Val Lys Asn Met
        370                 375                 380
Met Glu Leu Ala Glu Ile Asp Thr Leu Ile Pro Met Asn Ala Val Asp
385                 390                 395                 400
Gly Lys Val Asn Thr Met Glu Met Tyr Gln Ile Pro Leu Asn Asp Asn
                405                 410                 415
Leu Ser Lys Ala Pro Ile Phe Cys Leu Ser Leu Ser Pro Ala Ser Asp
            420                 425                 430
Lys Arg Leu Ser His Thr Met Leu Gly Xaa Ile Leu Asn Tyr Tyr Thr
            435                 440                 445
His Trp Thr Gly Ser Ile Arg Phe Thr Phe Leu Phe Cys Gly Ser Met
    450                 455                 460
Met Ala Thr Gly Lys Leu Leu Leu Ser Tyr Ser Pro Pro Gly Ala Lys
465                 470                 475                 480
Pro Pro Thr Asn Arg Lys Asp Ala Met Leu Gly Thr His Ile Ile Trp
                485                 490                 495
Asp Leu Gly Leu Gln Ser Ser Cys Ser Met Val Ala Pro Trp Ile Ser
            500                 505                 510
Asn Thr Val Tyr Arg Arg Cys Ala Arg Asp Asp Phe Thr Glu Gly Gly
            515                 520                 525
Phe Ile Thr Cys Phe Tyr Gln Thr Arg Ile Val Val Pro Ala Ser Thr
        530                 535                 540
Pro Thr Ser Met Phe Met Leu Gly Phe Val Ser Ala Cys Pro Asp Phe
545                 550                 555                 560
Ser Val Arg Leu Leu Arg Asp Thr Pro His Ile Ser Gln Ser Lys Leu
                565                 570                 575
Ile Gly Arg Thr Gln Gly Ile Glu Asp Leu Ile Asp Thr Ala Ile Lys
            580                 585                 590
Asn Ala Leu Arg Val Ser Gln Pro Pro Ser Thr Gln Ser Thr Glu Ala
            595                 600                 605
Thr Ser Gly Val Asn Ser Gln Glu Val Pro Ala Leu Thr Ala Val Glu
    610                 615                 620
Thr Gly Ala Ser Gly Gln Ala Ile Pro Ser Asp Val Val Glu Thr Arg
625                 630                 635                 640
His Val Val Asn Tyr Lys Thr Arg Ser Glu Ser Cys Leu Glu Ser Phe
                645                 650                 655
Phe Gly Arg Ala Ala Cys Val Thr Ile Leu Ser Leu Thr Asn Ser Ser
            660                 665                 670
Lys Ser Gly Glu Glu Lys Lys His Phe Asn Ile Trp Asn Ile Thr Tyr
        675                 680                 685
Thr Asp Thr Val Gln Leu Arg Arg Lys Leu Glu Phe Phe Thr Tyr Ser
    690                 695                 700
```

```
Arg Phe Asp Leu Glu Met Thr Phe Val Phe Thr Glu Asn Tyr Pro Ser
705                 710                 715                 720

Thr Ala Ser Gly Glu Val Arg Asn Gln Val Tyr Gln Ile Met Tyr Ile
                725                 730                 735

Pro Pro Gly Ala Pro Arg Pro Ser Ser Trp Asp Asp Tyr Thr Trp Gln
            740                 745                 750

Ser Ser Ser Asn Pro Ser Ile Phe Tyr Met Tyr Gly Asn Ala Pro Pro
        755                 760                 765

Arg Met Ser Ile Pro Tyr Val Gly Ile Ala Asn Ala Tyr Ser His Phe
    770                 775                 780

Tyr Asp Gly Phe Ala Arg Val Pro Leu Glu Gly Glu Asn Thr Asp Ala
785                 790                 795                 800

Gly Asp Thr Phe Tyr Gly Leu Val Ser Ile Asn Asp Phe Gly Val Leu
            805                 810                 815

Ala Val Arg Ala Val Asn Arg Ser Asn Pro His Thr Ile His Thr Ser
            820                 825                 830

Val Arg Val Tyr Met Lys Pro Lys His Ile Arg Cys Trp Cys Pro Arg
        835                 840                 845

Pro Pro Arg Ala Val Leu Tyr Arg Gly Glu Gly Val Asp Met Ile Ser
    850                 855                 860

Ser Ala Ile Leu Pro Leu Thr Lys Val Asp Ser Ile Thr Thr Phe
865                 870                 875
```